US012672923B2

(12) United States Patent
Bozung

(10) Patent No.: US 12,672,923 B2
(45) Date of Patent: Jul. 7, 2026

(54) ROBOTIC HAND-HELD SURGICAL INSTRUMENT SYSTEMS AND METHODS

(71) Applicant: MAKO Surgical Corp., Weston, FL (US)

(72) Inventor: Timothy J. Bozung, Belding, MI (US)

(73) Assignee: MAKO Surgical Corp., Weston, FL (US)

( * ) Notice: Subject to any disclaimer, the term of this patent is extended or adjusted under 35 U.S.C. 154(b) by 239 days.

(21) Appl. No.: 18/262,134

(22) PCT Filed: Jan. 20, 2022

(86) PCT No.: PCT/US2022/013115
§ 371 (c)(1),
(2) Date: Jul. 19, 2023

(87) PCT Pub. No.: WO2022/159574
PCT Pub. Date: Jul. 28, 2022

(65) Prior Publication Data
US 2024/0090957 A1     Mar. 21, 2024

Related U.S. Application Data

(60) Provisional application No. 63/245,420, filed on Sep. 17, 2021, provisional application No. 63/139,635, filed on Jan. 20, 2021.

(51) Int. Cl.
*A61B 34/00*       (2016.01)
*A61B 34/30*       (2016.01)
*A61B 34/37*       (2016.01)
(52) U.S. Cl.
CPC .............. *A61B 34/25* (2016.02); *A61B 34/37* (2016.02); *A61B 34/74* (2016.02); *A61B 2034/304* (2016.02)

(58) Field of Classification Search
None
See application file for complete search history.

(56) References Cited

U.S. PATENT DOCUMENTS

| | | | |
|---|---|---|---|
| 7,035,716 B2 | 4/2006 | Harris et al. | |
| 7,422,582 B2 | 9/2008 | Malackowski et al. | |
| | (Continued) | | |

FOREIGN PATENT DOCUMENTS

| | | |
|---|---|---|
| JP | 2019501677 A | 1/2019 |
| JP | 2021501011 A | 1/2021 |
| | (Continued) | |

OTHER PUBLICATIONS

Partial International Search Report for Application No. PCT/US2022/013115 dated May 10, 2022, 3 pages.
(Continued)

*Primary Examiner* — Carl H Layno
*Assistant Examiner* — Bryan McAllister Lee
(74) *Attorney, Agent, or Firm* — Howard & Howard Attorneys PLLC

(57) ABSTRACT

The present teachings generally include a hand-held surgical robotic system for supporting a surgical tool, the handheld surgical robotic system comprising a hand-held portion, a tool support movably coupled to the hand-held portion, the tool support configured to support a surgical tool, a plurality of actuators operatively interconnecting the tool support and the hand-held portion, the plurality of actuators configured to move the tool support relative to the hand-held portion in a plurality of degrees of freedom, a controller in communication with the plurality of actuators and a flexible circuit connecting the controller with each of the plurality of actuators, such that the flexible circuits are arranged to maintain the connection between the controller and the plurality actuators and/or an input module while the tool
(Continued)

support is moved in the plurality of degrees of freedom relative to the hand-held portion.

20 Claims, 44 Drawing Sheets

(56) References Cited

U.S. PATENT DOCUMENTS

| | | | |
|---|---|---|---|
| 8,342,748 | B2 | 1/2013 | Gierer |
| 8,617,174 | B2 | 12/2013 | Axelson, Jr. et al. |
| 8,876,830 | B2 | 11/2014 | Hodorek et al. |
| 9,008,757 | B2 | 4/2015 | Wu |
| 9,060,794 | B2 | 6/2015 | Kang et al. |
| 9,707,043 | B2 | 7/2017 | Bozung |
| 9,820,753 | B2 | 11/2017 | Walen et al. |
| 10,350,014 | B2 | 7/2019 | Beelen et al. |
| 10,500,005 | B2 | 12/2019 | Weir et al. |
| 10,646,292 | B2 | 5/2020 | Solomon et al. |
| 10,687,823 | B2 | 6/2020 | Mac an Tuile et al. |
| 11,185,378 | B2 | 11/2021 | Weir et al. |
| 12,290,322 | B2 | 5/2025 | Bonny et al. |
| 2013/0060278 | A1 | 3/2013 | Bozung et al. |
| 2019/0125378 | A1* | 5/2019 | Shelton, IV ........... A61B 17/29 |
| 2019/0133703 | A1 | 5/2019 | Seow et al. |
| 2020/0390507 | A1 | 12/2020 | Sadaka |

FOREIGN PATENT DOCUMENTS

| | | |
|---|---|---|
| WO | 2019089300 A2 | 5/2019 |
| WO | 2021011646 A2 | 1/2021 |
| WO | 2021137048 A1 | 7/2021 |
| WO | 2021137051 A1 | 7/2021 |

OTHER PUBLICATIONS

International Search Report for Application No. PCT/US2022/013115 dated Jul. 4, 2022, 4 pages.
English language abstract for JP 2019-501677 A extracted from espacenet.com database on Jul. 1, 2025, 2 pages.
English language abstract for JP 2021-501011 A extracted from espacenet.com database on Jul. 1, 2025, 5 pages.

* cited by examiner

424

434

417

436

415

ROBOTIC HAND-HELD SURGICAL INSTRUMENT SYSTEMS AND METHODS

CROSS-REFERENCE TO RELATED APPLICATIONS

The present application is a National Stage of International Patent Application No. PCT/US2022/013115, filed on Jan. 20, 2022, which claims priority to and all the benefits of U.S. Provisional Patent Application No. 63/245,420, filed on Sep. 17, 2021, and of U.S. Provisional Patent Application No. 63/139,635, filed on Jan. 20, 2021, the entire contents of which are hereby expressly incorporated herein by reference.

BACKGROUND

Navigation systems (also referred to as tracking systems) can be used to properly align and secure jigs, as well as track a position and/or orientation of a surgical tool used to resect tissue from a patient. Tracking systems typically employ one or more trackers associated with the tool and the tissue being resected. A display can then be viewed by a user to determine a current position of the tool relative to a desired cut path of tissue to be removed. The display may be arranged in a manner that requires the user to look away from the tissue and surgical site to visualize the tool's progress. This can distract the user from focusing on the surgical site. Also, it may be difficult for the user to place the tool in a desired manner.

Robotically assisted surgery typically relies on large robots with robotic arms that can move in six degrees of freedom (DOF). These large robots may be cumbersome to operate and maneuver in the operating room.

There is a need for systems and methods to address one or more of these challenges.

SUMMARY

The present teachings generally include a hand-held surgical robotic system for supporting a surgical tool, the handheld surgical robotic system comprising a hand-held portion, a blade support movably coupled to the hand-held portion, the blade support configured to support a saw blade, a plurality of actuators operatively interconnecting the blade support and the hand-held portion, the plurality of actuators configured to move the blade support relative to the hand-held portion in a plurality of degrees of freedom, a controller on the blade support, the controller in communication with the plurality of actuators, and a plurality of flexible circuits connecting the controller with each of the plurality of actuators, such that the flexible circuits are configured to maintain the connection between the controller and the plurality actuators while the blade support is moved in the plurality of degrees of freedom relative to the hand-held portion.

Another aspect of the present teachings includes an instrument comprising: a hand-held portion to be held by a user; a tool support coupled to the hand-held portion, the tool support comprising a tool drive motor to drive motion of the tool, an actuator assembly operatively interconnecting the tool support and the hand-held portion to move the tool support to move the tool in a plurality of degrees of freedom relative to the hand-held portion to align the tool, the actuator assembly including a plurality of actuators, each actuator including a motor and a position sensor; a controller connected with the tool support, the controller in communication with the tool drive motor and each actuator of the plurality of actuators; an input module disposed within the hand held portion, the input module including: a trigger, a sensor that outputs a signal representative of a distance or position of the trigger relative to the sensor, sending the output signal to the controller; and a plurality of flexible circuits connecting the controller to the plurality of actuators and the input module, the plurality of flexible circuits are configured to maintain the connection between the controller and the plurality actuators and the input module while the tool support is moved in the plurality of degrees of freedom relative to the hand-held portion; wherein the corresponding flexible circuit connected with the input module is guided by a tensioning assembly including a biasing member to apply tension to the flexible circuit while the tool support moves in the plurality of degrees of freedom relative to the hand-held portion.

In another aspect, a hand-held robotic surgical instrument for use with a tool to perform surgery including a component to provide magnetic isolation to a sensor is provided. The robotic instrument may include a hand-held portion to be held by a user; a tool support coupled to the hand-held portion, the tool support including a tool drive motor to drive motion of a tool, the tool drive motor being mounted to the tool support and an actuator assembly to move the tool support in a plurality of degrees of freedom relative to the hand-held portion. The actuator assembly may include a plurality of actuators, wherein each actuator of the plurality of actuators including an actuator housing, a lead screw movably coupled to the actuator housing, one of the actuator housing and the lead screw including a magnet, and other of the actuator housing and the lead screw including an actuator sensor for detecting a position of the actuator. The instrument may include a linkage operatively interconnecting the tool support and the hand-held portion, wherein at least one component of the linkage is formed from a ferromagnetic material. The instrument may further include an input module mounted to the hand-held portion, the input module including a trigger movable relative to the hand-held portion; with one of the hand-held portion and the trigger including a trigger magnet and other of the hand-held portion and the trigger including a trigger sensor configured to output a signal representative of a trigger position.

In yet another aspect, a method of maintaining an electrical connection between two parts of a hand-held robotic instrument is provided. The robotic instrument may include a hand-held portion to be held by a user, a tool support coupled to the hand-held portion, an actuator assembly to move the tool support in a plurality of degrees of freedom relative to the hand-held portion, the actuator assembly including a plurality of actuators, a controller mounted to the tool support or the hand-held portion, a sensor that outputs a signal, the sensor coupled to the other of the hand-held portion and the tool support (opposite the controller), the sensor connected to the controller using a flexible conductor, and a tensioning assembly including a biasing member, the method including moving the tool support relative to hand-held portion with the plurality of actuators in at least one of the plurality of degrees of freedom; tensioning the flexible conductor with the tensioning assembly while the actuator assembly moves in the at least one of the plurality of degrees of freedom.

DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Overview

Figure 1:
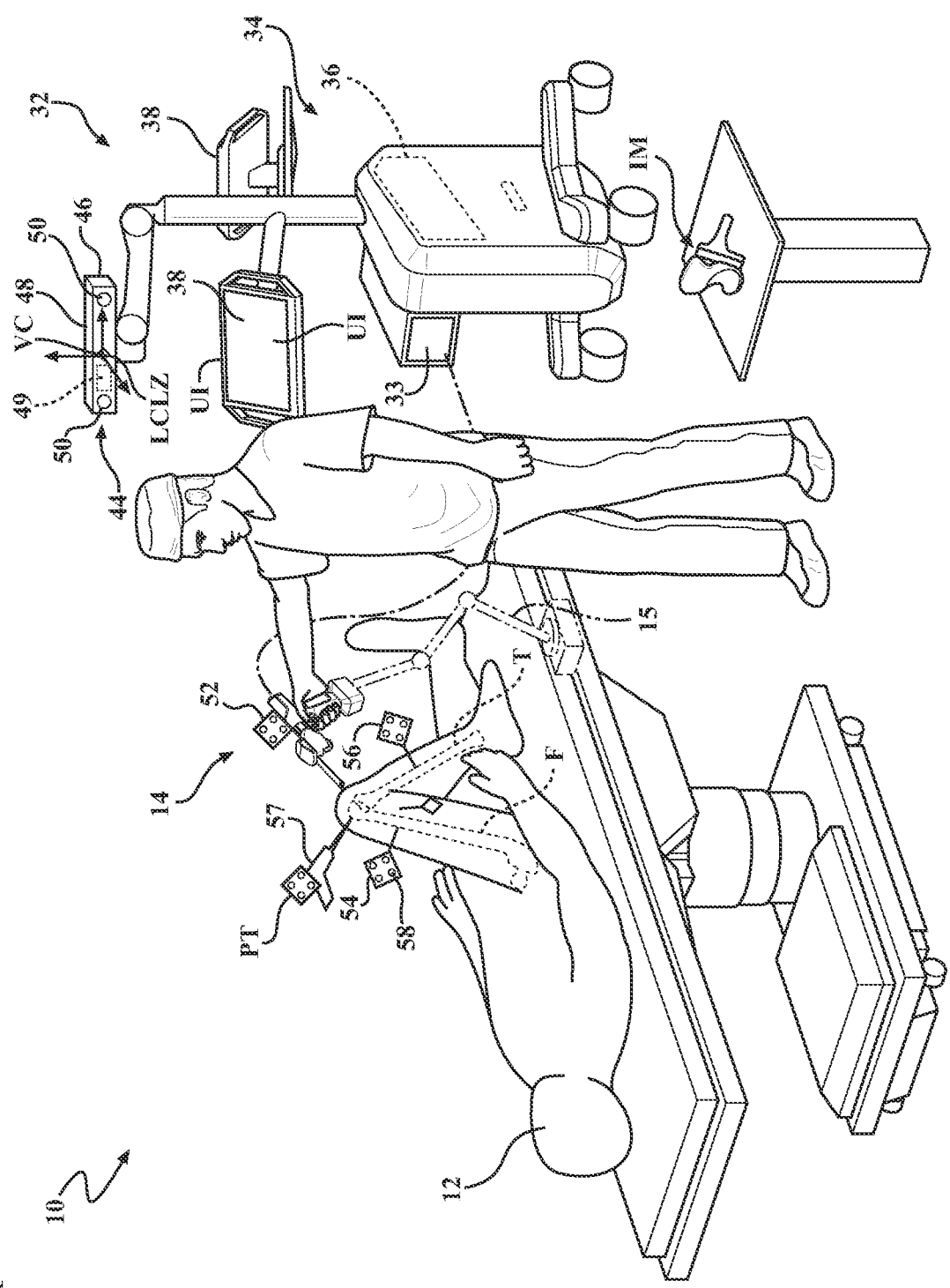
FIG. 1 is a perspective view of a robotic system.

Referring to FIG. 1, a robotic system 10 is illustrated. The robotic system 10 is shown performing a total knee procedure on a patient 12 to resect portions of a femur F and tibia T of the patient 12 so that the patient 12 can receive a total knee implant IM. The robotic system 10 may be used to perform other types of surgical procedures, including procedures that involve hard/soft tissue removal, or other forms of treatment. For example, treatment may include cutting tissue, coagulating tissue, ablating tissue, stapling tissue, suturing tissue, or the like. In some examples, the surgical procedure involves knee surgery, hip surgery, shoulder surgery, spine surgery, and/or ankle surgery, and may involve removing tissue to be replaced by surgical implants, such as knee implants, hip implants, shoulder implants, spine implants, and/or ankle implants. The robotic system 10 and techniques disclosed herein may be used to perform other procedures, surgical or non-surgical, and may be used in industrial applications or other applications where robotic systems are utilized.

Figure 2:
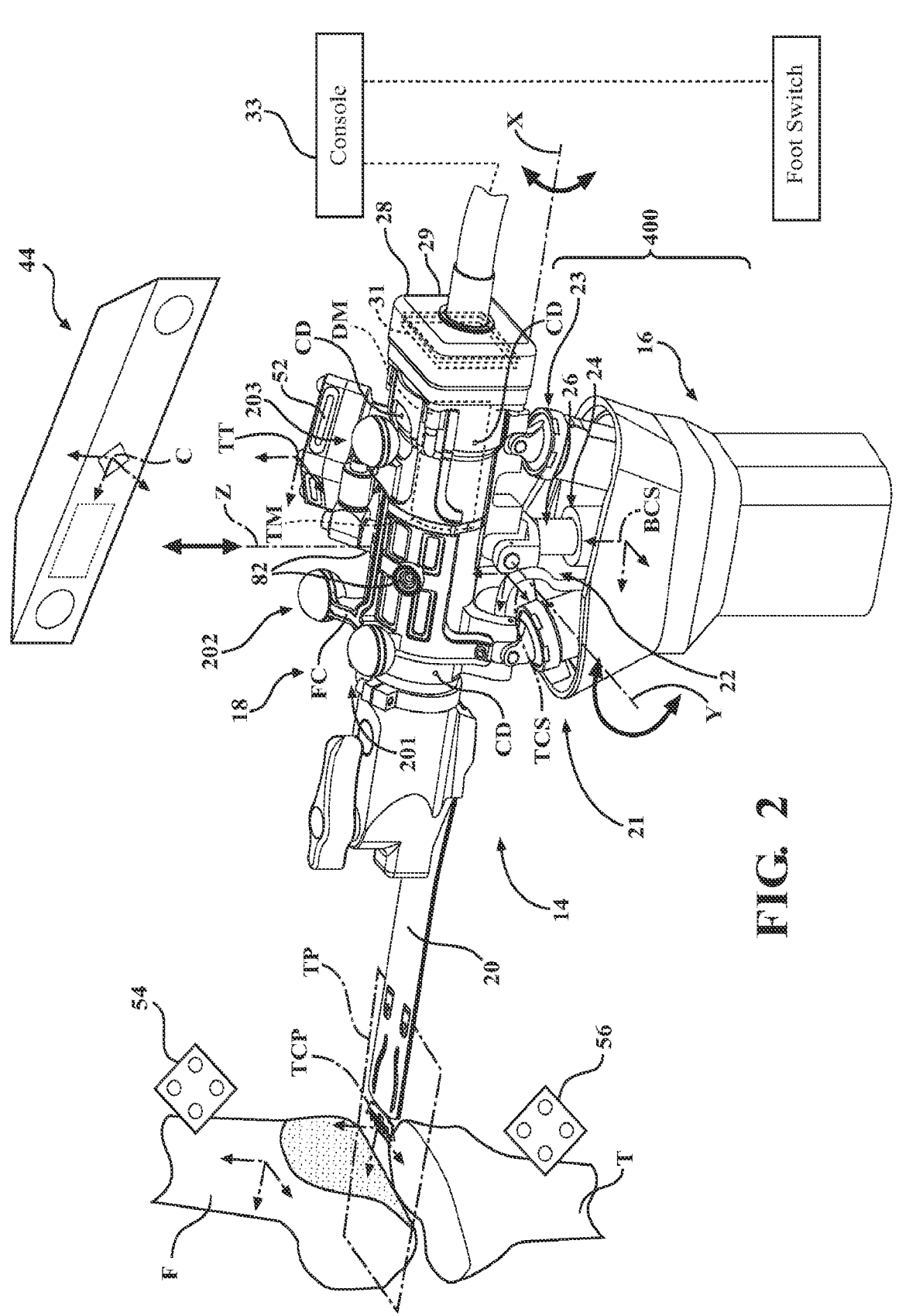
FIG. 2 is a perspective view of a robotic instrument being used to cut one or more planes on a femur and a tibia to receive a total knee implant.
Figures 3A, 3B, 3C:
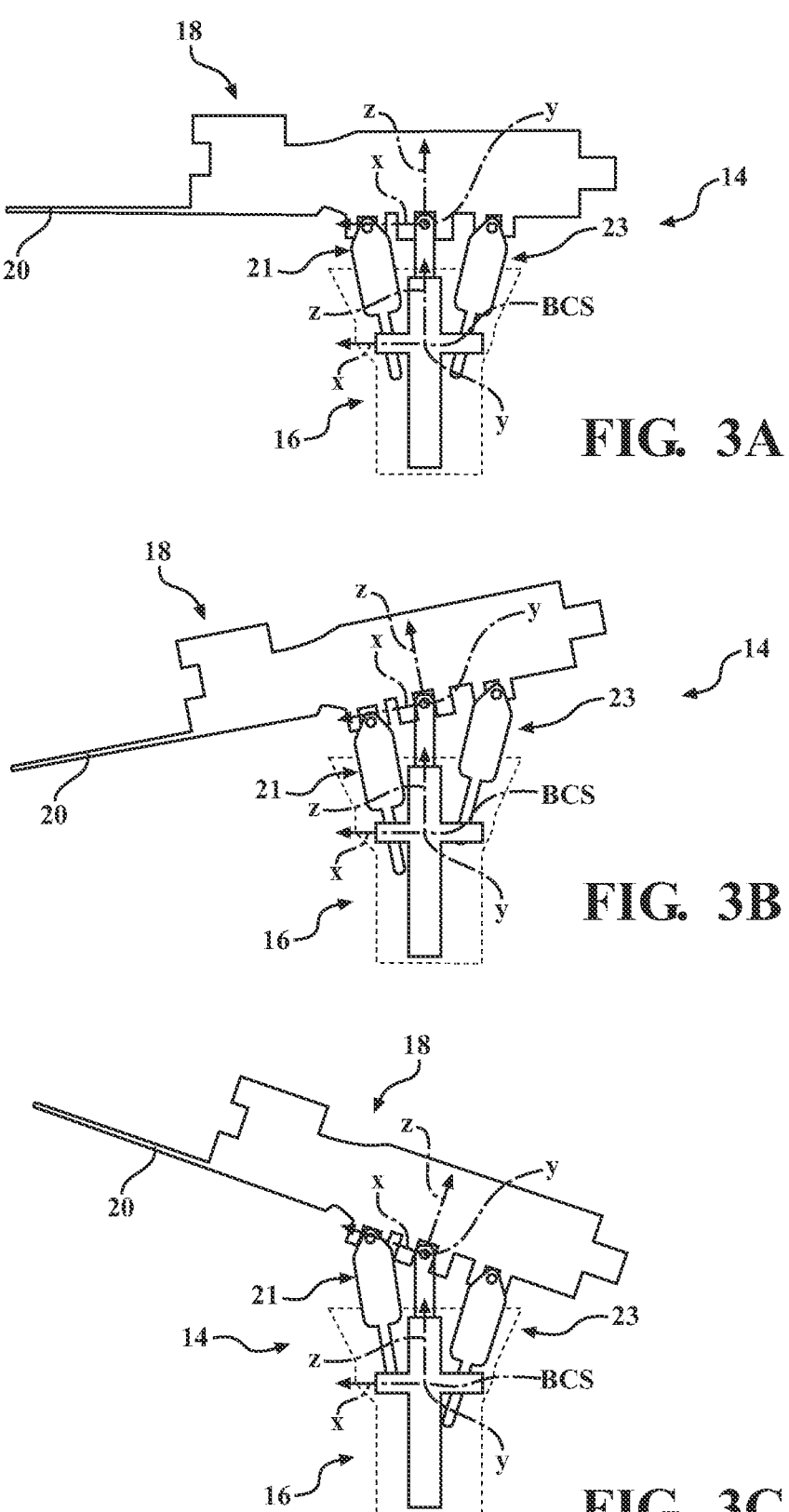
FIGS. 3A-3C are illustrations of various pitch orientations of the robotic instrument.
Figures 4A, 4B, 4C:
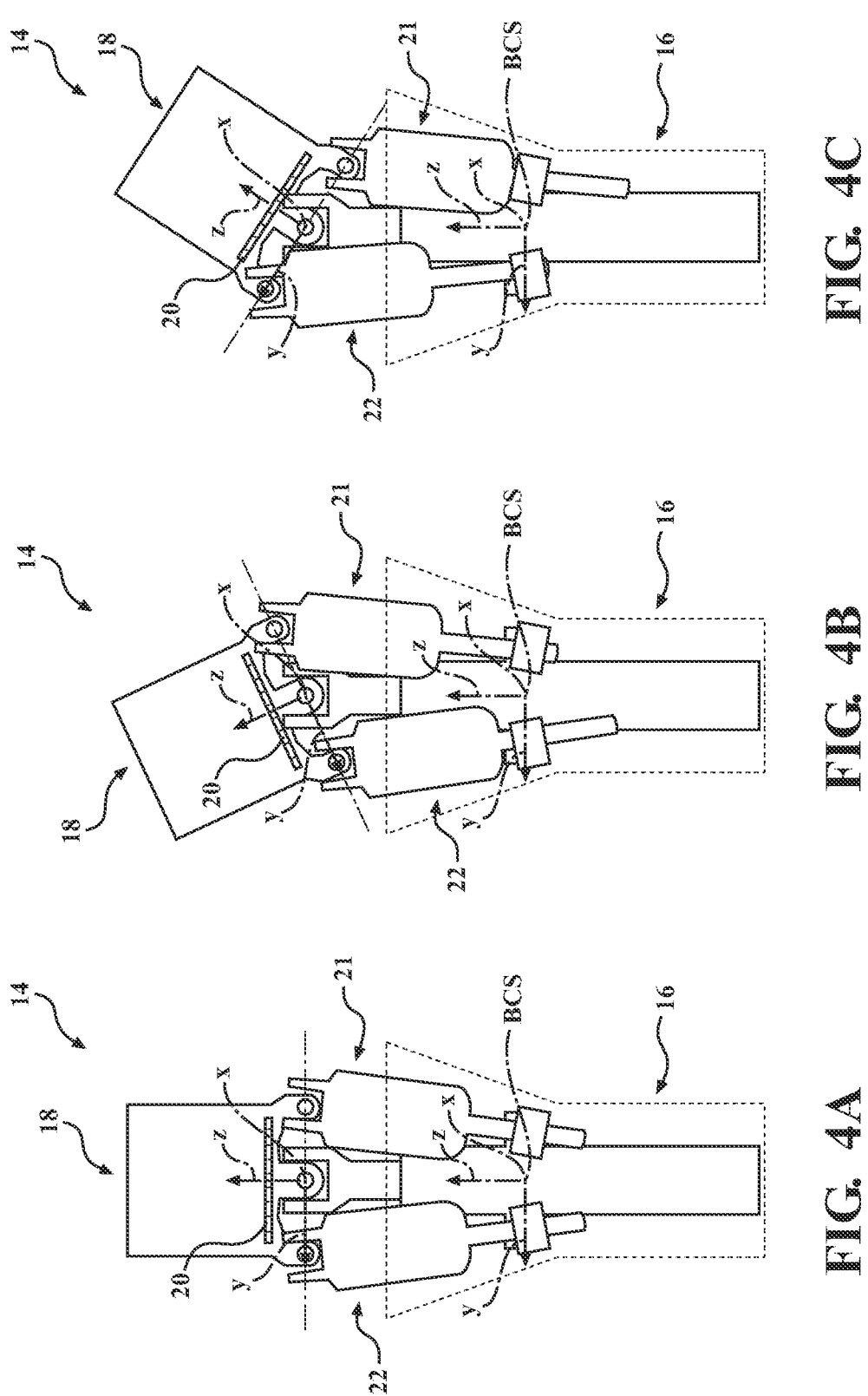
FIGS. 4A-4C are illustrations of various roll orientations of the robotic instrument.
Figures 5A, 5B, 5C:
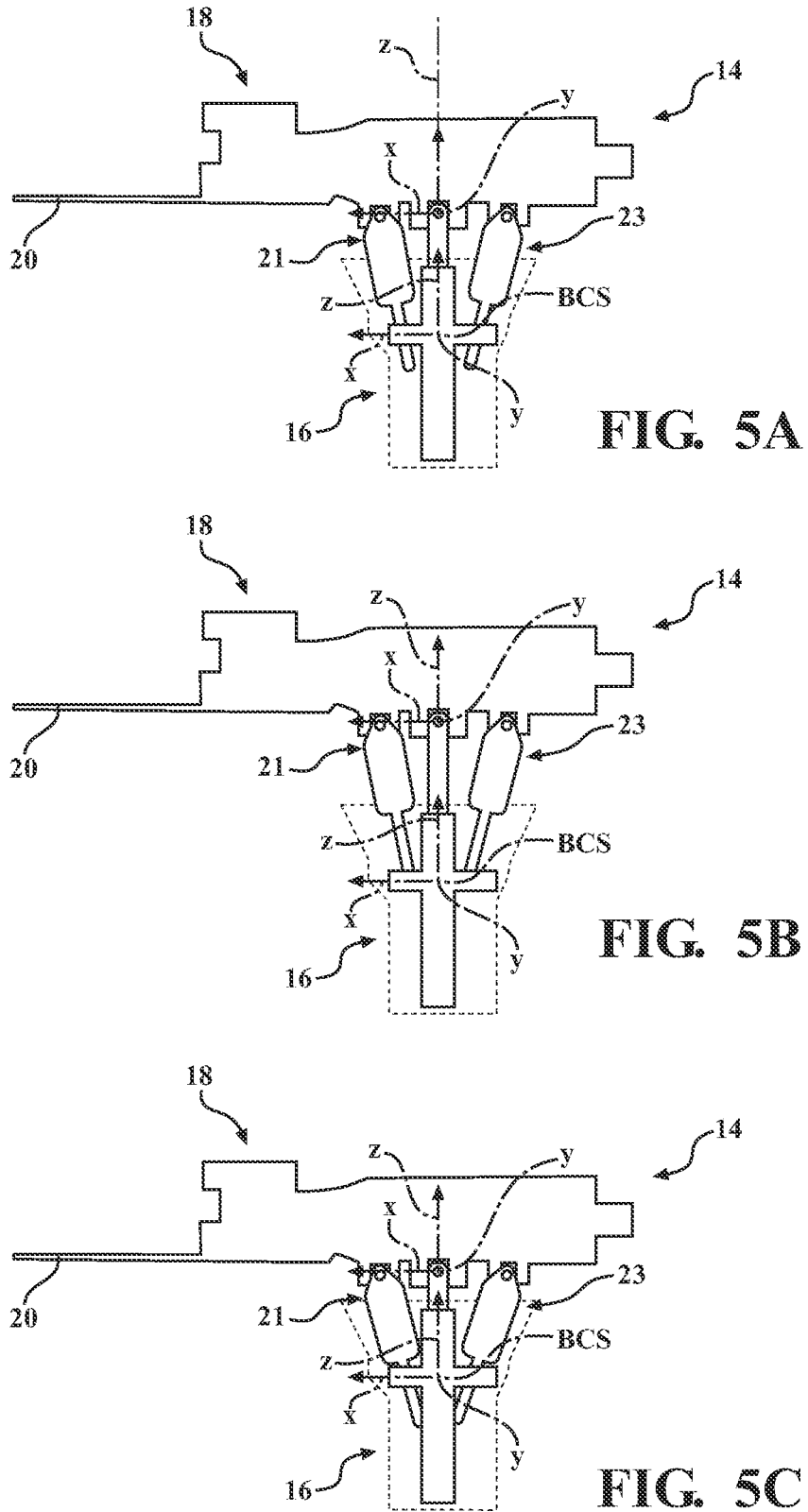
FIGS. 5A-5C are illustrations of various z-axis translation positions of the robotic instrument.

Referring to FIGS. 1 and 2, the robotic system 10 includes an instrument 14. In some examples, a user manually holds and supports the instrument 14 (as shown in FIG. 1). In some examples, the user may manually hold the instrument 14 while the instrument is being at least partially, or fully, supported by an assistive device, such as a passive arm (e.g., linkage arm with locking joints, weight-balancing arm), an active arm, and/or the like. As best shown in FIGS. 1 and 2, the instrument 14 comprises a hand-held portion 16 for being manually grasped and/or supported by the user and/or assistive device.

The instrument 14 may be freely moved and supported by a user without the aid of a guide arm, e.g., configured to be held by a human user while effecting physical removal of material such that the weight of the tool is supported solely by a hand of the user during the procedure. Put another way, the instrument 14 may be configured to be held such that the user's hand is supporting the instrument 14 against the force of gravity. The instrument 14 may weigh 8 lbs. or less, 6 lbs. or less, 5 lbs. or less, or even 3 lbs. or less. The instrument
14 may have a weight corresponding to ANSI/AAMI HE75:
2009. The instrument 14 also comprises a tool support 18 for
receiving a tool 20. In some examples, when the tool 20 is
a saw blade 302, the tool support 18 may be referred to as
a blade support. The method for operating the instrument 14
may include a user suspending the weight of the instrument
14 without any assistance from a passive arm or robotic arm.
Alternately, the weight of the instrument 14 may be sup-
ported through use of a counter-balanced passive arm,
assistive device, or active robotic arm, such that the user
does not have to support the entire weight of the instrument.
In such cases, the user may still grasp the hand-held portion
16 in order to interact with and/or guide the instrument 14.
The passive arm and the contents of U.S. Pat. No. 9,060,794
to Kang et al. are incorporated herein by reference. Further-
more, the robotic system 10, in some examples, may be free
from a robot arm having more than one joint in series.

The tool 20 couples to the tool support 18 to interact with
the anatomy in certain operations of the robotic system 10
described further below. The tool 20 may also be referred to
as an end effector. The tool 20 may be removable from the
tool support 18 such that new/different tools 20 can be
attached when needed. The tool 20 may also be permanently
fixed to the tool support 18. The tool 20 may comprise an
energy applicator designed to contact the tissue of the patient
12. In some examples, the tool 20 may be a saw blade, as
shown in FIGS. 1 and 2, or other type of cutting accessory.
In such instances, the tool support may be referred to as a
blade support. It should be appreciated that in any instance
where blade support is referred to, it may be substituted for
the term 'tool support' and vice-versa. However, other tools
may be contemplated, such as the contents of U.S. Pat. No.
9,707,043 to Bozung, which is hereby incorporated herein
by reference. In some examples, the tool 20 may be a drill
bit, a driver, an ultrasonic vibrating tip, a bur, a stapler, or the
like. The tool 20 may comprise the blade assembly and drive
motor to cause oscillatory motion of the blade as shown in
U.S. Pat. No. 9,820,753 to Walen et al. or U.S. Pat. No.
10,687,823, hereby incorporated herein by reference. Alter-
native rotary driving motors are contemplated. Such driving
components may comprise a transmission TM coupled to the
drive motor DM to convert rotary motion from the drive
motor DM into oscillating motion of the tool 20.

The system and methods described in PCT/US2020/
042128, entitled "Robotic Handheld Surgical Instrument
Systems and Methods", filed on Jul. 15, 2020, are also
hereby incorporated by reference.

An actuator assembly 400 comprising one or more actua-
tors 21, 22, 23 move the tool support 18 in three degrees of
freedom relative to the hand-held portion 16 to provide
robotic motion that assists in placing the tool 20 at a desired
position and/or orientation (e.g., at a desired pose relative to
the femur F and/or tibia T during resection), while the user
holds the hand-held portion 16. The actuator assembly 400
may comprise actuators 21, 22, 23 that are arranged in
parallel, in series, or a combination thereof. In some
examples, the actuators 21, 22, 23 move the tool support 18
in three or more degrees of freedom relative to the hand-held
portion 16. In some examples, the actuator assembly 400 is
configured to move the tool support 18 relative to the
hand-held portion 16 in at least two degrees of freedom,
such as pitch and z-axis translation. In some examples, such
as shown herein, the actuators 21, 22, 23 move the tool
support 18 and its associated tool support coordinate system
TCS in only three degrees of freedom relative to the hand-
held portion 16 and its associated base coordinate system

6

Figure 6:
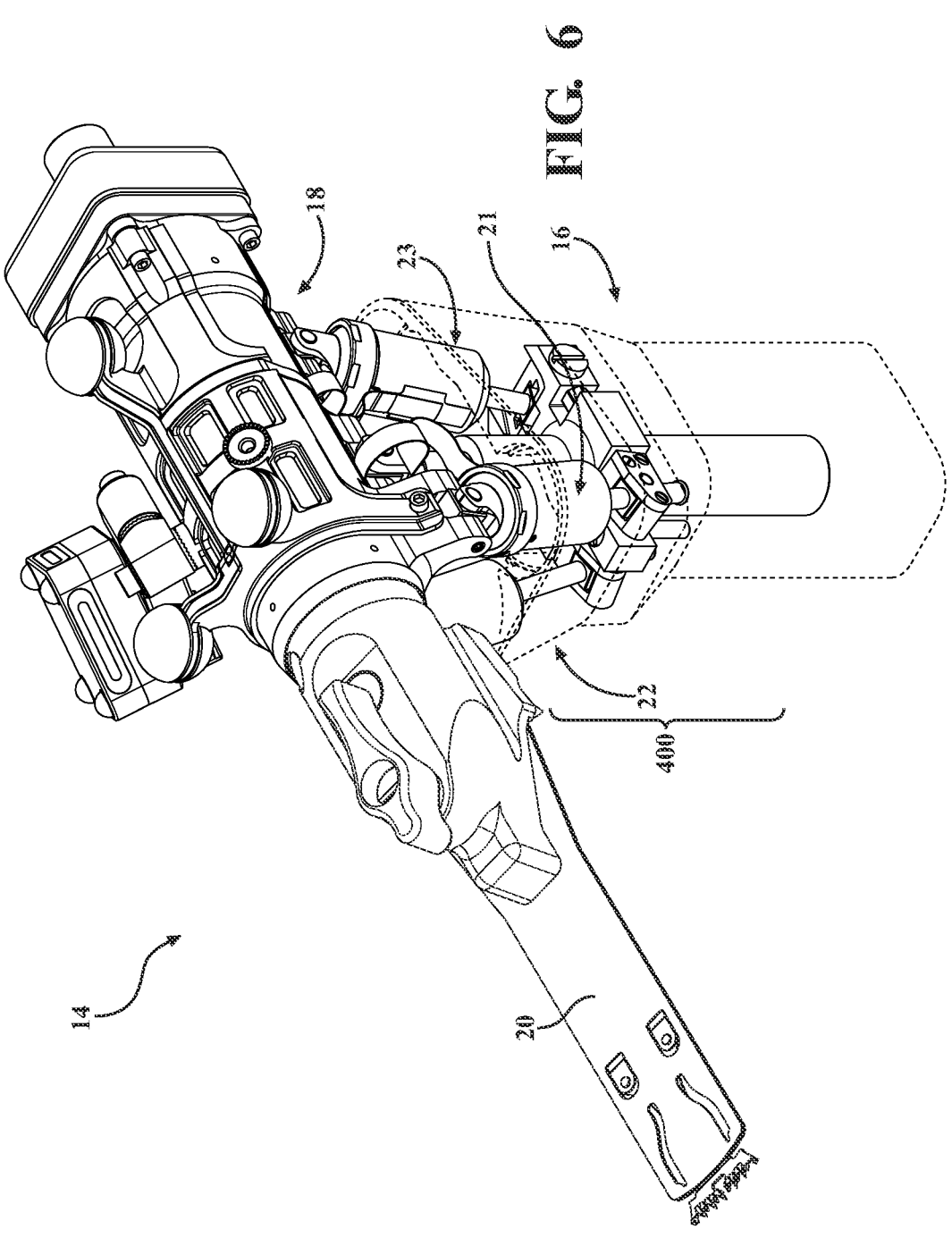
FIG. 6 is a front perspective view of the robotic instrument illustrating one particular pose of a tool support relative to a hand-held portion.

BCS. For example, the tool support 18 and its tool support
coordinate system TCS may: rotate about its y-axis to
provide pitch motion; rotate about its x-axis to provide roll
motion; and translate along an axis Z coincident with a
z-axis of the base coordinate system BCS to provide z-axis
translation motion. The allowed motions in pitch, roll, and
z-axis translation are shown by arrows in FIG. 2 and in the
schematic illustrations of FIGS. 3A-3C, 4A-4C, and 5A-5C,
respectively. FIG. 6 provides one example of a pose of the
tool support 18 and a pose of the hand-held portion 16 within
the range of motion of the instrument 14. In some examples,
not shown in the figures, actuators may move the tool
support 18 in four or more degrees of freedom relative to the
hand-held portion 16.

Referring back to FIG. 2, a constraint assembly 24 having
a passive linkage 26 may be used to constrain movement of
the tool support 18 relative to the hand-held portion 16 in
one or more three degrees of freedom. The constraint
assembly 24 may comprise any suitable linkage (e.g., one or
more links having any suitable shape or configuration) to
constrain motion as described herein. In the example shown
in FIG. 2, the constraint assembly 24 operates to limit
motion of the tool support coordinate system TCS by:
constraining rotation about the z-axis of the base coordinate
system BCS to constrain yaw motion; constraining transla-
tion in the x-axis direction of the base coordinate system
BCS to constrain x-axis translation; and constraining trans-
lation in the y-axis direction of the base coordinate system
BCS to constrain y-axis translation. The actuators 21, 22, 23
and constraint assembly 24, in certain situations described
further below, are controlled to effectively mimic the func-
tion of a physical cutting guide, such as a physical saw
cutting guide.

Figure 7:
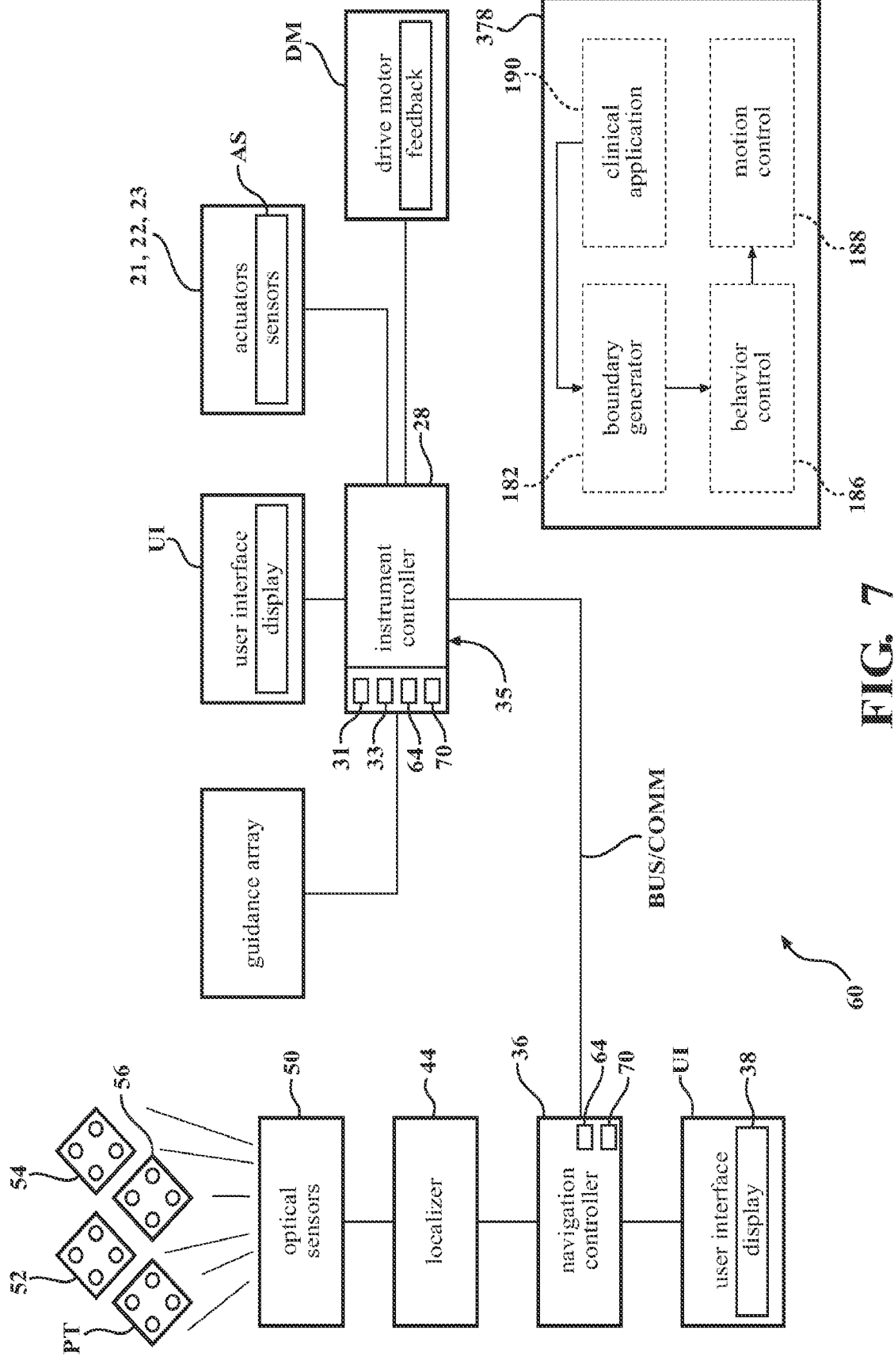
FIG. 7 is a block diagram of a control system, and also illustrates various software modules.

Referring to FIG. 7, an controller 28, or other type of
control unit, is provided to control one or more aspects of the
instrument 14. The instrument controller 28 may comprise
one or more computers, or any other suitable form of
controller that directs operation of the instrument 14 and
motion of the tool support 18 (and tool 20) relative to the
hand-held portion 16. The controller 28 may have a central
processing unit (CPU) and/or other processors, memory, and
storage (not shown). The controller 28 is loaded with
software as described below. The processors could include
one or more processors to control operation of the instru-
ment 14. The processors can be any type of microprocessor,
multi-processor, and/or multi-core processing system. The
instrument controller 28 may additionally, or alternatively,
comprise one or more microcontrollers, field programmable
gate arrays, systems on a chip, discrete circuitry, and/or
other suitable hardware, software, or firmware that is
capable of carrying out the functions described herein. The
term processor is not intended to limit any embodiment to a
single processor. The instrument 14 may also comprise a
user interface UI with one or more displays and/or input
devices (e.g., triggers, push buttons, foot switches, key-
board, mouse, microphone (voice-activation), gesture con-
trol devices, touchscreens, etc.).

The control system 60 further includes one or more
software programs and software modules. The software
modules may be part of the program or programs that
operate on the navigation controller 36, instrument control-
ler 28, or both, to process data to assist with control of the
robotic system 10. The software programs and/or modules
include computer readable instructions stored in non-tran-
sitory memory 64 on the navigation controller 36, instru-
ment controller 28, or both, to be executed by one or more
processors 70 of the controllers 28, 36. The memory 64 may be any suitable configuration of memory, such as RAM, non-volatile memory, etc., and may be implemented locally or from a remote database. Additionally, software modules for prompting and/or communicating with the user may form part of the program or programs and may include instructions stored in memory 64 on the navigation controller 36, instrument controller 28, or both. The user may interact with any of the input devices of the navigation user interface UI or other user interface UI to communicate with the software modules. The user interface software may run on a separate device from the navigation controller 36, and/or instrument controller 28.

The instrument controller 28 controls one or more aspect of the operation of the tool 20, such as by controlling power to the tool 20 (e.g., to the drive motor DM of the tool 20 that controls cutting motion) and/or controlling movement of the tool support 18 relative to the hand-held portion 16 (e.g., by controlling the actuators 21, 22, 23). The instrument controller 28 or other aspect of the system controls a state (e.g., position and/or orientation) of the tool support 18 and the tool 20 with respect to the hand-held portion 16. The instrument controller 28 or other aspect of the system can control velocity (linear or angular), acceleration, or other derivatives of motion of the tool 20 relative to the hand-held portion 16 and/or relative to the anatomy that is caused by the actuators 21, 22, 23.

As shown in FIG. 2, the instrument controller 28 may comprise a control housing 29 mounted to the tool support 18, and/or the hand-held portion 16 or a combination thereof with one or more control boards 31 (e.g., one or more printed circuit boards and associated electronic components) located inside the control housing 29. The control boards 31 may comprise microcontrollers, field programmable gate arrays (FPGA), drivers, memory, sensors, or other electronic components for controlling the actuators 21, 22, 23 and the drive motor DM (e.g., via motor controllers). The system may also comprise an off-board control console 33 in data and power communication with the control boards 31/instrument controller 28. The sensors S, actuators 21, 22, 23, and/or drive motor DM described herein may feed signals to the control boards 31 or instrument controller 28, which transmit data signals out to the console 33 for processing, and the console 33 may feed control commands (e.g. current commands, torque commands, velocity commands, angle commands, position commands, or a combination thereof, as well as various control and configuration parameters) back to the control boards 31/instrument controller in order to power and control the actuators 21, 22, 23 and/or the drive motor M. It is contemplated that the processing may also be performed on the control board(s) of the control housing. In some examples, the processing of the control algorithms may be distributed between the console and the control housing. In one example, the position control and velocity control calculations may be in the console and current control may be in the field programmable gate arrays located in the control house. Of course, it is contemplated that no separate control housing is necessary, and/or the processing can be performed in any number of different locations.

In some versions, the console 33 may comprise a single console for powering and controlling the actuators 21, 22, 23, and the drive motor M. In some versions, the console 33 may comprise one console for powering and controlling the actuators 21, 22, 23 and a separate console for powering and controlling the drive motor M. One such console for powering and controlling the drive motor DM may be like that described in U.S. Pat. No. 7,422,582, filed on Sep. 30, 2004, entitled, "Control Console to which Powered Surgical Handpieces are Connected, the Console Configured to Simultaneously Energize more than one and less than all of the Handpieces," hereby incorporated herein by reference. Flexible conductors, shown as flexible circuits FC, also known as flexible circuits, may interconnect the actuators 21, 22, 23 and/or other components with the instrument controller 28. For example, flexible circuits FC may be provided between the actuators 21, 22, 23, and the control boards 31. Other forms of connections, wired or wireless, may additionally, or alternatively, be present between components.

Referring briefly back to FIG. 1, the robotic system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated herein by reference. The navigation system 32 tracks movement of various objects. Such objects include, for example, the instrument 14, the tool 20 and the anatomy, e.g., the femur F and tibia T. The navigation system 32 tracks these objects to gather state information of each object with respect to a (navigation) localizer coordinate system LCLZ. As used herein, the state of an object includes, but is not limited to, data that defines the position and/or orientation of the tracked object (e.g., coordinate systems thereof) or equivalents/derivatives of the position and/or orientation. For example, the state may be a pose of the object, and/or may include linear velocity data, angular velocity data, and the like.

The navigation system 32 may include a cart assembly 34 that houses a navigation controller 36, and/or other types of control units. A navigation user interface UI is in operative communication with the navigation controller 36. The navigation user interface UI includes one or more displays 38. The navigation system 32 is capable of displaying graphical representations of the relative states of the tracked objects to the user using the one or more displays 38. The navigation user interface UI further comprises one or more input devices to input information into the navigation controller 36 or otherwise to select/control certain aspects of the navigation controller 36. Such input devices include interactive touchscreen displays. However, the input devices may include any one or more of push buttons, pointer, foot switches, a keyboard, a mouse, a microphone (voice-activation), gesture control devices, and the like. In some examples, the user may use buttons located on the pointer to navigate through icons and menus of the user interfaces UI to make selections, configuring the robotic system 10 and/or advancing through the workflow.

The navigation system 32 also includes a localizer 44 coupled to the navigation controller 36. In one example, the localizer 44 is an optical localizer and includes a camera unit 46. The camera unit 46 has an outer casing 48 that houses one or more optical sensors 50. The localizer 44 may comprise its own localizer controller 49 and may further comprise a video camera VC.

The navigation system 32 includes one or more trackers. In some examples, the trackers include a pointer tracker PT, a tool tracker 52, a first patient tracker 54, and a second patient tracker 56. In the illustrated example of FIG. 1, the tool tracker 52 is firmly attached to the instrument 14, the first patient tracker 54 is firmly affixed to the femur F of the patient 12, and the second patient tracker 56 is firmly affixed to the tibia T of the patient 12. In this example, the patient trackers 54, 56 are firmly affixed to sections of bone. The trackers 52, 54, 56 and pointer tracker are registered to their respective objects (e.g. bone, tool) and the navigation system 32 manually, automatically, or a combination thereof. In some examples, the pointer tracker PT is firmly affixed to a pointer 57 and used for registering the anatomy to one or more coordinate systems, including the localizer coordinate system LCLZ and/or used for other calibration and/or registration functions. In one example, the pointer 57 may be used to register the patient trackers 54, 56 to the bone which the tracker 54, 56 is attached, respectively, and the tool tracker 52 (and optionally 53) to the tool support 18, the tool 20, the hand-held portion 16, or a combination thereof. In some examples, the pointer tracker PT may be used to register the TCP of the instrument 14 to the tracker 52 relative to a tracker coordinate system. This way, if the localizer 44 is moved from position to position, the registration of the instrument 14 is located relative to the tool tracker 52. However, other means of registration of the trackers 52, 54, 56 are contemplated and may be implemented together or separately with the pointer tracker PT. Other tracker locations are also contemplated.

Throughout this description, various transforms are described, such as 'bone to tracker' or 'instrument TCP to tracker', i.e., relative to the 'tracker coordinate system' rather than to the LCTZ coordinate system. The localizer coordinate system may be used as an intermediate coordinate system during registration and bone prep, since all tracked objects are measured with respect to LCTZ. During registration, ultimately the various localizer-referred poses are combined mathematically, and registration results are stored 'with respect to a tracker', such that if the camera (i.e., LCTZ) moves, the registration is still valid.

The tool tracker 52 may be affixed to any suitable component of the instrument 14, and in some versions may be attached to the hand-held portion 16, the tool support 18, directly to the tool 20, or a combination thereof. The trackers 52, 54, 56, PT may be fixed to their respective components in any suitable manner, such as by fasteners, clamps, or the like. For example, the trackers 52, 54, 56, PT may be rigidly fixed, flexibly connected (optical fiber), or not physically connected at all (ultrasound), as long as there is a suitable (supplemental) way to determine the relationship (measurement) of that respective tracker to the associated object. Any one or more of the trackers 52, 54, 56, PT may include active markers 58. The active markers 58 may include light emitting diodes (LEDs). Alternatively, the trackers 52, 54, 56, PT may have passive markers, such as reflectors, which reflect light emitted from the camera unit 46. Printed markers, or other suitable markers not specifically described herein, may also be utilized.

Various coordinate systems may be employed for purposes of tracking the objects. For instance, the coordinate systems may comprise the localizer coordinate system LCLZ, the tool support coordinate system TCS, the base coordinate system BCS, coordinate systems associated with each of the trackers 52, 54, 56, PT, one or more coordinate systems associated with the anatomy, one or more coordinate systems associated with pre-operative and/or intra-operative images (e.g., CT images, MRI images, etc.) and/or models (e.g., 2D or 3D models) of the anatomy—such as the implant coordinate system, and a TCP (tool center point) coordinate system. In some examples, the robotic system 10 does not rely on pre-operative and/or intraoperative imaging to create the 2D or 3D models of the target bone. Rather, the robotic system may be used in an imageless system using the pointer tracker PT to register the target anatomy, capturing various anatomical landmarks, which is then processed by the control system 60 to morph a nominal bone model to match the captured data. In other examples, pre-operative and intraoperative imaging is used to image the target area of the patient and then transform the 2D and/or 3D images into a 3D model of the target bone. It is also contemplated that the robotic system 10 may use a combination of imaged and imageless procedures in creating a 3D model of the target surgical area. One exemplary system is described in U.S. Pat. No. 8,617,174, which is hereby incorporated by reference. Coordinates in the various coordinate systems may be transformed to other coordinate systems using transformations upon establishing relationships between the coordinate systems, e.g., via registration, calibration, geometric relationships, measuring, etc.

As shown in FIG. 2, in some examples, the TCP is a predetermined reference point or origin of the TCP coordinate system defined at the distal end of the tool 20. The geometry of the tool 20 may be defined relative to the TCP coordinate system and/or relative to the tool support coordinate system TCS. The tool 20 may comprise one or more geometric features, e.g., perimeter, circumference, radius, diameter, width, length, height, volume, area, surface/plane, range of motion envelope (along any one or more axes), etc. defined relative to the TCP coordinate system and/or relative to the tool support coordinate system TCS and stored in the non-volatile memory of the control boards 31 in the control housing 29 of the instrument 14, the navigation system 32, the instrument controller 28, or a combination thereof. The tool center point (TCP), in one example, is a predetermined reference point and corresponding coordinate system defined at the tool 20. The TCP has a known, or able to be calculated (i.e., not necessarily static), pose relative to other coordinate systems. The TCP coordinate system includes an origin point and a set of axes (e.g. x axis, y axis, z axis) which define the pose of the TCP. By tracking the TCP (or knowing the pose of the TCP), the robotic system 10 may calculate the position and orientation of the instrument 14 based on the pose of the TCP and the known positional relationship between the TCP and the features of the instrument 14. In some examples, the tool 20 has a blade plane (e.g., for saw blades) that will be described for convenience and ease of illustration, but is not intended to limit the tool 20 to any particular form. Points, other primitives, meshes, other 3D models, etc., can be used to virtually represent the tool 20. The origin point of the TCP coordinate system may be located at the spherical center of the bur 25 of the tool 20 or at the distal end of the saw blade 27 such that the TCP coordinate system is tracked relative to the origin point on the distal tip of the tool 200. Alternatively, the TCP may be tracked using a plurality of tracked points. The TCP may be defined in various ways depending on the configuration of the tool 20. The instrument may employ the joint/motor encoders, or any other non-encoder position sensing method, so the control system 60 may determine a pose and/or position of the TCP relative to the hand-held portion 16 and BCS. The tool support 18 may use joint measurements to determine TCP pose and/or could employ techniques to measure TCP pose directly. The control of the tool 20 is not limited to a center point. For example, any suitable primitives, meshes, etc., can be used to represent the tool 20. It should be appreciated that the TCP may alternatively be defined as a point, as opposed to a coordinate system. The TCP coordinate system allows calculate any required reference points or geometry aspects of the tool once you have determined the pose of the saw blade or other tool.

The TCP coordinate system, the tool support coordinate system TCS, and the coordinate system of the tool tracker 52 may be defined in various ways depending on the configuration of the tool 20. For example, the pointer 57 may be used with calibration divots CD in the tool support 18 and/or in the tool 20 for: registering (calibrating) a pose of the tool support coordinate system TCS relative to the coordinate system of the tool tracker 52; determining a pose of the TCP coordinate system relative to the coordinate system of the tool tracker 52; and/or determining a pose of the TCP coordinate system relative to the tool support coordinate system TCS. Other techniques could be used to measure the pose of the TCP coordinate system directly, such as by attaching and fixing one or more additional trackers/markers directly to the tool 20. In some versions, trackers/markers may also be attached and fixed to the hand-held portion 16, the tool support 18, or both. In instances where the hand-held portion includes a tracker, the pose of the hand-held portion relative to the localizer coordinate system LCTZ may be measured directly. In still other alternatives, the TCP may be defined relative to the tool tracker, using the intermediate tool support coordinate system TCS.

Since the tool support 18 is movable in multiple degrees of freedom relative to the hand-held portion 16 via the actuators 21, 22, 23, the instrument 14 may employ actuator sensors, such as encoders, hall-effect sensors (with analog or digital output), transducers, and/or any other position sensing method, to measure a pose of the TCP coordinate system and/or tool support coordinate system TCS relative to the base coordinate system BCS. In one exemplary configuration, the instrument 14 may use measurements from actuator sensors that measure actuation of the actuators 21, 22, 23 to determine a pose of the TCP coordinate system and/or tool support coordinate system TCS relative to the base coordinate system BCS, as described further below. As an alternative to the actuator sensors, one or more of the joints of the device may include encoders to determine one or more joint angles. These 'joint sensors' may generate 'joint angles' may be coupled to the controller using one or more flex circuits in a similar manner as the described actuator sensors. The joint angles may facilitate determination of the pose of the TCP coordinate system and the base coordinate system BCS and tool support coordinate system TCS as described with respect to the actuator sensors.

The localizer 44 monitors the trackers 52, 54, 56, PT (e.g., coordinate systems thereof) to determine a state of each of the trackers 52, 54, 56, PT, which correspond respectively to the state of the object respectively attached thereto. The localizer 44 may perform known techniques to determine the states of the trackers 52, 54, 56, PT, and associated objects (such as the tool, the patient, the tool support, and the hand-held portion). The localizer 44 provides the states of the trackers 52, 54, 56, PT to the navigation controller 36. In some examples, the navigation controller 36 determines and communicates the states of the trackers 52, 54, 56, PT to the instrument controller 28 or console.

The navigation controller 36 may comprise one or more computers, or any other suitable form of controller. Navigation controller 36 has a central processing unit (CPU) and/or other processors, memory, and storage (not shown). The processors can be any type of processor, microprocessor or multi-processor system. The navigation controller 36 is loaded with software. The software, for example, converts the signals received from the localizer 44 into data representative of the position and/or orientation of the objects being tracked. The navigation controller 36 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor.

Although one example of the navigation system 32 is shown to determine object states, the navigation system 32 may have any other suitable configuration for tracking the instrument 14, tool 20, and/or the patient 12. In another example, the navigation system 32 and/or localizer 44 are ultrasound-based. For example, the navigation system 32 may comprise an ultrasound imaging device coupled to the navigation controller 36. The ultrasound imaging device images any of the aforementioned objects, e.g., the instrument 14, the tool 20, and/or the patient 12, and generates state signals to the navigation controller 36 based on the ultrasound images. The ultrasound images may be 2D, 3D, or a combination of both. The navigation controller 36 may process the images in near real-time to determine states of the objects. The ultrasound imaging device may have any suitable configuration and may be different than the camera unit 46 as shown in FIG. 1.

In another example, the navigation system 32 and/or localizer 44 are radio frequency (RF)-based. For example, the navigation system 32 may comprise an RF transceiver coupled to the navigation controller 36. The instrument 14, the tool 20, and/or the patient 12 may comprise RF emitters or transponders attached thereto. The RF emitters or transponders may be passive or actively energized. The RF transceiver transmits an RF tracking signal and generates state signals to the navigation controller 36 based on RF signals received from the RF emitters. The navigation controller 36 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52, 54, 56, PT shown in FIG. 1.

In yet another example, the navigation system 32 and/or localizer 44 are electromagnetically based. For example, the navigation system 32 may comprise an EM transceiver coupled to the navigation controller 36. The instrument 14, the tool 20, and/or the patient 12 may comprise EM components attached thereto, such as any suitable magnetic tracker, electro-magnetic tracker, inductive tracker, or the like. The trackers may be passive or actively energized. The EM transceiver generates an EM field and generates state signals to the navigation controller 36 based upon EM signals received from the trackers. The navigation controller 36 may analyze the received EM signals to associate relative states thereto. Again, such navigation system 32 examples may have structural configurations that are different than the navigation system 32 configuration shown in FIG. 1.

The navigation system 32 may have any other suitable components or structure not specifically recited herein. Furthermore, any of the techniques, methods, and/or components described above with respect to the navigation system 32 shown may be implemented or provided for any of the other examples of the navigation system 32 described herein. For example, the navigation system 32 may utilize solely inertial tracking or any combination of tracking techniques, and may additionally or alternatively comprise, fiber optic-based tracking, machine-vision tracking, and the like.

Referring to FIG. 7, the robotic system 10 includes a control system 29, 60 that comprises, among other components, the instrument controller 28 and the navigation controller 36. The control system 60 further includes one or more software programs and software modules. The software modules may be part of the program or programs that operate on the instrument controller 28, navigation controller 36, or a combination thereof, to process data to assist with control of the robotic system 10. The software programs and/or modules include computer readable instructions stored in memory 64 on the instrument controller 28, navigation controller 36, or a combination thereof, to be executed by one or more processors 70 of the controller 28. The memory 64 may be any suitable configuration of memory, such as non-transitory memory, RAM, non-volatile memory, etc., and may be implemented locally or from a remote database. Additionally, software modules for prompting and/or communicating with the user may form part of the program or programs and may include instructions stored in memory 64 on the instrument controller 28, navigation controller 36, or a combination thereof. The user may interact with any of the input devices of the navigation user interface UI or other user interface UI to communicate with the software modules. The user interface software may run on a separate device from the instrument controller 28 and/or navigation controller 36. The instrument 14 may communicate with the instrument controller 28 via a power/data connection. The power/data connection may provide a path for the input and output used to control the instrument 14 based on the position and orientation data generated by the navigation system 32 and transmitted to the instrument controller 28, as shown as the BUS/COMM connection 37 in FIG. 7. It is contemplated that each of the processing steps described throughout may be performed on the console, the instrument controller, or the navigation controller or may be distributed through each of these possible locations. In still further configurations, any of the processing described throughout could be provided at other locations, such as on a remote server.

The control system 60 may comprise any suitable configuration of input, output, and processing devices suitable for carrying out the functions and methods described herein. The control system 60 may comprise the instrument controller 28, the navigation controller 36, or a combination thereof, and/or may comprise only one of these controllers, or additional controllers. The controllers may communicate via a wired bus or communication network as shown in one example as the BUS/COMM connection 37 in FIG. 7, via wireless communication, or otherwise. The control system 60 may also be referred to as a controller. The control system 60 may comprise one or more microcontrollers, field programmable gate arrays, systems on a chip, discrete circuitry, sensors, displays, user interfaces, indicators, and/or other suitable hardware, software, or firmware that is capable of carrying out the functions described herein.

Instrument

Figure 8:
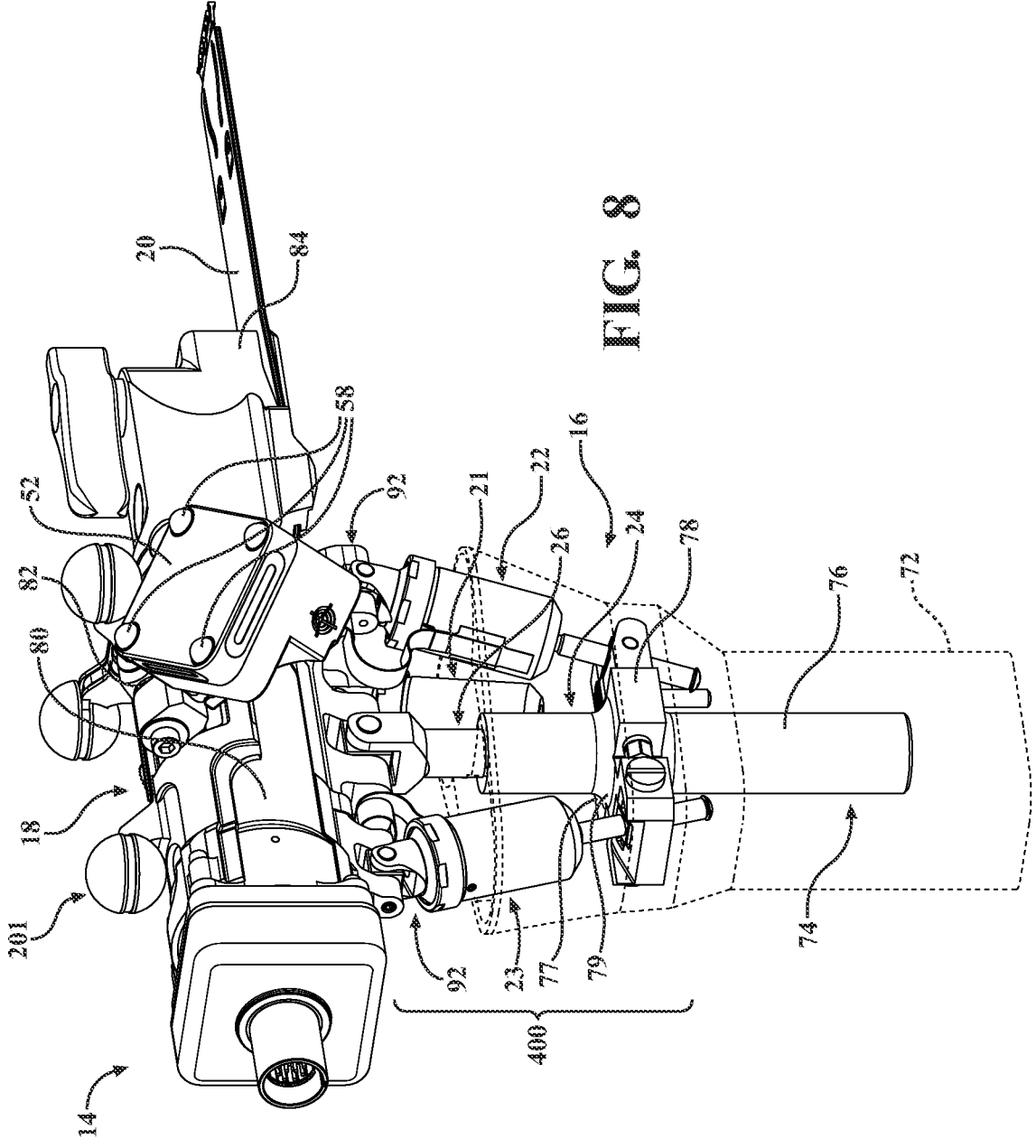
FIG. 8 is a rear perspective view of the robotic instrument.
Figure 9:
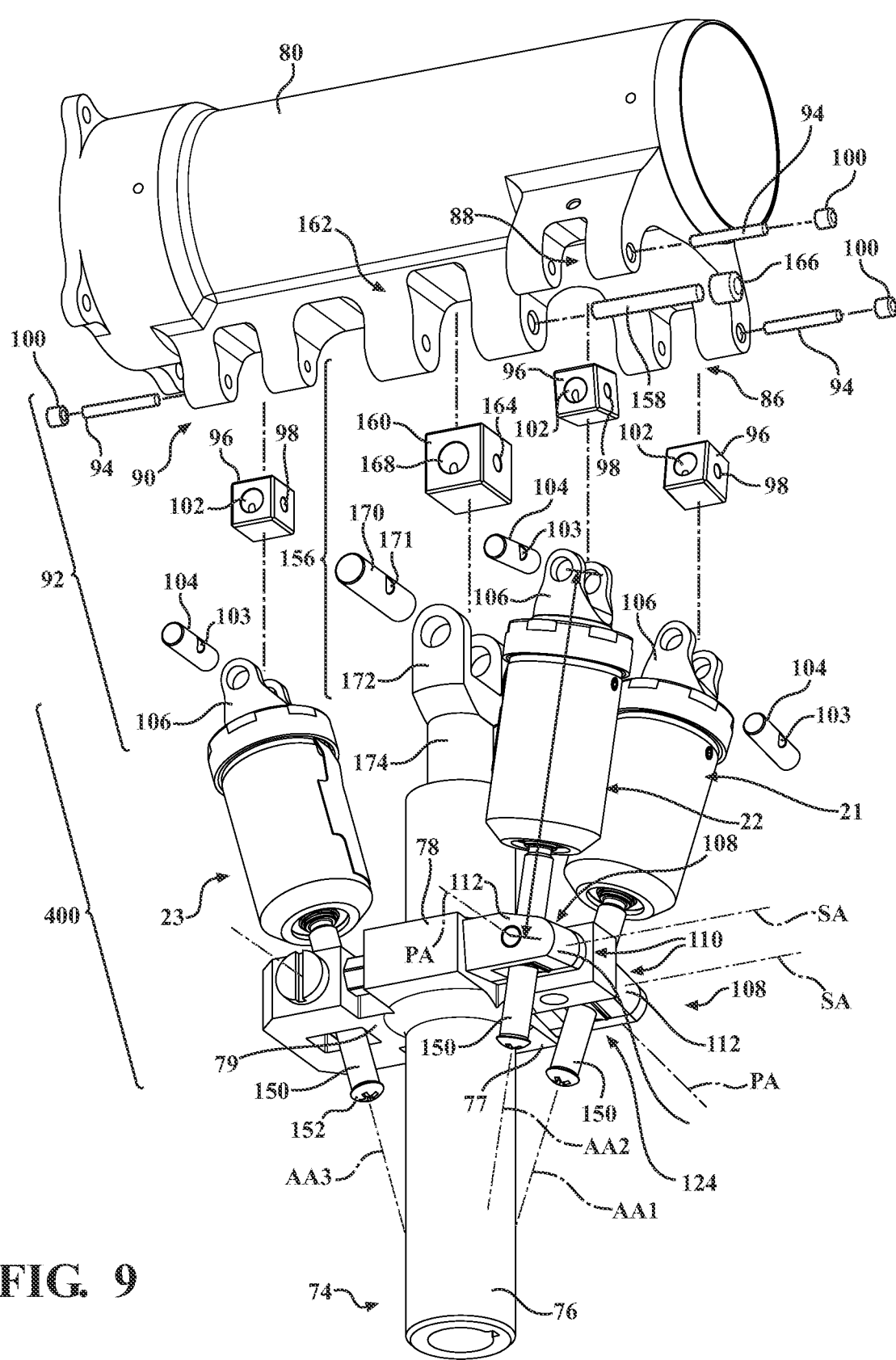
FIG. 9 is an exploded view showing a body of the tool support and associated joint connections to a plurality of actuators.
Figure 10:
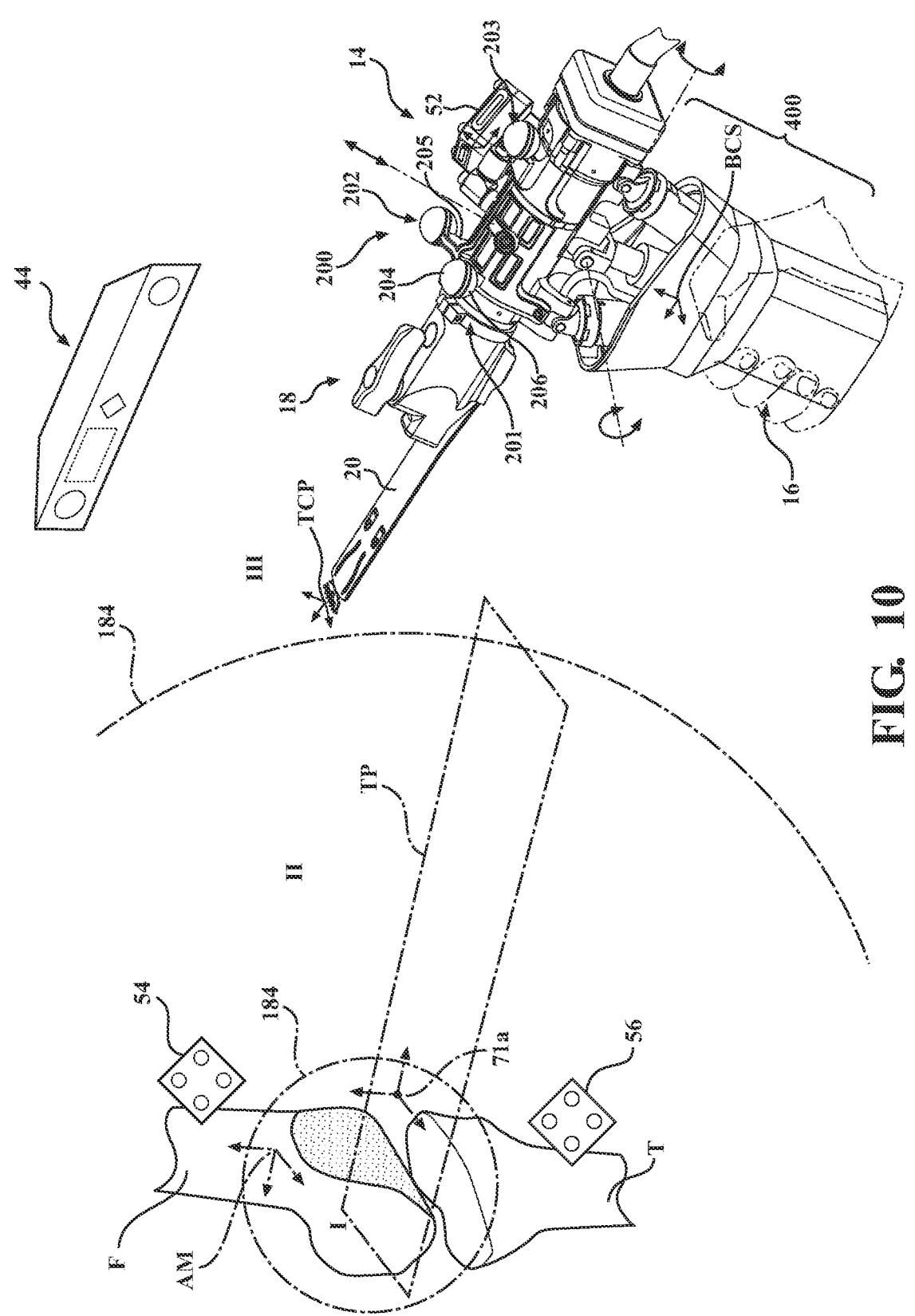
FIG. 10 illustrates various regions in which the robotic instrument is used.

In one exemplary configuration, the instrument 14 is best shown in FIGS. 8 and 9. The instrument 14 includes the hand-held portion 16 to be held by the user, the tool support 18 movably coupled to the hand-held portion 16 to support the tool 20, the actuator assembly 400 with the plurality of actuators 21, 22, 23 operatively interconnecting the tool support 18 and the hand-held portion 16 to move the tool support 18 in at least three degrees of freedom relative to the hand-held portion 16, and the constraint assembly 24 having the linkage 26 operatively interconnecting the tool support 18 and the hand-held portion 16. In some cases, the linkage 26 is referred to as a passive linkage, but is not necessarily passive in all contemplated configurations.

The hand-held portion 16 comprises a grip 72 for being grasped by the user so that the user is able to manipulate, guide, and/or grasp the instrument 14. The hand-held portion 16 may be configured with ergonomic features such as a grip for a hand of a user to hold, a textured or mixed material coating for preventing a user's hand from slipping when wet and/or bloody. The hand-held portion 16 may include a taper to accommodate users with different hand sizes and contoured to mate with the contours of a user's hand and/or fingers. The hand-held portion 16 also comprises a base 74 to which the grip 72 is attached by one or more fasteners, adhesive, welding, or the like. In the version shown, the base 74 comprises a sleeve 76 having a generally hollow cylindrical shape. Joint supports 77, 78, 79 extend from the sleeve 76. The actuators 21, 22, 23 may be movably coupled to the base 74 at the joint supports 77, 78, 79 via joints described further below.

The tool support 18 comprises a tool support body 80 to which the tool tracker 52 can be fixed to or removably mounted via one or more tracker mounts fixed to the tool support 18 at one or more mounting locations 82. In one example, the tool tracker 52 is integrated with the tool support 18. In another example, the tool tracker 52 is removably mounted at the one or more mounting locations 82. The tool 20 is removably coupled to the tool support 18 in the version shown. In particular, the tool support 18 comprises a tool coupler, such as head 84 to which the tool 20 is mounted, as described in U.S. Pat. No. 9,820,753 to Walen et al., incorporated herein by reference. The head 84 may be configured to utilize an oscillating-style of saw blade, as well as a sagittal-style saw blade. The drive motor DM that drives operation of the tool 20 is disposed in the tool support body 80 (e.g., to drive oscillation of the saw blade in some versions). The tool 20 may be attached to and released from the head 84 in the manner disclosed in U.S. Pat. No. 9,820,753 to Walen et al., incorporated herein by reference. As best shown in FIG. 9, the tool support 18 also comprises a plurality of actuator mounts 86, 88, 90 at which the actuators 21, 22, 23 are to be movably coupled to the tool support 18 via joints, as described further below. The actuator mounts 86, 88, 90 may comprise brackets, or the like, suitable to mount the actuators 21, 22, 23 such that the tool support 18 is able to move in at least three degrees of freedom relative to the hand-held portion 16.

The actuators 21, 22, 23, in the version shown, comprise electric, linear actuators that extend between the base 74 and the tool support body 80. When actuated, an effective length of the actuator 21, 22, 23 changes to vary a distance between the tool support body 80 and the base 74 along a corresponding axis of the actuator 21, 22, 23. Accordingly, the control system 60 commands the actuators 21, 22, 23 to work in a coordinated fashion, responding to individual inputs given to each actuator 21, 22, 23, respectively, by the control system 60 to change their effective lengths and move the tool support 18 in at least three degrees of freedom relative to the hand-held portion 16 into the target pose. In the version shown, three actuators 21, 22, 23 are provided, and may be referred to as first, second, and third actuators 21, 22, 23 or front actuators 21, 22, and rear actuator 23. The first, second, and third actuators 21, 22, 23 are adjustable in effective length along a first active axis AA1, a second active axis AA2, and a third active axis AA3 (see FIG. 9). The first, second, and third actuators 21, 22, 23 are independently adjustable in effective length to adjust one or more of a pitch orientation, a roll orientation, and a z-axis translation position of the tool support 18 relative to the hand-held portion 16, as previously described. More actuators may be provided in some examples. The actuators may comprise rotary actuators in some examples. The actuators 21, 22, 23 may comprise linkages having one or more links of any suitable size or shape. The actuators 21, 22, 23 may have any configuration suitable to enable movement of the tool support 18 relative to the hand-held portion 16 in two or more degrees of freedom. For example, in some versions, there may be one front actuator and two rear actuators, or some other arrangement of actuators.

In this version, the actuators 21, 22, 23 are coupled to the base 74 and the tool support body 80 via a plurality of active joints. The active joints include a set of first active joints 92 that couple the actuators 21, 22, 23 to the tool support body 80 at the actuator mounts 86, 88, 90. In one version, as shown in FIG. 9, the first active joints 92 comprises active U-joints. The U-joints comprise first pivot pins 94 and joint blocks 96. The first pivot pins 94 pivotally connect the joint blocks 96 to the actuator mounts 86, 88, 90 via throughbores 98 in the joint blocks 96. Set screws 100 may secure the first pivot pins 94 to the actuator mounts 86, 88, 90. The U-joints may also comprise second pivot pins 104. The joint blocks 96 have crossbores 102 to receive the second pivot pins 104. The second pivot pins 104 have throughbores 103 to receive the first pivot pins 94, such that the first pivot pins 94, the joint blocks 96, and the second pivot pins 104 form a cross of the U-joint. The first pivot pin 94 and the second pivot pin 104 of each U-joint define pivot axes PA that intersect. The second pivot pins 104 pivotally connect a pivot yoke 106 of the actuators 21, 22, 23 to the joint blocks 96. As a result, the actuators 21, 22, 23 are able to move in two degrees of freedom relative to the tool support body 80. Other types of active joints are also contemplated, such as active spherical joints comprising balls with slots that receive pins.

Referring to FIG. 9, the active joints also comprise a set of second active joints 108 coupling the front two actuators 21, 22 to the base 74 of the hand-held portion 16. In the version shown, the second active joints 108 are supported at the joint supports 77, 78. Each of the second active joints 108 comprises a swivel yoke 110 arranged to swivel relative to the base 74 of the hand-held portion 16 about a swivel axis SA. Each swivel yoke 110 has a swivel head 112 and a post 114 extending from the swivel head 112 to pivotally engage the base 74 at one of the joint supports 77, 78. Nuts 115 threadably connect to one end of the posts 114 to trap the posts 114 in the base 74 while allowing the respective swivel yoke 110 to freely rotate within its respective joint support 77, 78.

Each of the second active joints 108 comprises a carrier 116 pivotally coupled to one of the swivel yokes 110. The carriers 116 have internally threaded throughbores 117 to receive lead screws 150 of the front two actuators 21, 22, as described further below. Each of the carriers 116 also comprises opposed trunnions 118 that allow the carriers 116 to pivot relative to the swivel yokes 110 about pivot axes PA (see FIG. 9) by being seated in pockets in the swivel yokes 110. In some versions, for each of the second active joints 108, the swivel axis SA intersects the pivot axis PA to define a single vertex about which the actuators 21, 22 move in two degrees of freedom.

Covers are fastened to the swivel heads 112 and define one of the pockets, while the swivel head 112 defines the other pocket. During assembly, the carriers are first positioned with one of the trunnions placed in the pocket in the swivel head 112, and the cover is then fastened over the other trunnion such that the carrier is captured between the cover and the swivel head 112 and is able to pivot relative to the swivel yoke 110 via the trunnions and pockets. Owing to the configuration of the swivel yokes 110 and the associated carriers, i.e., the carriers ability to swivel about the swivel axes SA and pivot about the pivot axes PA, the second active joints 108 allow two degrees of freedom of movement of the front two actuators 21, 22 relative to the base 74. Other joint arrangements between the front two actuators 21, 22 and the base 74 are also possible.

The active joints also comprise a third active joint 124 coupling the rear (third) actuator 23 to the base 74 of the hand-held portion 16. In the version shown, the third active joint 124 is supported at the joint support 79. The third active joint 124 comprises a pivot housing 126 fixed to the joint support 79 of the base 74.

The third active joint 124 comprises a carrier pivotally coupled to the pivot housing 126 via trunnions. Fasteners having pockets attach to either side of the pivot housing 126 via throughbores to engage the trunnions. The fasteners are arranged such that the carrier is able to pivot via the trunnions being located in the pockets after assembly. The carrier has an internally threaded throughbore to receive a lead screw 150 of the rear actuator 23, as described further below. Owing to the configuration of the pivot housing 126 and associated carrier, i.e., the ability of the associated carrier to only pivot about the pivot axis PA (e.g., and not swivel), the third active joint 124 allows only one degree of freedom of movement of the rear actuator 23 relative to the base 74. Other joint arrangements between the rear actuator 23 and the base 74 are also possible.

Figure 11:
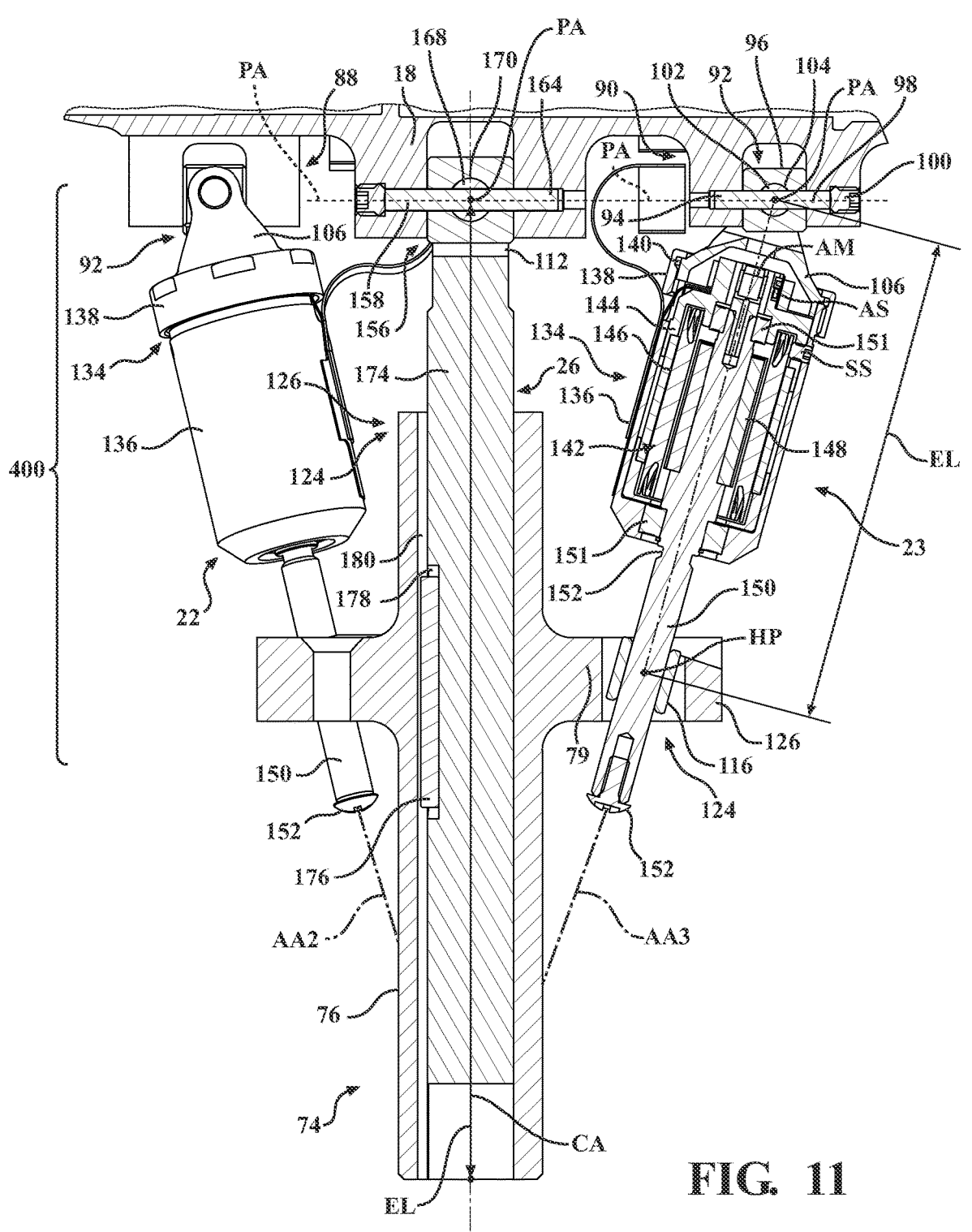
FIG. 11 is a partial cross-sectional view of the instrument.

Referring to FIG. 11, each of the actuators 21, 22, 23 comprises a housing 134. The housing 134 comprises a canister 136 and a cap 138 threadably connected to the canister 136. The pivot yokes 106 that form part of the first active joints 92 are fixed to the housings 134 such that the housings 134 and pivot yokes 106 are able to move together relative to the tool support 18 via the first active joints 92. The caps 138 capture annular shoulders 140 of the pivot yokes 106 to secure the pivot yokes 106 to the canisters 136.

In some versions, the pivot yokes 106 and canisters 136 comprise one or more alignment features to align each pivot yoke 106 to its respective canister 136 in a predefined, relative orientation. Such alignment features may comprise mating portions, keys/keyways, or the like. During assembly, the pivot yoke 106 may first be secured to the canister 136 in its predefined, relative orientation, and the cap 138 may then be threaded onto the canister 136 (e.g., via mating outer and inner threads) to trap the pivot yoke 106 to the canister 136 at the predefined, relative orientation. This predefined relationship may be helpful in routing and/or aligning the flexible circuits FC, preventing rolling of the pivot yoke 106 relative to the canister 136, and/or for other purposes.

Each of the actuators 21, 22, 23 also comprises an actuator motor 142 disposed in each housing 134. The actuator motor 142 has a casing 144 disposed in the housing 134 and a motor winding assembly 146 disposed within the casing 144. The motor winding assembly 146 may also be aligned in a predefined, relative orientation to the canister 136, such as via a set screw SS (see FIG. 11) or other alignment feature, such as those described above. Each actuator motor 142 also has a rotor 148 fixed to the lead screw 150. The lead screw 150 is supported for rotation in the housing 134 by one or more bushings and/or bearings 151. The rotor 148 and associated lead screw 150 are configured to rotate relative to the housing 134 upon selective energization of the actuator motor 142. The lead screws 150 have fine pitch and lead angles to prevent backdriving (i.e., they are self-locking). As a result, a load placed on the tool 20 does not easily back drive the actuator motor 142. In some examples, the lead screws 150 have an 8-36 class 3 thread that results in a lead of from 0.02 to 0.03 inches/revolution. Other thread types/sizes may also be employed.

Each of the actuators 21, 22, 23 may be controlled by a separate motor controller. Motor controllers may be wired separately to the actuators 21, 22, 23, respectively, to individually direct each actuator 21, 22, 23 to a given target position. In some examples, the motor controllers are proportional integral derivative (PID) controllers. In some examples, the motor controllers can be integrated with or form part of the instrument controller 28. For ease of illustration, the motor controllers shall be described herein as being part of the instrument controller 28.

A power source provides, for example, 32 VDC power signals to the actuator motors 142 via the console 33. The 32 VDC signal is applied to the actuator motors 142 through the instrument controller 28. The instrument controller 28 selectively provides the power signal to each actuator motor 142 to selectively activate the actuator motors 142. This selective activation of the actuator motors 142 is what positions the tool 20. The actuator motors 142 may be any suitable type of motor, including brushless DC servomotors, other forms of DC motors, or the like. The power source also supplies power to the instrument controller 28 to energize the components internal to the instrument controller 28. It should be appreciated that the power source can provide other types of power signals such as, for example, 12 VDC, 24 VDC, 40 VDC, etc.

One or more actuator sensors AS (see FIG. 11) transmit signals back to the instrument controller 28 so that the instrument controller 28 can determine a current position of the associated actuator 21, 22, 23 (i.e., a measured position), or this could be done at the console 33. The one or more sensors AS may be position sensors. The levels of these signals may vary as a function of the rotational position of the associated rotor 148. In one implementation, the actuator sensor(s) AS may resolve the rotational position of the rotor 148 within a given turn at a high resolution. These actuator sensors AS may be Hall-effect sensors that output analog and/or digital signals based on the sensed magnetic fields from the rotor 148, or from other magnets placed on the lead screw 150 (see, e.g., the 2-pole magnet AM in FIG. 11). A low voltage signal, e.g., 5 VDC, for energizing the Hall-effect sensors may be supplied from the motor controller associated with the actuator motor 142 with which the Hall-effect sensors are associated. In some examples, two Hall-effect sensors are disposed in the housing 134 and spaced 90 degrees apart from each other around the rotor 148 to sense rotor position so that the instrument controller 28 or the console is able to determine the position and count incremental turns of the rotor 148 (one such actuator sensor AS and actuator magnets AM are shown in FIG. 11). In some versions, the Hall-effect sensors output digital signals representing incremental counts. Various types of motors and sensor arrangements are possible. In some examples, the actuator motors 142 are brushless DC servomotors and two or more internal Hall-effect sensors may be spaced 90 degrees, 120 degrees, or any other suitable spacing from each other around the rotor 148. The actuator sensors AS may also comprise absolute or incremental encoders, which may be used to detect a rotational position of the rotor 148 and to count turns of the rotor 148. Other type of encoders may be also used as the one or more sensors. The sensors may be placed at any suitable location on the actuator and its surrounding components suitable to determine the position of each actuator as it is adjusted, such as on the housing, nut, screw, etc. In yet another configuration, sensorless motor control may be utilized. In such an implementation, the position of each rotor may be determined by measuring the motor's back-emf and/or inductance. One suitable example may be found in U.S. Pat. No. 7,422,582, which is hereby incorporated by reference in its entirety.

In some examples, output signals from the Hall-effect sensors are sent to the instrument controller 28 or console. The instrument controller 28 monitors the received signals for changes in their levels. Based on these signals the instrument controller 28 determines rotor position. Rotor position may be considered the degrees of rotation of the rotor 148 from an initial or home position. The rotor 148 can undergo plural 360° rotations. The rotor position can therefore exceed 360°. A scalar value referred to as a count is representative of rotor position from the home position. The rotors 148 rotate in both clockwise and counterclockwise directions. Each time the signal levels of the plural signals (analog or digital) undergo a defined state change, the instrument controller 28 increments or decrements the count to indicate a change in rotor position. For every complete 360° rotation of the rotor 148, the instrument controller 28 increments or decrements the value of the count by a fixed number of counts. In some examples, the count is incremented or decremented between 100 and 3,000 per 360-degree revolution of the rotor 148. In some examples, there are 1,024 positions (counts) per 360-degree revolution of the rotor 148, such as when an incremental encoder is used to monitor rotor position. Internal to the instrument controller 28 is a counter associated with each actuator 21, 22, 23. The counter stores a value equal to the cumulative number of counts incremented or decremented. The count value can be positive, zero or negative. In some versions, the count value defines incremental movement of the rotor 148. Accordingly, the rotors 148 of the actuators 21, 22, 23 may first be moved to known positions, referred to as their home positions (described further below), with the count values being used thereafter to define the current positions of the rotors 148.

As previously described, the carriers 116 have the internally threaded throughbores 117 to threadably receive the lead screws 150 so that each of the lead screws 150 can rotate relative to a corresponding one of the carriers 116 to adjust the effective length of a corresponding one of the plurality of actuators 21, 22, 23 and thereby vary the counts measured by the instrument controller 28. Each of the housings 134 and corresponding carriers 116 are constrained from relative movement in at least one degree of freedom to allow the lead screws 150 to rotate relative to the carriers 116. More specifically, the lead screws 150 are able to rotate relative to the carriers 116 owing to: the pivot yokes 106 being unable to rotate about the associated active axes AA1, AA2, AA3 (i.e., the pivot yokes 106 are limited from such rotational movement by virtue of the configuration of the first active joints 92); and the carriers 116 being unable to rotate about the associated active axes AA1, AA2, AA3 (i.e., the carriers 116 are limited from such rotational movement by virtue of the configuration of the second active joints 108 and the third active joint 124).

Stops 152, such as threaded fasteners and shoulders formed on the lead screws 150, are fixed to the lead screws 150. The stops 152 are sized to abut the carriers 116 at ends of travel of each lead screw 150.

As previously described, the actuators 21, 22, 23 are actively adjustable in effective length to enable movement of the tool support 18 relative to the hand-held portion 16. One example of this effective length is labeled "EL" on the third actuator 23 in FIG. 11. Here, the effective length EL is measured from a center of the associated carrier 116 to a center of the associated first active joint 92. As each actuator 21, 22, 23 is adjusted, the effective length EL changes, by varying how far the lead screw 150 has been threaded into or out of its associated carrier 116 and thereby changing the distance from the center of the associated carrier 116 to the center of the associated first active joint 92. The actuators 21, 22, 23 are adjustable between minimum and maximum values of the effective length EL. The effective length EL of each actuator 21, 22, 23 can be represented/measured in any suitable manner to denote the distance between the tool support 18 and the hand-held portion 16 along the active axes AA1, AA2, AA3 that changes to cause various movements of the tool support 18 relative to the hand-held portion 16.

The constraint assembly 24 works in concert with the actuators 21, 22, 23 to constrain the movement provided by the actuators 21, 22, 23. The actuators 21, 22, 23 provide movement in three degrees of freedom, while the constraint assembly 24 constrains movement in three degrees of freedom. In the version shown, the constraint assembly 24 comprises the passive linkage 26, as well as a passive linkage joint 156 that couples the passive linkage 26 to the tool support 18.

Figures 14, 15:
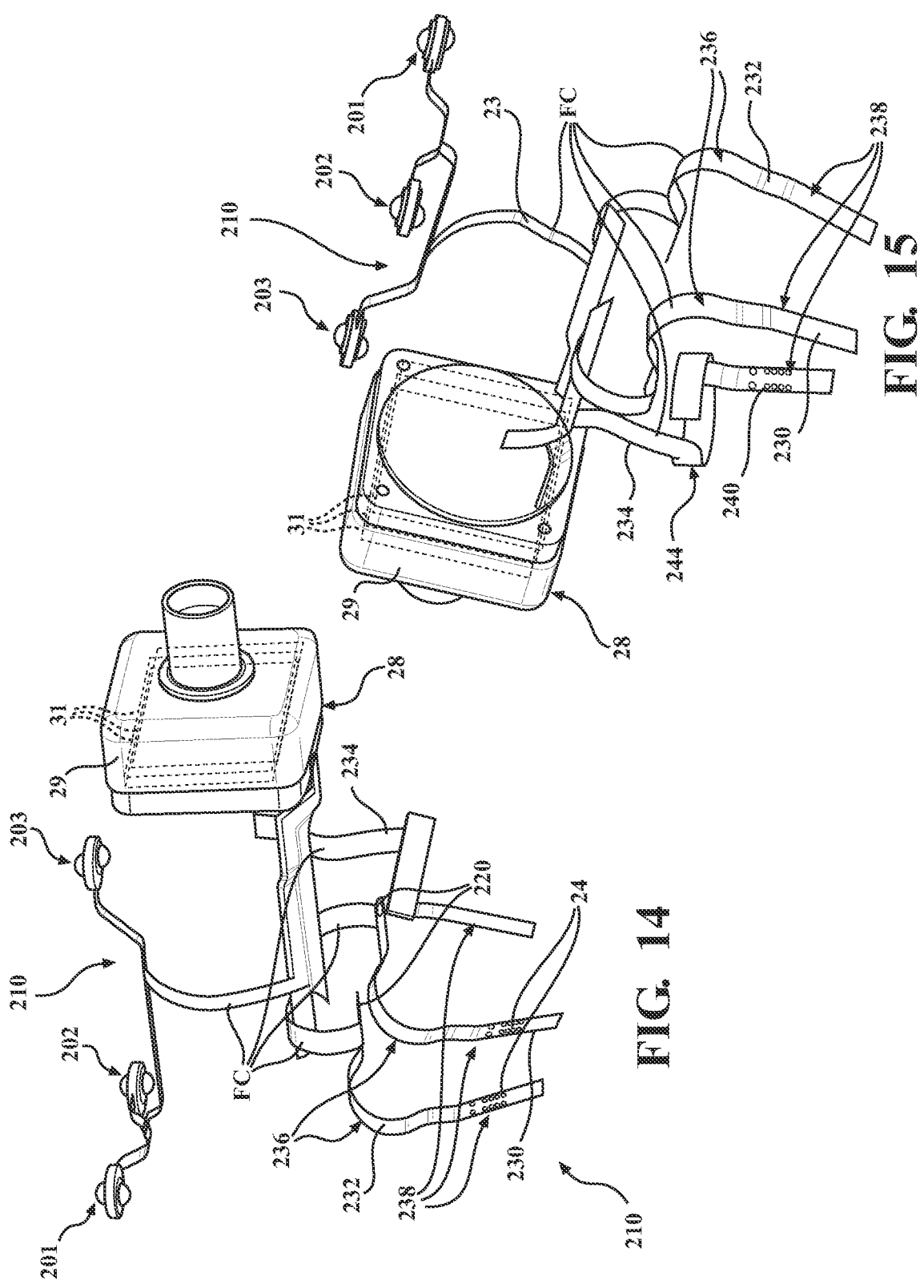
FIGS. 14 and 15 are perspective views of the flexible circuits from the robotic instrument of FIGS. 12 and 13.
Figure 16:
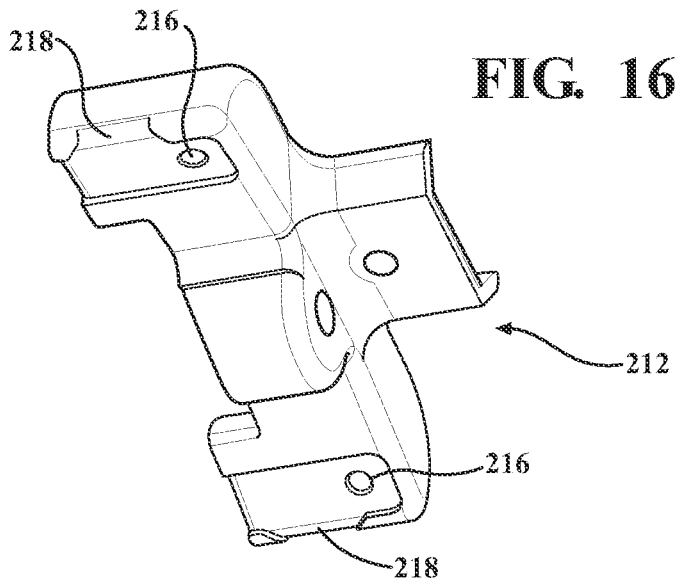
FIG. 16 is a perspective view of a flexible circuit support.

In one version, as shown in FIGS. 14 and 16, the passive linkage joint 156 comprises a passive linkage U-joint. The U-joint comprises a first pivot pin 158 and a joint block 160. The first pivot pin 158 pivotally connects the joint block 160 to a passive linkage mount 162 of the tool support body 80 via a throughbore 164 in the joint block 160. A set screw 166 may secure the first pivot pin 158 to the passive linkage mount 162. The U-joint also comprises a second pivot pin 170. The joint block 160 has a crossbore 168 to receive the second pivot pin 170. The second pivot pin 170 pivotally connects a passive linkage pivot yoke 172 of the passive linkage 26 to the joint block 160. The second pivot pin 170 has a throughbore 171 to receive the first pivot pin 158, such that the first pivot pin 158, the joint block 160, and the second pivot pin 170 form a cross of the U-joint. The first pivot pin 158 and the second pivot pin 170 define pivot axes PA that intersect (see FIG. 11). As a result, the passive linkage 26 is able to move in two degrees of freedom relative to the tool support body 80. Other types of passive linkage joints are also contemplated, such as a passive linkage spherical joint 107 comprising a ball with slot that receives a pin (see, e.g., FIGS. 20 and 21).

The passive linkage 26 comprises a shaft 174 fixed to the passive linkage pivot yoke 172. The passive linkage 26 also comprises the sleeve 76 of the base 74, which is configured to receive the shaft 174 along a constraint axis CA. The passive linkage 26 is configured to allow the shaft 174 to slide axially along the constraint axis CA relative to the sleeve 76 and to constrain movement of the shaft 174 radially relative to the constraint axis CA during actuation of one or more of the actuators 21, 22, 23.

The passive linkage 26 further comprises a key 176 to constrain rotation of the shaft 174 relative to the sleeve 76 about the constraint axis CA. The key 176 is best shown in FIG. 11. The key 176 fits in opposing keyways 178, 180 in the shaft 174 and sleeve 76 to rotationally lock the shaft 174 to the sleeve 76. Other arrangements for preventing relative rotation of the shaft 174 and sleeve 76 are also contemplated, such as an integral key/slot arrangement, or the like. The passive linkage 26 operatively interconnects the tool support 18 and the hand-held portion 16 independently of the actuators 21, 22, 23. The passive linkage is passively adjustable in effective length EL along the constraint axis CA during actuation of one or more of the actuators 21, 22, 23. The sleeve 76, shaft 174, and key 176 represent one combination of links for the passive linkage 26. Other sizes, shapes, and numbers of links, connected in any suitable manner, may be employed for the passive linkage 26.

In the version shown, the passive linkage joint 156 is able to pivot about two pivot axes PA relative to the tool support 18. Other configurations are possible.

Also, in the version shown, the first active joints 92 and the passive linkage joint 156 define pivot axes PA disposed on a common plane. Non-parallel pivot axes PA, parallel pivot axes PA disposed on different planes, combinations thereof, and/or other configurations, are also contemplated.

In some versions, the head 84 of the tool support 18 is arranged so that the tool 20 is located on a tool plane TP (e.g., blade plane) parallel to the common plane when the tool 20 is coupled to the tool support 18. In some examples, the tool plane TP is spaced from the common plane CP by 2.0 inches or less, 1.0 inches or less, 0.8 inches or less, or 0.5 inches or less.

In the version shown, the actuators 21, 22, 23 are arranged such that the active axes AA1, AA2, AA3 are in a canted configuration relative to the constraint axis CA in all positions of the actuators 21, 22, 23, including when in their home positions. Canting the axes AA1, AA2, AA3 generally tapers the actuator arrangement in a manner that allows for a slimmer and more compact base 74 and associated grip 72. Other configurations are contemplated, including those in which the active axes AA1, AA2, AA3 are not in the canted configuration relative to the constraint axis CA. Such configurations may include those in which the actuator axes AA1, AA2, AA3 are parallel to each other in their home positions.

Further configurations of the actuators, active joints, and constraint assembly are possible. It is contemplated that the control techniques described may be applied to other mechanical configurations not mentioned, in particular those for controlling a tool or saw blade relative to a hand-held portion in one or more degrees of freedom. In some versions, the constraint assembly may be absent and the tool support 18 of the instrument 14 may be able to move in additional degrees of freedom relative to the hand-held portion 16. For example, the instrument may include linear actuators, rotary actuators, or combinations thereof. The instrument may include 2, 3, 4, 5, 6 or more different actuators arranged parallel or in series.

Flexible Circuits

Figures 12, 13:
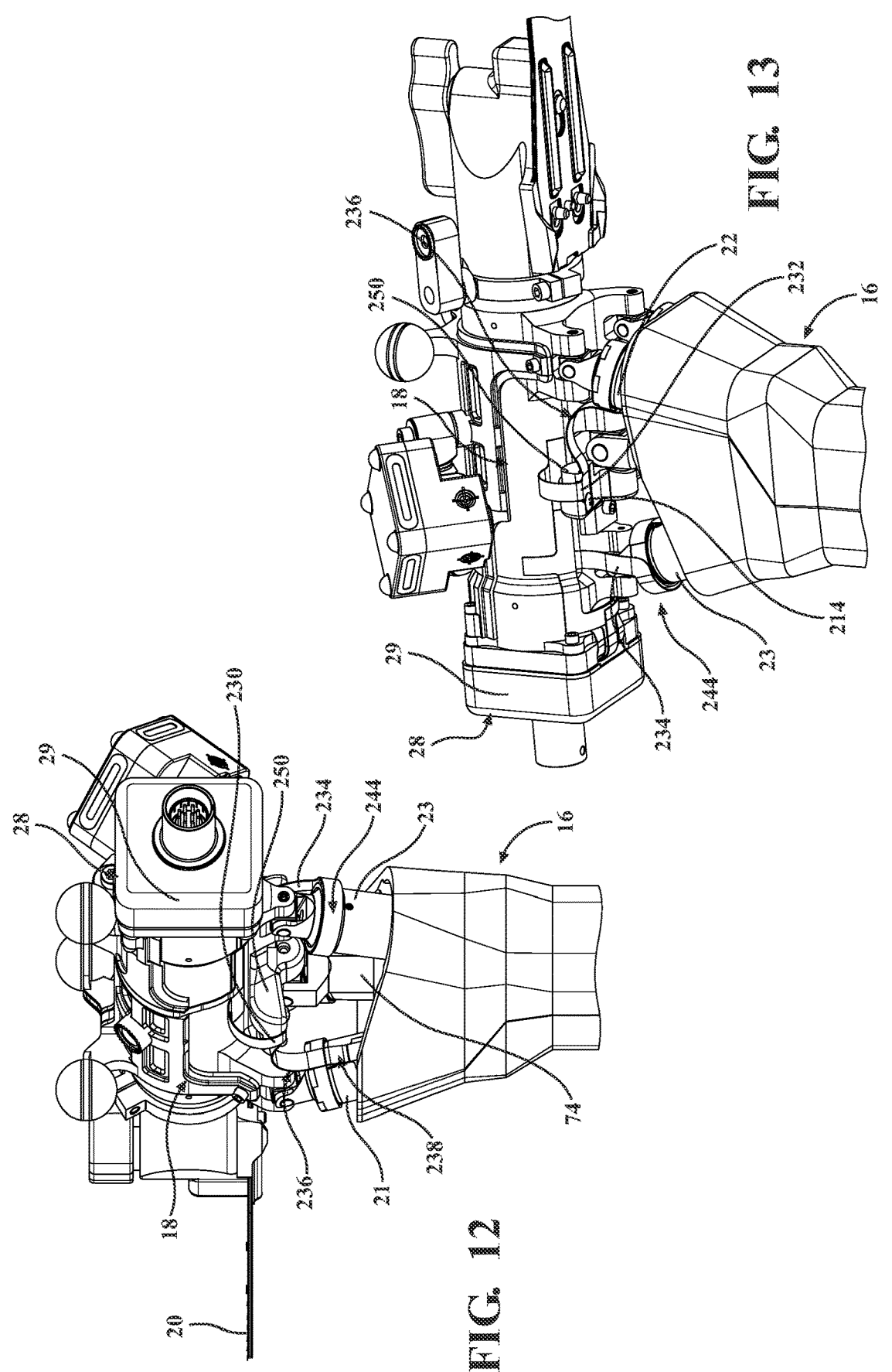
FIGS. 12 and 13 are perspective views of the robotic instrument with flexible circuits assemblies.

As noted above the flexible circuits FC interconnect the actuators 21, 22, 23 and/or other components with the instrument controller 28. For example, FIGS. 12 and 13 are shown with flexible circuits FC provided between the actuators 21, 22, 23, and the control boards 31 in the control housing 29. As noted above, the control boards 31 are connected with and are a part of the instrument controller 28. The flexible circuits FC are configured to be flexible in order to maintain the connection between the actuators 21, 22, 23 and the control boards 31 as the tool support 18 is moved in a plurality of degrees of freedom relative to the hand-held portion 16.

Routing of the flexible circuits FC, in one example, is shown in FIGS. 12-18. FIGS. 14 and 15 show the flexible circuits FC and the control housing 29 (holding control boards 31) isolated from the remainder of the instrument 14. As shown in FIGS. 14 and 15, the flexible circuits FC form part of a flexible circuit assembly 210. The flexible circuit assembly 210 may comprise multiple flexible elongated portions (or legs) formed in one-piece or formed as separate portions that may be attached together. The flexible elongated portions may comprise one or more flexible plastic substrates, such as polyimide, transparent conductive polyester film, or the like.

The flexible circuit assembly 210 comprises conductors mounted and/or embedded in the flexible plastic substrates. The flexible circuits FC may include one or more conductors for transmitting data and/or power between the visual indicators 201, 202, 203, and the instrument controller. The flexible circuits may also comprise one or more conductors for transmitting data and/or power between the actuators 21, 22, 23, and the instrument controller 28. In particular, the flexible elongated portions form the actuator flexible circuits 230, 232, 234. As can be seen in FIGS. 14 and 15, circuit leads 240 are disposed on the ends of the actuator flexible circuits 230, 232, 234 for connecting to the actuators 21, 22, 23, respectively. The actuator flexible circuits 230, 232, 234 may include conductors for transferring power to the actuator motor 142 of the respective actuator 21, 22, 23 from the instrument controller 28. The actuator flexible circuits 230, 232, 234 may also comprise one or more conductors for transmitting data and/or power between the actuator sensors AS and the instrument controller 28. Furthermore, the flexible circuits may include one or more conductors for transmitting data and/or power between an input device, such as a trigger (described further below) and the instrument controller 28.

Each flexible circuit may each independently exhibit a distinct thickness and a width. The dimensions of each flexible circuit may be the same or different from one another. In some examples, the width of each flexible circuit FC is much greater than the thickness of the flexible circuit FC. The width may be at least three times greater, at least five times greater, at least eight times greater, or even at least ten times greater than the thickness of the flexible circuit. The ratio of the thickness to the width of the flexible circuit leads to a tendency towards bending along a length of the flexible circuit, as opposed to bending along the width of the flexible circuit. Additionally, the thickness to width ratio may provide a tendency toward rotating and/or twisting about a z-axis.

Figure 17:
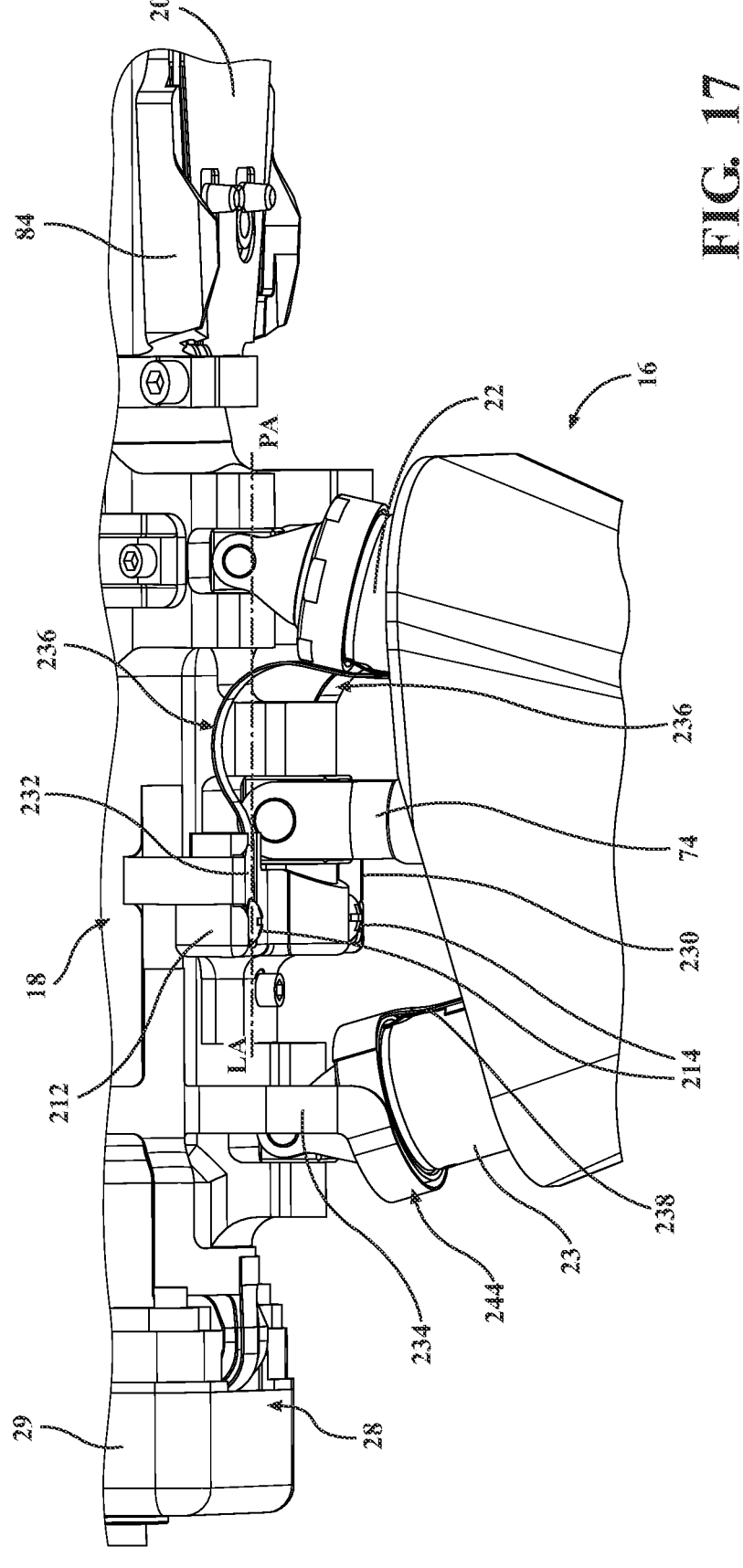
FIG. 17 is a side view of the flexible circuit assembly arranged on the robotic instrument.
Figures 18, 19:
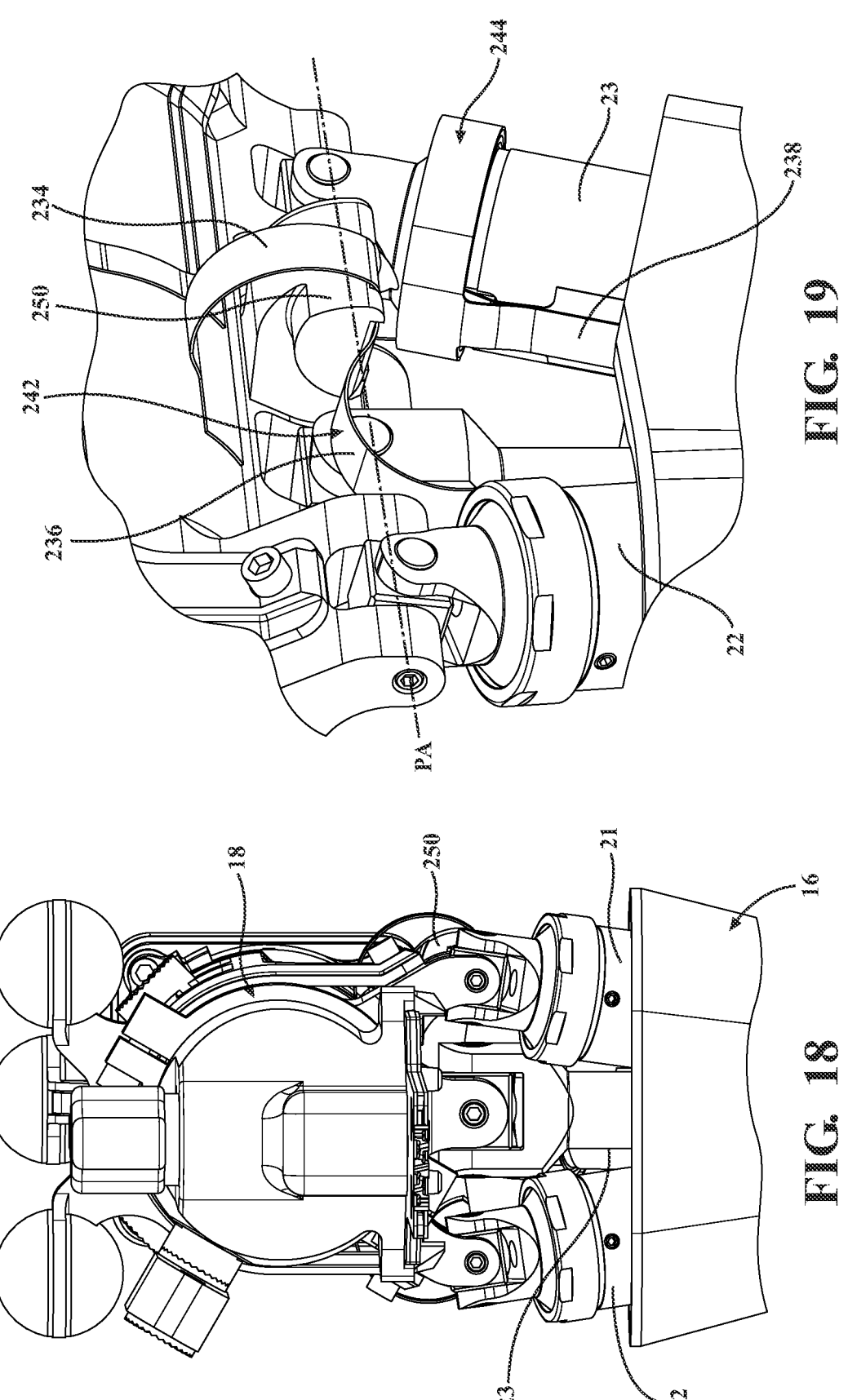
FIGS. 18 and 19 display actuator flexible circuit arrangement.

Referring to FIGS. 16-18, a flexible circuit support 212 is mounted to the tool support 18 via one or more attachment members 214 to attach one or more of the actuator flexible circuits 230, 232, i.e., one or more of the flexible circuits, of the flexible circuit assembly 210 that extend to the actuators 21, 22 to the tool support 18. In particular, the two actuator flexible circuits 230, 232 are connected to the flexible circuit support 212 by attachment members 214 at flex guides 250. The attachment members 214 act to restrain the actuator flexible circuits 230, 232 against or adjacent to a surface of the flex guide 250. The attachment members 214 may comprise fasteners, e.g., screws, adhesive, etc., or any other suitable form of an attachment member to hold the actuator flexible circuits 230, 232 at the locations shown. In another example, the flexible circuit assembly 210 may be attached to the flexible circuit support 212, the flex guide 250, the tool support 18, the hand-held portion 16, or a combination thereof through alternative fixing means, such as adhesive.

In one example, as shown in FIGS. 16 and 17, the flexible circuit support 212 comprises a body defining one or more mounting locations 216 for receiving the attachment members 214. The actuator flexible circuits 230, 232 that are captured by the attachment members 214 comprise openings 220 through which the attachment members 214 secure the actuator flexible circuits 230, 232 to the body (see openings 220 shown in FIG. 14). The flex guides 250 also define a pair of notches 218 sized to receive the actuator flexible circuits

230, 232 of the flexible circuit assembly 210 to guide those actuator flexible circuits 230, 232 in a manner that reduces stress on the actuator flexible circuits as the actuators 21, 22 move during operation.

As discussed above with reference to FIGS. 9 and 11, the actuators 21, 22, 23 are arranged and assembled in the present teachings so that the housings 134 of the actuators 21, 22, 23 are connected via pivot yoke 106 to the tool support 18 at the actuator mounts 86, 88, 90. As discussed above, each actuator 21, 22, 23 includes an actuator motor 142 disposed within the respective housings 134. The actuator motor 142 is connected with and rotates the lead screw 150. The lead screws 150 are connected with the hand-held portion 16 at the second active joints 108 (corresponding to actuators 21, 22) and the third active joint 124 (corresponding to actuator 23). The lead screws 150 are rotated relative to the housing 134 and the actuator motor 142, threading in and out of the second active joint and third active joint, respectively, facilitating movement of the tool support 18 relative to the hand-held portion 16. Since the actuators 21, 22, 23 are attached to the actuator mounts 86, 88, 90 by the pivot yoke 106 formed by the cap 138 of the housings 134, the actuators 21, 22, 23 are only moved in two degrees of freedom (pitch and roll) relative to the actuator mounts 86, 88, 90 of the tool support 18. Thus, the flexible circuits FC, particularly seen in FIGS. 12-19, are connected along the housing 134 of each actuator 21, 22, 23 at connection points 238 such that the actuator flexible circuits 230, 232 only require enough material length between the flex guides 250 of tool support 18 and each actuator 21, 22 to move in the same two degrees of freedom (e.g. pitch and roll) as the actuators 21, 22, 23 move relative to the tool support 18. The housing 134 of actuators 21, 22 have their respective flexible circuit connections 238 disposed between the actuators 21, 22 and the base 74. Similarly, the actuator flexible circuit 234 of the flexible circuit assembly 210 only requires enough material length between the tool support 18 and actuator 23 to move in the same two degrees of freedom (e.g. pitch and roll) as the actuators 21, 22, 23 move relative to the tool support 18. Like actuators 21, 22, the flexible circuit connection 238 of actuator 23 is disposed between the actuator 23 and the base 74. Put another way, the actuator flex connections 238 are facing the base 74.

In some examples, such as shown in FIGS. 12-19, the flexible circuit support 212 is configured to position segments 236 of the actuator flexible circuits 230, 232 between the flex guides 250 and the actuator flex connections 238 to help facilitate moving the flexible circuit assembly 210 through the range of motion of the tool support 18 relative to actuators 21, 22 and the hand-held portion 16 without compromising the connection of the flexible circuits 230, 232 and/or tearing the flexible circuits 230, 232. Looking at FIGS. 17-19, the flexible circuit support 212 may advantageously position the flex guides 250 along the pivot axis PA of actuators 21, 22, axially aligning the actuator flexible circuits 230, 232 of along a longitudinal axis LA with a center point of the pivot axis PA of actuators 21, 22, respectively to control deformation of the actuator flexible circuits 230, 232 in a roll degree of freedom, a pitch degree of freedom, or both. More particularly, the positioning of the flex guides 250 in this manner distributes the change in the roll degree of freedom and the pitch degree of freedom of the flexible circuit 230, 232 over a greater length to avoid sharp bends which could compromise the integrity of the flexible circuit.

Additionally, the actuator flexible circuits 230, 232 may include additional material in segment 236 between the flex guide 250 and the connections 238 with the actuators 21, 22 to assist with maintaining the connection of the flexible circuits 230, 232 between the tool support 18 and the actuators 21, 22 as the tool support 18 is moved relative to the hand-held portion 16. The segments 236 of the actuator flexible circuits 230, 232 are routed through the flex guides 250 to the actuator flex connections 238 and may be formed as a curved bend. The flex guides 250 support the actuator flexible circuits 230, 232 through the range of motion, particularly in at least a roll direction and a pitch direction, as the tool support 18 is moved relative to the hand-held portion 16.

Similarly, the actuator flexible circuit 234 of the flexible circuits assembly 210 extends to and connects with the third actuator 23. As shown in FIGS. 14, 15, and 17, the actuator flexible circuit 234 is routed from the control housing 29 and control boards 31 on the tool support 18 to the third actuator 23. As noted above, the flexible circuit connection 238 of actuator 23 is disposed between the actuator 23 and the base 74. The actuator flexible circuit 234 is routed to minimize the amount of material required to avoid binding of the flexible circuit during articulation of the tool support while optimizing the length to allow for the actuator flexible circuit 234 to move through the range of motion as the tool support 18 is moved relative to the hand-held portion 16 without causing damage to the flexible circuit 234.

The actuator flexible circuit 234 may include a wrapped section around a circumference of actuator 23, forming a flexible circuit loop 244. The flexible circuit loop 244 may provide the actuator flexible circuit 234 enough length to maintain the connection with actuator 23 while the tool support 18 is moved relative to the hand-held portion 16 in the plurality of degrees of freedom without binding and snapping. The flexible circuit loop 244 may be axially aligned with a longitudinal axis of the actuator 23 while the actuator 23 is in a home position. In some examples, such as shown in FIGS. 12-14, 18, and 20, the flexible circuit loop 244 is wrapped at least 270 degrees of rotation about actuator 23. In other examples, the wrapped section of the actuator flexible circuit 234 is routed at least one and three-quarters rotations about actuator 23. Other examples of wrapping the actuator flexible circuit 234 around the actuator 23 are contemplated. By locating the loop about the housing 134 of the actuator 23, rather than about the lead screw 150, interference between the flexible circuit 234 and the actuator 23 is minimized.

Figures 20, 21:
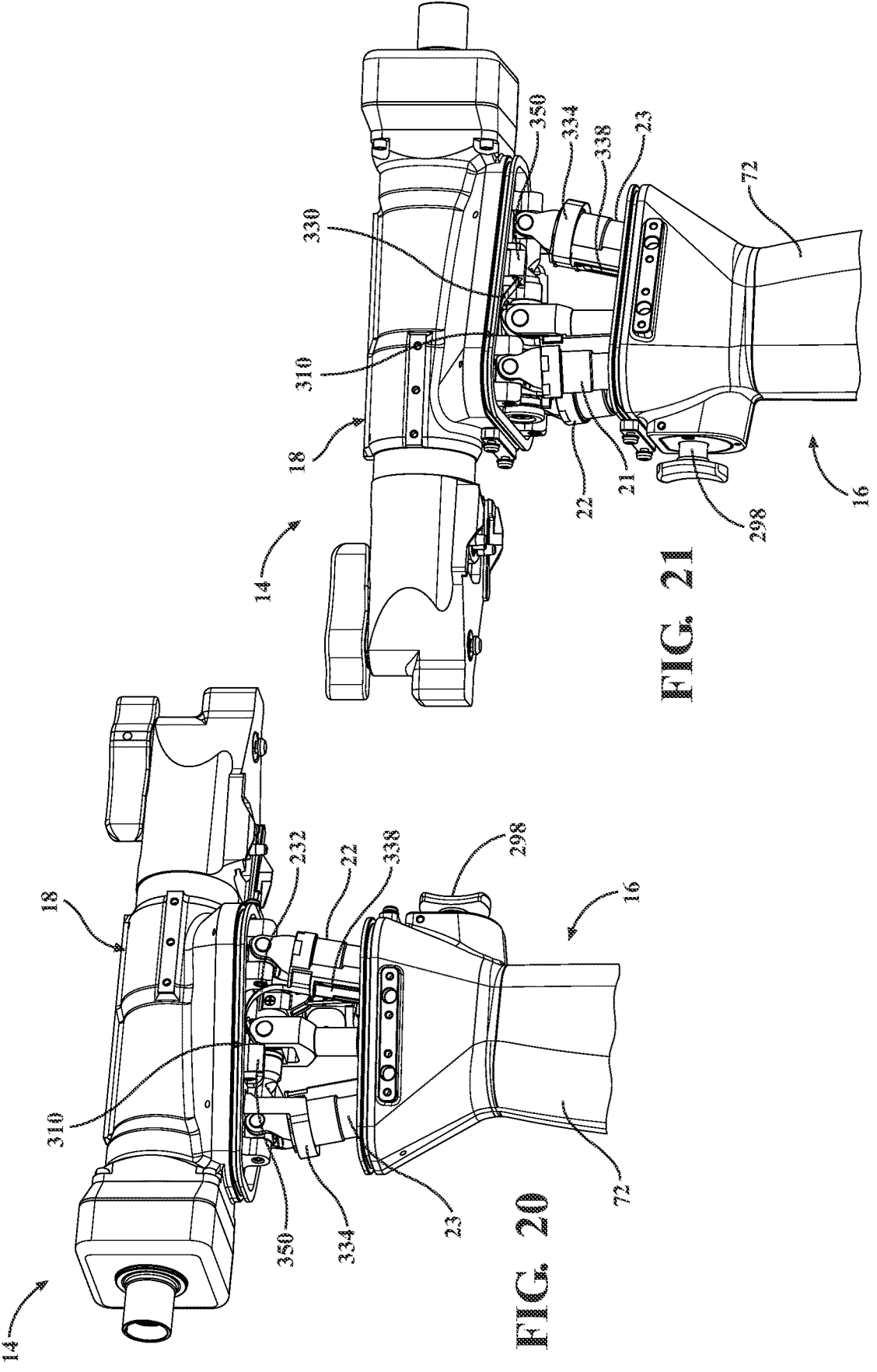
FIGS. 20 and 21 are perspective views of another example of the robotic instrument with a flexible circuit assembly.

FIGS. 20 to 40 illustrate an alternative configuration of instrument 14 with an alternative configuration of a flexible circuit assembly 310. The alternative configuration may be substantially similar to the configurations previously described above. FIGS. 20 and 21 display perspective views of the instrument 14. In this configuration, an input device 298 is located on the hand-held portion 16. The input device 298 is configured as a trigger assembly in this depiction. The input device 298 in this configuration is located on the grip 72 to allow a user to selectively send an actuation signal to the instrument controller 28.

Figures 24, 25:
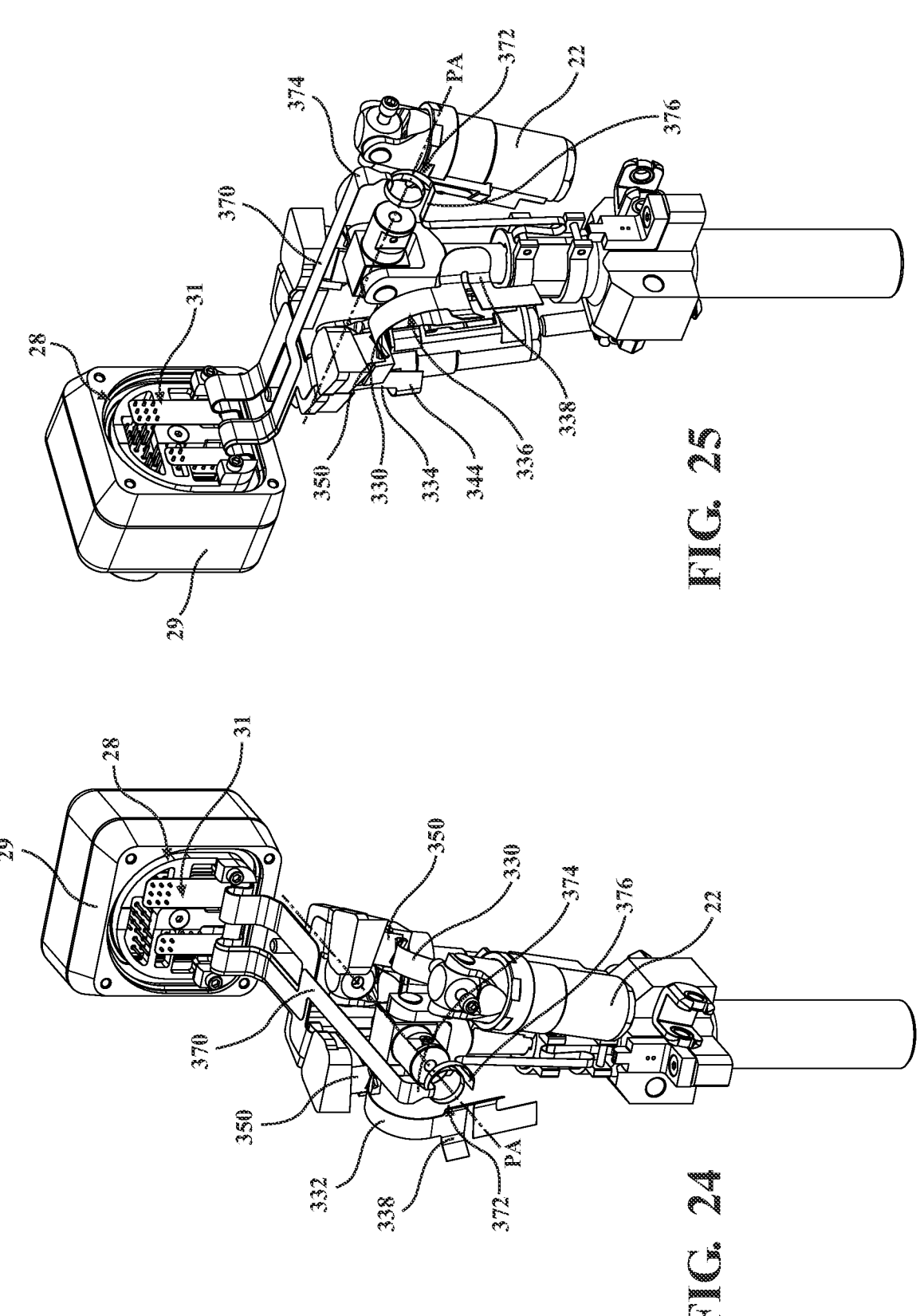
FIGS. 24 and 25 illustrate a portion of the actuator assembly and the actuator flexible circuits.
Figure 26:
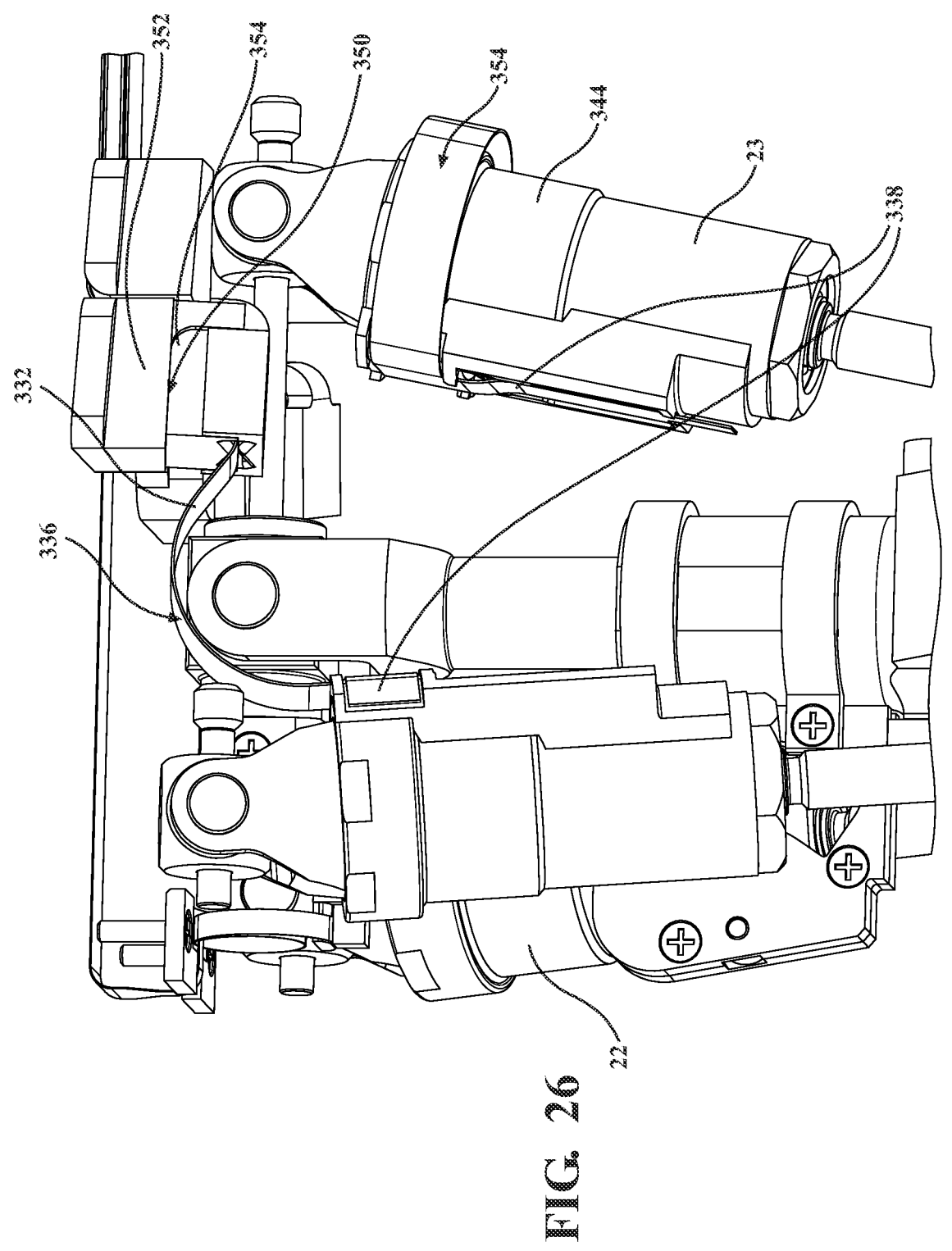
FIG. 26 is a perspective view of the flexible circuit path from the tool support to the actuators.

FIGS. 20 and 21 display perspective views of the instrument 14 including the alternative flexible circuit assembly 310. As noted above, the circuits FC interconnect the actuators 21, 22, 23 and/or other components with the instrument controller 28. For example, FIGS. 24-26 are shown with flexible circuits FC provided between the actuators 21, 22, 23, and the control boards 31 in the control housing 29. The flexible circuits FC are configured to maintain the connection between the actuators 21, 22, 23 and the control boards 31 as the tool support 18 is moved in a plurality of degrees of freedom relative to the hand-held portion 16.

Figures 22, 23:
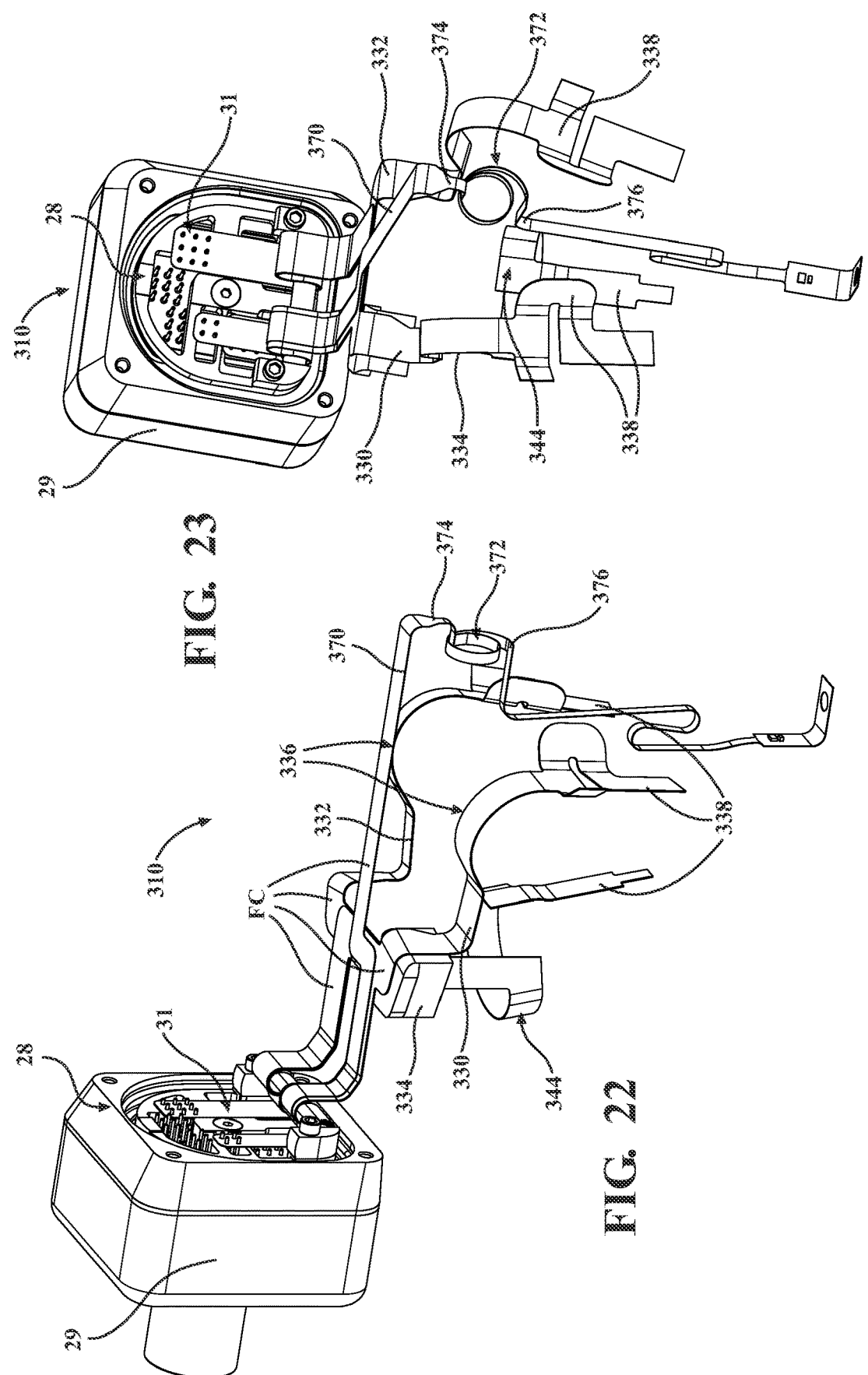
FIGS. 22 and 23 illustrate perspective views of the flexible circuits from the robotic instrument of FIGS. 20 and 21.

Routing of the flexible circuits FC in one example is shown in FIGS. 22-29. FIGS. 22-25 show the flexible circuits FC and the control housing 29 (holding control boards 31) isolated from the remainder of the instrument 14. As shown in FIGS. 22-23, the flexible circuits FC form part of a flexible circuit assembly 310. The flexible circuit assembly 310 may comprise multiple, actuator flexible circuits (or legs) 330, 332, 334 formed in one-piece or formed as separate portions that may be attached together. The actuator flexible circuits 330, 332, 334 may comprise one or more flexible plastic substrates, such as polyimide, transparent conductive polyester film, or the like.

The flexible circuit assembly 310 comprises conductors mounted and/or embedded in the flexible plastic substrates. The conductors may include one or more circuits for transmitting data and/or power between the actuators 21, 22, 23, and one or more of the control boards 31. Circuit leads (not shown) are disposed on the ends of the flexible actuator flexible circuits 330, 332, 334 for connecting to the actuators 21, 22, 23, respectively. The conductors may also comprise one or more circuits for transmitting data and/or power between the actuator sensors AS and one or more of the control boards 31 (or the actuator sensors AS may be considered part of the actuators 21, 22, 23) and/or other sensors that are utilized in the instrument, such as a trigger sensor. The conductors may comprise one or more circuits for transmitting data and/or power between an input device 298, such as a trigger assembly (described further below).

It should be understood that the flexible circuits may be separated between a first portion of the flexible circuit that extends to the motor of each actuator and another portion that extends to the encoder/sensors of each actuator with the first and second portion optionally joining together as a main flex that goes back to the one or more of the controllers/ control boards. The partially split flexible circuit configuration can be used for all of the different actuator flexible circuits and/or for other flexible circuits that are used throughout the instrument, such as the flexible circuit that extends to the input device/trigger assembly.

Referring to FIGS. 24-32, the flexible circuit assembly 310 is routed throughout the tool support 18 to the actuators 21, 22, 23 and an input device 298. The actuator flexible circuits 330, 332 of the flexible circuit assembly 310 that extend to the actuators 21, 22 are routed through flex guides 350. In one example, as shown in FIGS. 24-26, the flex guides 350 are mounted to the tool support 18 and are configured to position the actuator flexible circuits 330, 332 advantageously relative to the actuators 21, 22, in order to minimize deformation in two or more degrees of freedom when the tool support 18 is moved relative to the hand-held portion 16.

As discussed above, the flexible circuits FC, particularly seen in FIGS. 24-26 and 36-37, are connected along the housing 134 of each actuator 21, 22, 23 at flex connection 338 such that the actuator flexible circuits 330, 332 of the flexible circuit assembly 310 only require enough material length between the flex guides 350 of tool support 18 and each actuator 21, 22 to move in the same two degrees of freedom (e.g. pitch and roll) as the actuators 21, 22, 23 move relative to the tool support 18. The actuators 21, 22 have their respective flexible circuit connections 238 disposed between the actuators 21, 22 and the base 74. Similarly, the actuator flexible circuit 334 of the flexible circuit assembly 310 requires enough material length between the tool support 18 and actuator 23 to move in the same two degrees of freedom (e.g. pitch and roll) as the actuators 21, 22, 23 move relative to the tool support 18. Like actuators 21, 22, the flexible circuit connection 338 of actuator 23 is disposed between the actuator 23 and the base 74. Put another way, the actuator flex connections 338 are facing the base 74.

The flex guides 350 are configured to route those flexible actuator flexible circuits 330, 332 in a manner that reduces stress on the flexible actuator flexible circuits as the actuators 21, 22 move during operation. FIGS. 26-29 show the actuator flexible circuit 330, 332 captured through the flex guides 350. In some examples, such as shown in FIGS. 20-29, the flex guides 350 are positioned in a relatively canted manner relative to actuators 21, 22. The flex guides 350 are configured to position segments 336 of the actuator flexible circuits 330, 332 between the flex guides 350 and the actuator flex connections 338 to help facilitate moving the flexible circuit assembly 310 through the range of motion of the tool support 18 relative to actuators 21, 22 and the hand-held portion 16 without breaking connection and/or tearing the flexible circuits FC. Looking at FIGS. 28-30, the flex guides 350 may be positioned canted to the pivot axis PA of actuators 21, 22, aligning the actuator flexible circuits 330, 332 with a center point of the pivot axis PA of actuators 21, 22, respectively, to minimize deformation of the actuator flexible circuits 330, 332 in a roll degree of freedom, a pitch degree of freedom, or both.

Figures 30, 31, 32:
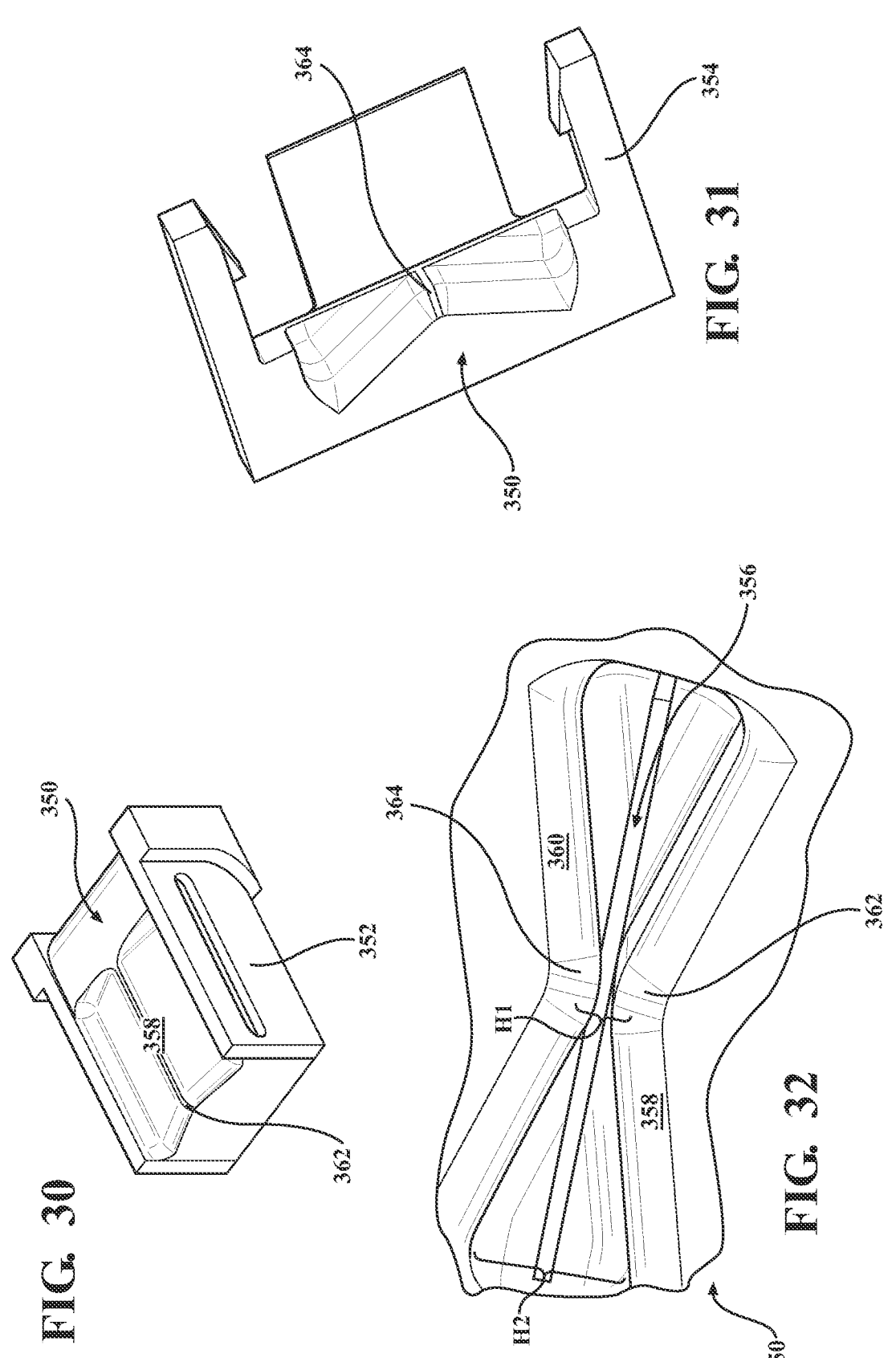
FIGS. 30 and 31 illustrate an upper and a lower portion of a flex guide.
FIG. 32 illustrates a forward view a flex guide.

Turning to FIGS. 31 and 32, one or more of the flex guides 350 each include a profile which defines the span of rotation of the flexible actuator flexible circuits 330, 332 of the flexible circuit assembly 310 during pitch and roll movement. The profile may be configured to be wider than the width of the actuator flexible circuits 330, 332, such that the flex guide 350 provides support across the width of the actuator flexible circuits 330, 332 when the tool support 18 is moved relative to the hand-held portion 16. The flex guides 350 are each formed with a channel 356 between a top surface 358 and a bottom surface 360. Both the top surface 358 and the bottom surface 360 may have the same profile or a different profile. The profile of the channel 356 may include varying heights at different sections of the channel 356. For example, in FIG. 32, the channel 356 is shaped with a protrusion 362 extending from the top surface 358 and a protrusion 364 extending from the bottom surface 360. Each protrusion 362, 364 forming an angled surface from the protrusion 362, 364 to each side of the channel 356. From each of the protrusions 362, 364, the height of the channel 356 is increased moving laterally to either side along the angled surfaces. For example, the first height H1 may be the height between the first protrusion 362 and the second protrusion 364, and a second height H2 may be the distance between the top surface 358 and the bottom surface 360 of the channel 356, such that during operation, the actuator flexible circuits 330, 332 may contact the first height H1 when the hand-held portion 16 has a maximum range of motion (e.g. when the actuators 21, 22, 23 are in their respective home positions). The actuator flexible circuits 330, 332 are configured to pivot about the protrusions 362, 364 while the tool support 18 is moved relative of the hand-held portion 16, providing support across the width of the actuator flexible circuits 330, 332, preventing ripping or tearing while maintaining the electrical connection. The thickness of the flexible actuator flexible circuits 330, 332 is less than the distance between the top protrusion 362 and the bottom protrusion 364 of the channel 356, allowing the actuator flexible circuits 330, 3322 to pass through the channels 356 of the flex guides 350.

Figure 27:
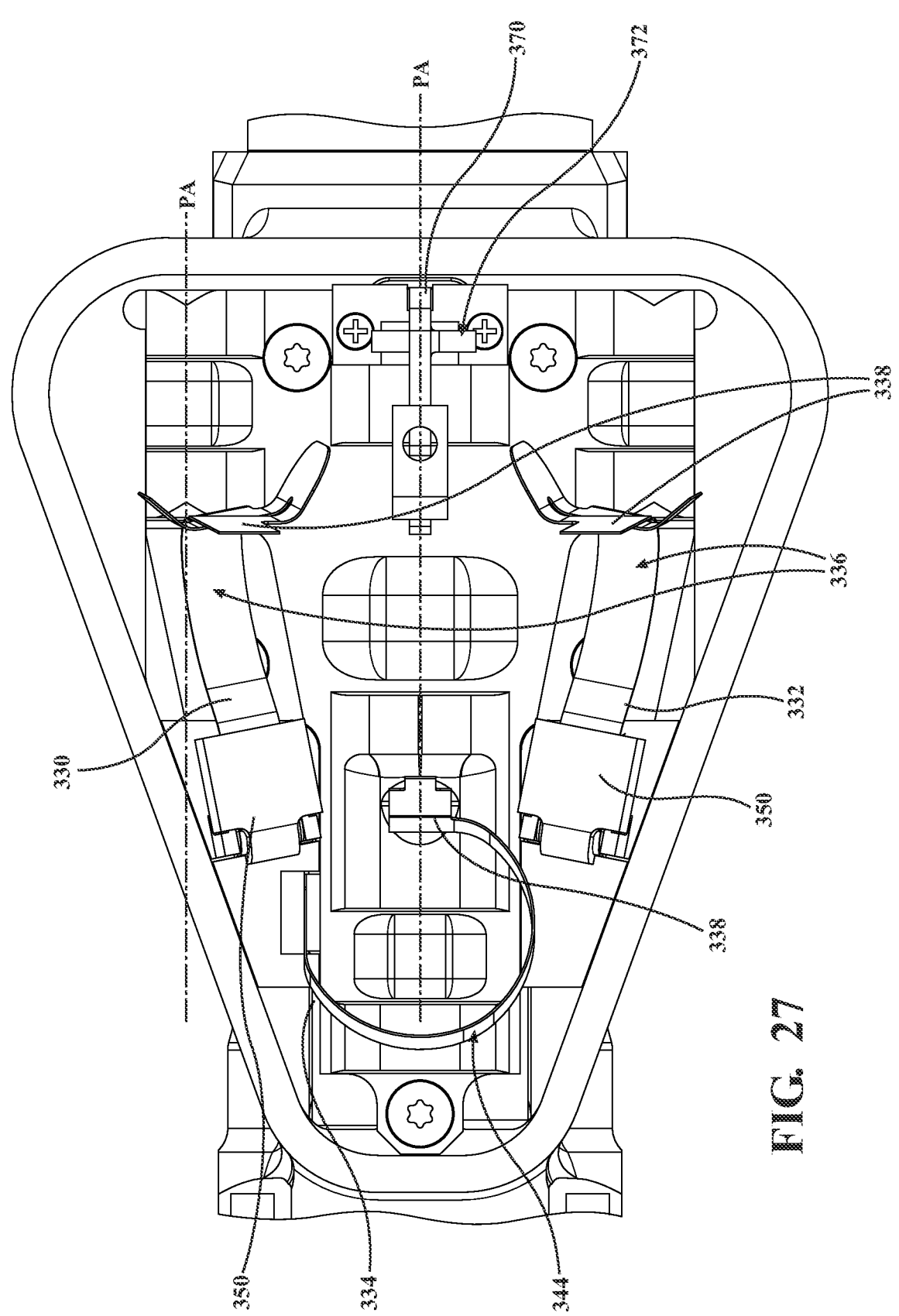
FIG. 27 illustrates a bottom view of the tool support with flexible circuits.
Figures 28, 29:
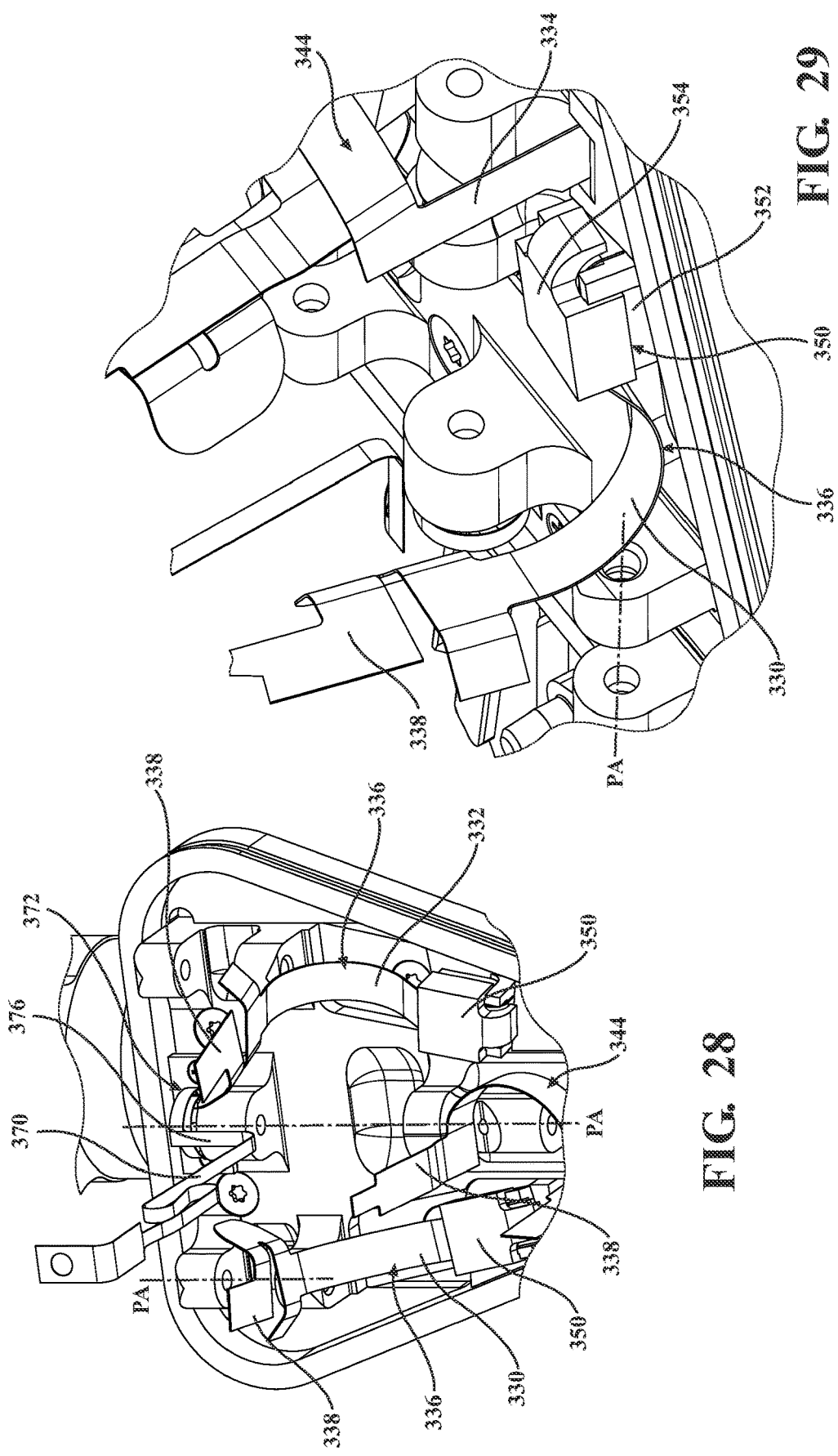
FIG. 28 illustrates a partial bottom view of the tool support with flexible circuits.
FIG. 29 illustrates a partial bottom view of the tool support with flexible circuits.
Figure 33:
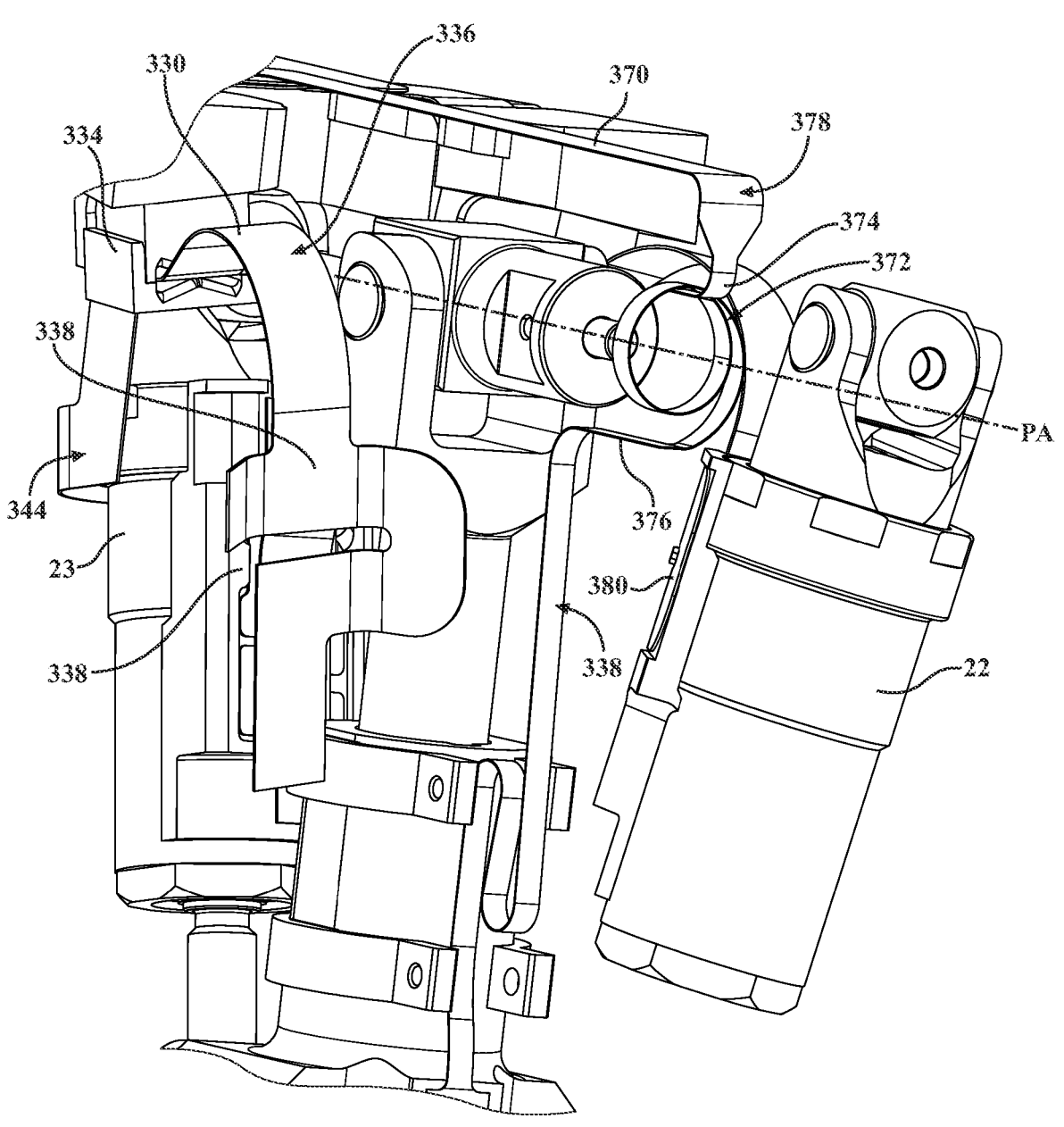
FIG. 33 displays a perspective view of a flexible circuit assembly.

As seen best seen in FIGS. 30-32, the flex guides 350 may be configured as a two-piece design, with a base 352 and a cover 354. The base 352 may be connected with the tool support 18 and the cover 354 may be configured to connect with the base 352. In some examples, the cover 354 may be connected with the base in a snap fit connection. In other configurations, the cover 354 may connect with the base 352 in a friction fit connection, press fit connection, slip fit connection, or any other type of mechanical attachment connection. As can be seen in FIGS. 26, 27, and 33, the base 352 and the cover 354 of the flex guide are configured to surround and guide the flexible actuator flexible circuits 330, 332, positioning the actuator flexible circuits 330, 332 in a desirable relationship between the tool support 18 and the actuators 21, 22. In some examples, the base 352 and the cover 354 each have their own profile which defines the profile and the channel 356 of the flex guide 350 when the base 352 and cover 354 are connected.

The actuator flexible circuits 330, 332 may include additional material in segment 336 between the flex guide 350 and the connections 338 with the actuators 21, 22 to assist with maintaining the connection of the flexible circuits FC between the tool support 18 and the actuators 21, 22 as the tool support 18 is moved relative to the hand-held portion 16. The segments 336 of the flexible actuator flexible circuits 330, 332 are routed through the flex guides 350 to the actuator flex connections 338 and may be formed as a curved bend. The flex guides 350 support the actuator flexible circuits 330, 332 through the range of motion, particularly in at least a roll direction and a pitch direction, as the tool support 18 is moved relative to the hand-held portion 16.

Turning to FIGS. 34A-35B, input device flexible circuit 370 is routed from an input flex guide assembly 340. The input flex guide assembly 340 guides flexible circuit 370 as the tool support 18 is moved relative to the hand-held portion 16 and the tensioning assembly 266, 410 adjusts as the plurality of actuators 21, 22, 23 are actuated. The input flex guide assembly 340 may be keyed and secured to the passive linkage mount 162. The input flex guide assembly 340 may function to allow the input device flexible circuit 370 to be aligned to the midplane of the hand-held portion just below the pivot axis PA. The input flex guide assembly 340 guides and routes the input device flexible circuit 370 such that the tensioning assembly 266, 410 to compensate for both elevation and pitch (described further below). Additionally, the input flex guide assembly 340 facilitates the angle and/or tightness of loop 372 when the tool support 18 is rolled relative to the hand-held portion 16. It should be appreciated that the input flex guide assembly may be utilized independently of the tensioning assembly, and vice-versa.

Figure 34A:
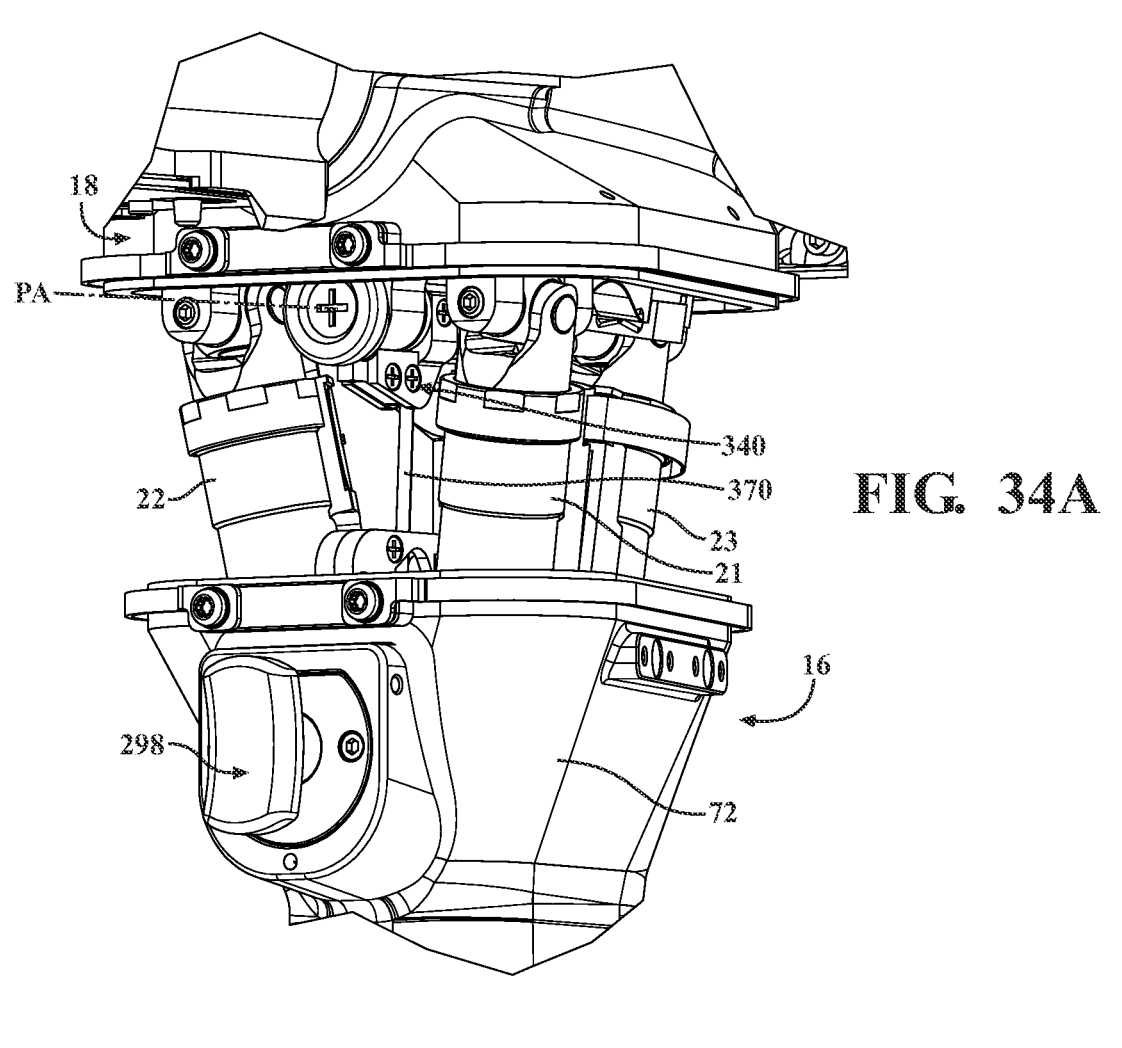
FIGS. 34A and 34B illustrate a portion of actuator assembly and the input guide assembly.
Figure 34B:
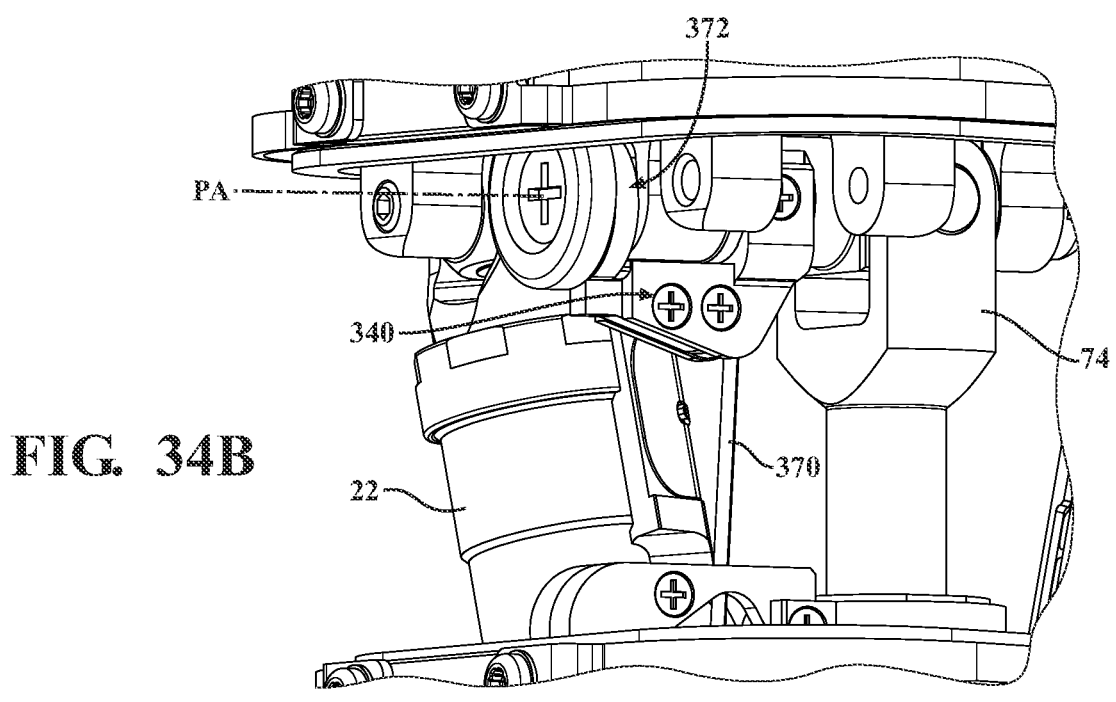
Figure 35B:
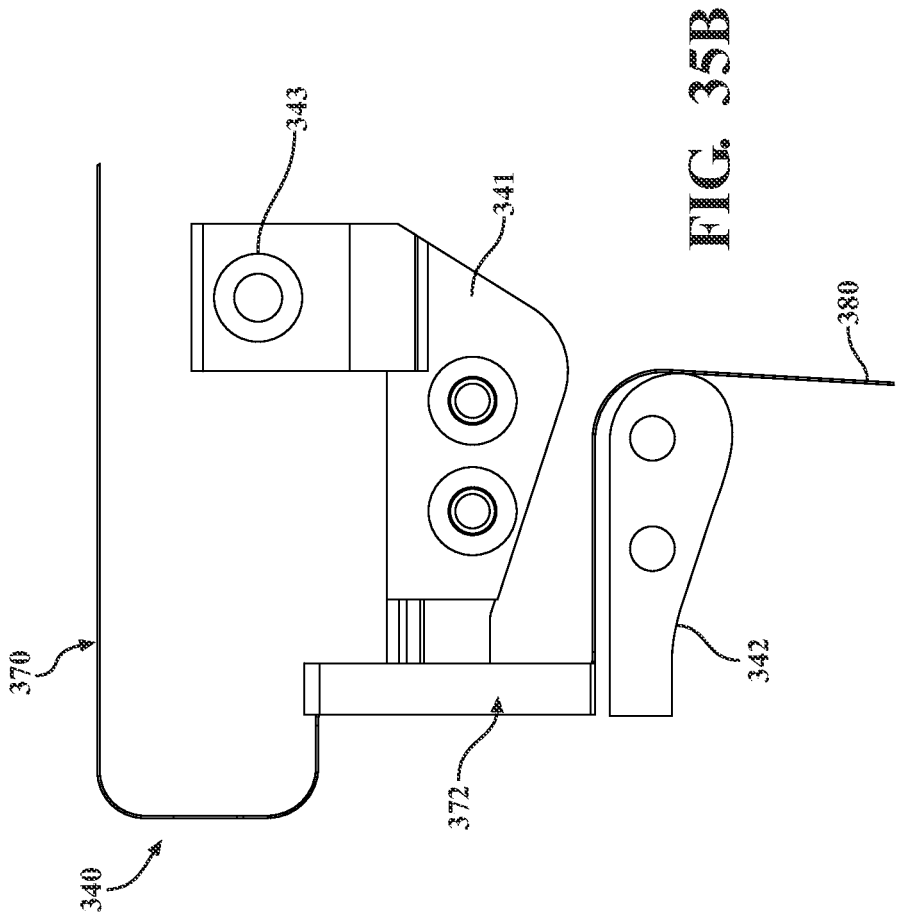
FIG. 35B illustrates an exploded view of the input device flex guide assembly.
Figure 35A:
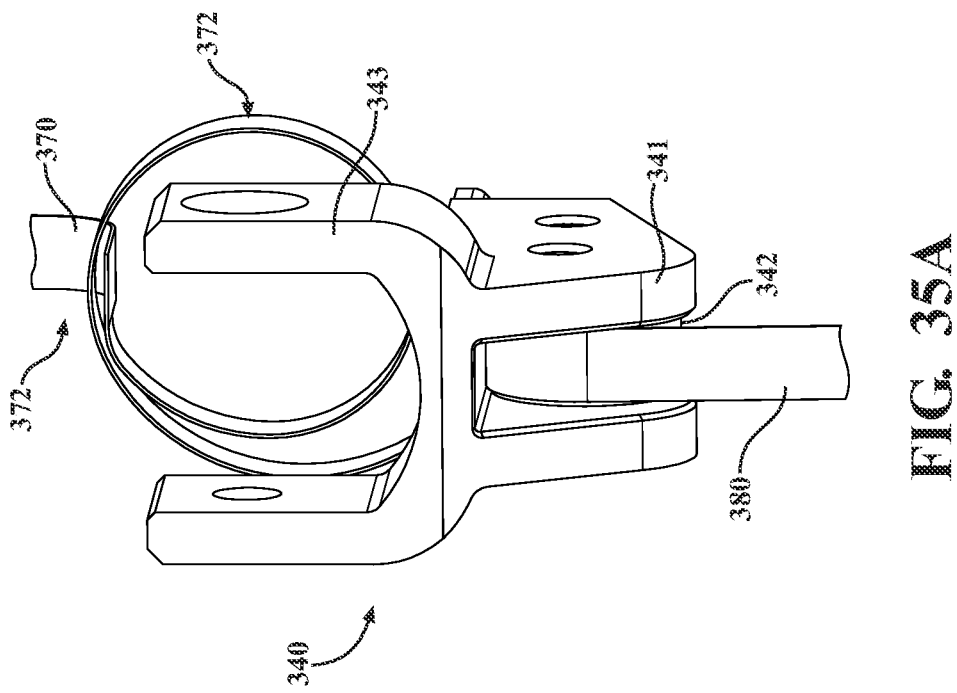
FIG. 35A illustrates the input device flex guide assembly.
Figures 36, 37:
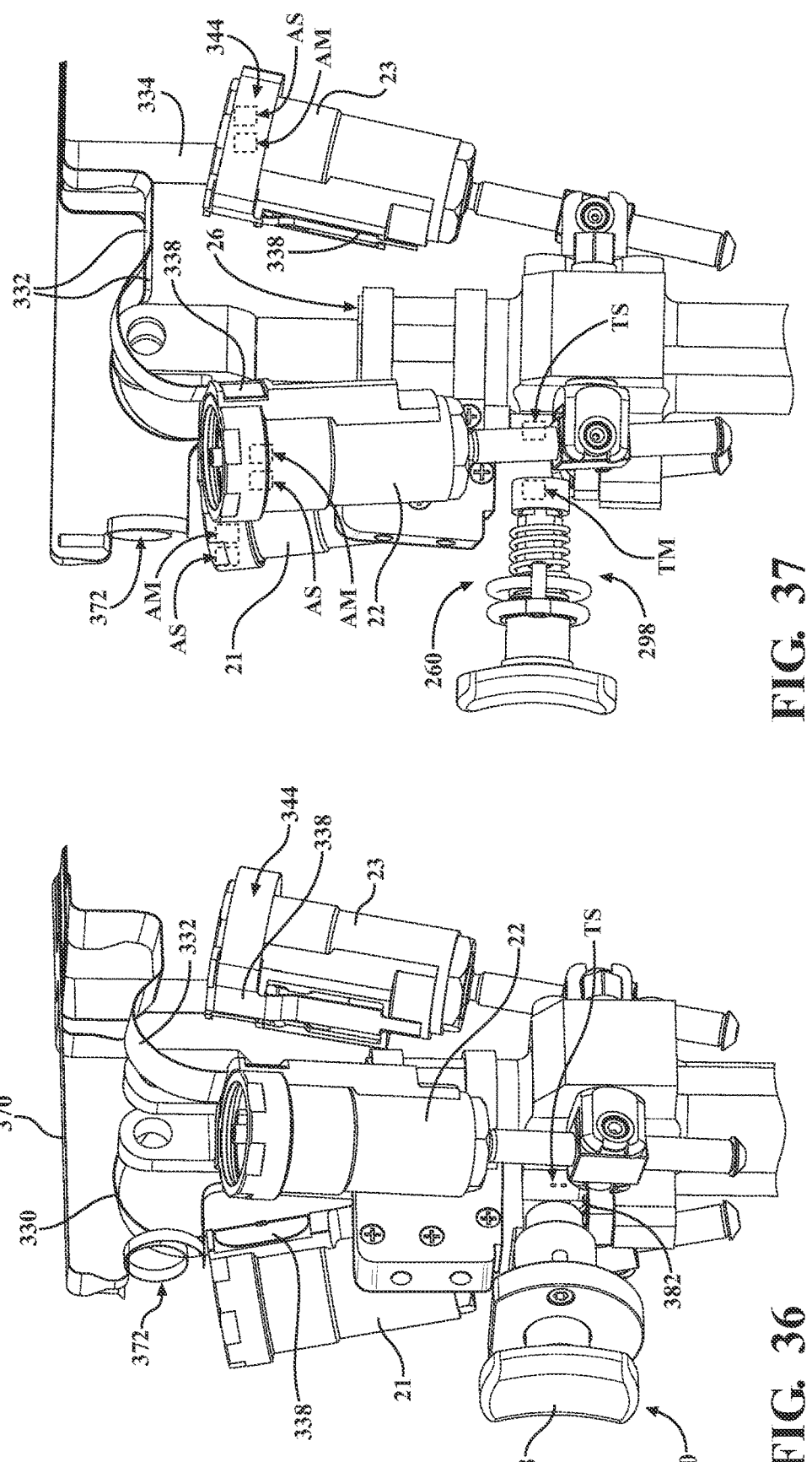
FIGS. 36 and 37 are perspective views of the actuator assembly and flexible circuit assembly including an input device assembly.

FIGS. 35A and 34B illustrate enhanced views of the input flex guide assembly 340. FIG. 35A shows the input flex guide assembly 340 isolated from the tool support 18 and shows the input device flexible circuit 370 in phantom. The input device flexible circuit 370 is routed beneath the flex guide base 341 and over the input flex guide routing member 342. The input flex guide assembly 340 connects with the passive linkage mount 162 at the mounting section 343 of the flex guide base 341.

Similarly, the actuator flexible circuit 334 of the flexible circuits FC extends to and connects with the third actuator 23. As shown in FIGS. 22 and 26-29, the actuator flexible circuit 334 is routed from the control housing 29 and control boards 31 on the tool support 18 to the third actuator 23. As noted above, the flexible circuit connection 338 of actuator 23 is disposed between the actuator 23 and the base (not shown). The actuator flexible circuit 334 of the flexible circuit assembly 310 is routed to minimize the amount of material required while optimizing the length to allow for the actuator flexible circuit 334 to move through the range of motion as the tool support 18 is moved relative to the hand-held portion 16.

The actuator flexible circuit 334 may include a wrapped section around a circumference of actuator 23, forming a flexible circuit loop 344. The flexible circuit loop 344 may provide the actuator flexible circuit 334 enough length to maintain the connection with actuator 23 while the tool support 18 is moved relative to the hand-held portion 16 in the plurality of degrees of freedom without binding and snapping. The flexible circuit loop 344 may be axially aligned with actuator 23. In some examples, as best seen in FIGS. 26 and 27, the flexible circuit loop 344 is wrapped at least three-quarters of a rotation about actuator 23. In other examples, the wrapped section of the actuator flexible circuit 334 is routed at least one and three-quarters rotations about actuator 23. Other examples of wrapping the actuator flexible circuit 334 around actuator 23 are contemplated.

Turning now to FIG. 33, the flexible circuit assembly 310 includes an input device flexible circuit 370 (also referred to as the input device portion) of the flexible circuit assembly 310. In some examples, such as in FIGS. 22-25 and 36-37, the input device flexible circuit 370 extends from the c part of the instrument controller 28, in this example, control boards 31 located in the control housing 29, to an input device 298, such as a trigger assembly. Unlike the actuator flexible circuits 330, 332, 334 which connect with actuators 21, 22, 23 and move primarily in two degrees of freedom (pitch and roll), the input device flexible circuit 370 must adjust for three or more degrees of freedom when the tool support 18 is moved relative to the hand-held portion 16, such as in pitch, roll, and z-axis translation directions (elevation relative to the hand-held portion 16).

The input device flexible circuit 370 utilizes an adjustment loop 372 to compensate for roll movement of the tool support 18 relative to the hand-held portion 16. The adjustment loop, as best seen in FIGS. 23-25, 33 and 39, is arranged about a longitudinal pivot axis PA of the tool support 18 at a home position (e.g. when actuators 21, 22, 23 have maximum travel). The adjustment loop 372 is configured to expand and contract as the tool support 18 is moved in the roll degree of freedom relative to the hand-held portion 16. In some examples, to facilitate the range of movement, the adjustment loop 372 may be a length of flexible circuit that surrounds the longitudinal pivot axis of the tool support 18 at least one and three-quarters rotations when each of the actuators are in their home positions, i.e., the median positions about the lead screw 150. In other examples, the adjustment loop 372 may be wrapped about the longitudinal pivot axis of the tool support 18 between three-quarters of a rotation and three full rotations. However, other arrangements are contemplated.

The adjustment loop 372 is connected with the rest of the input device flexible circuit 370 through one or more elbow sections, such as a first elbow section 374 and a second elbow section 376. Turning to FIGS. 33-38, the first elbow section 374 connects the adjustment loop 372 with the segment 378 of the input device flexible circuit 370 of the flexible circuit assembly 310 extending down from the tool support 18 to the adjustment loop 372. The second elbow section 376 connects the adjustment loop 372 with the segment 380 of the input device flexible circuit 370 of the flexible circuit assembly 310 extending up from the hand-held portion 16 to the adjustment loop 372. Each elbow section 374, 376 connects with the adjustment loop 372 at a 90-degree angle, forming two planar segments. however, the elbows 374, 376 may have other angles and configurations which are contemplated, such as bends having an angle between 70 and 130 degrees. Some examples may include two or more planar elbows 374, 376. The elbow sections 374, 376 may be configured to control the location of the deformation of the flexible circuit in order to maintain the connection between the input device 298 and the tool support 18 when the tool support 18 is moved relative to the hand-held portion 16 in a pitched movement, allowing the input device flexible circuit 370 to flex without breaking and maintaining the connection with the trigger assembly 298 or other input device.

Figures 38, 39:
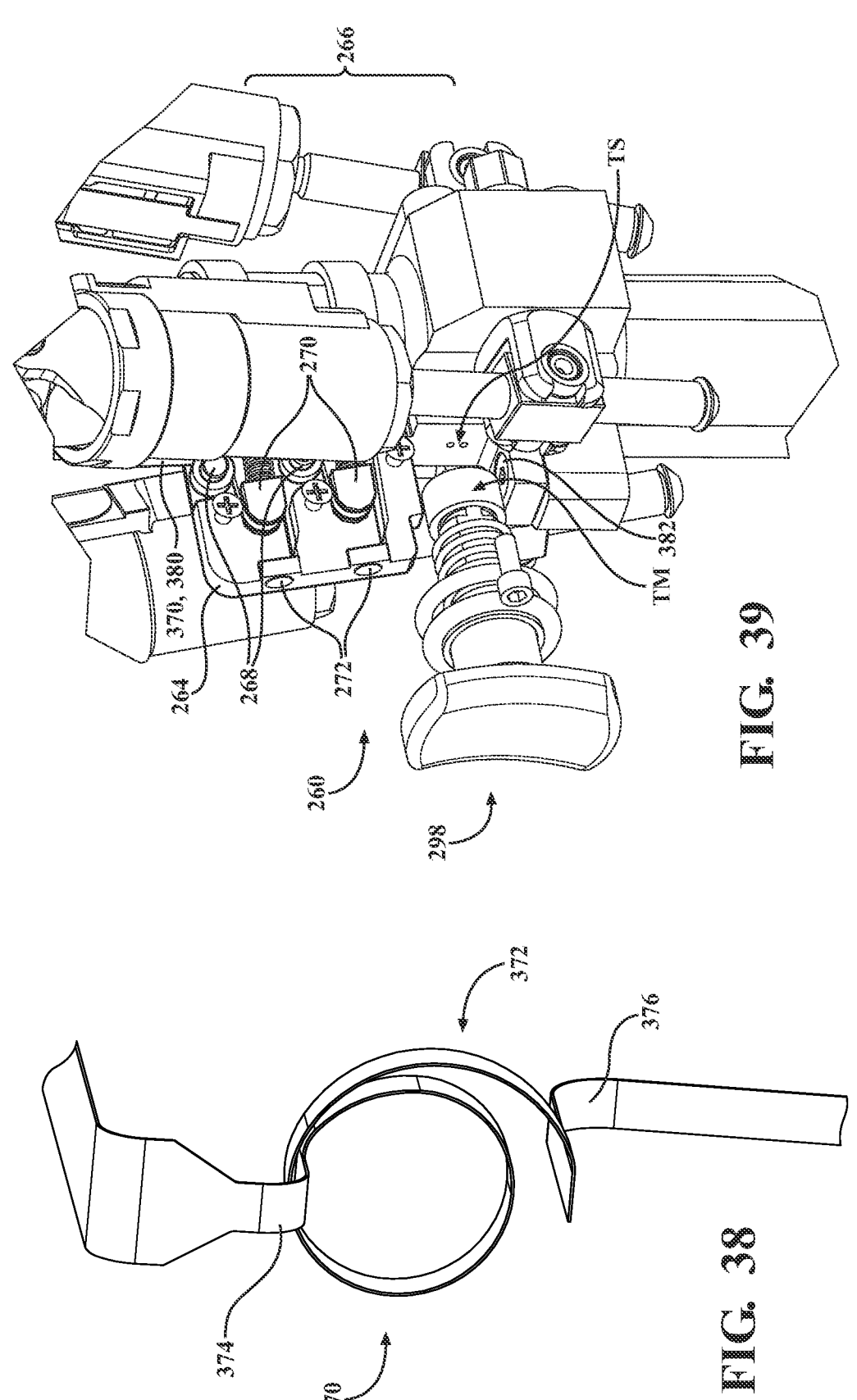
FIG. 38 illustrates a segment of the input device flexible circuit.
FIGS. 39 and 40 illustrate the input device assembly and a tensioning assembly.
Figure 40:
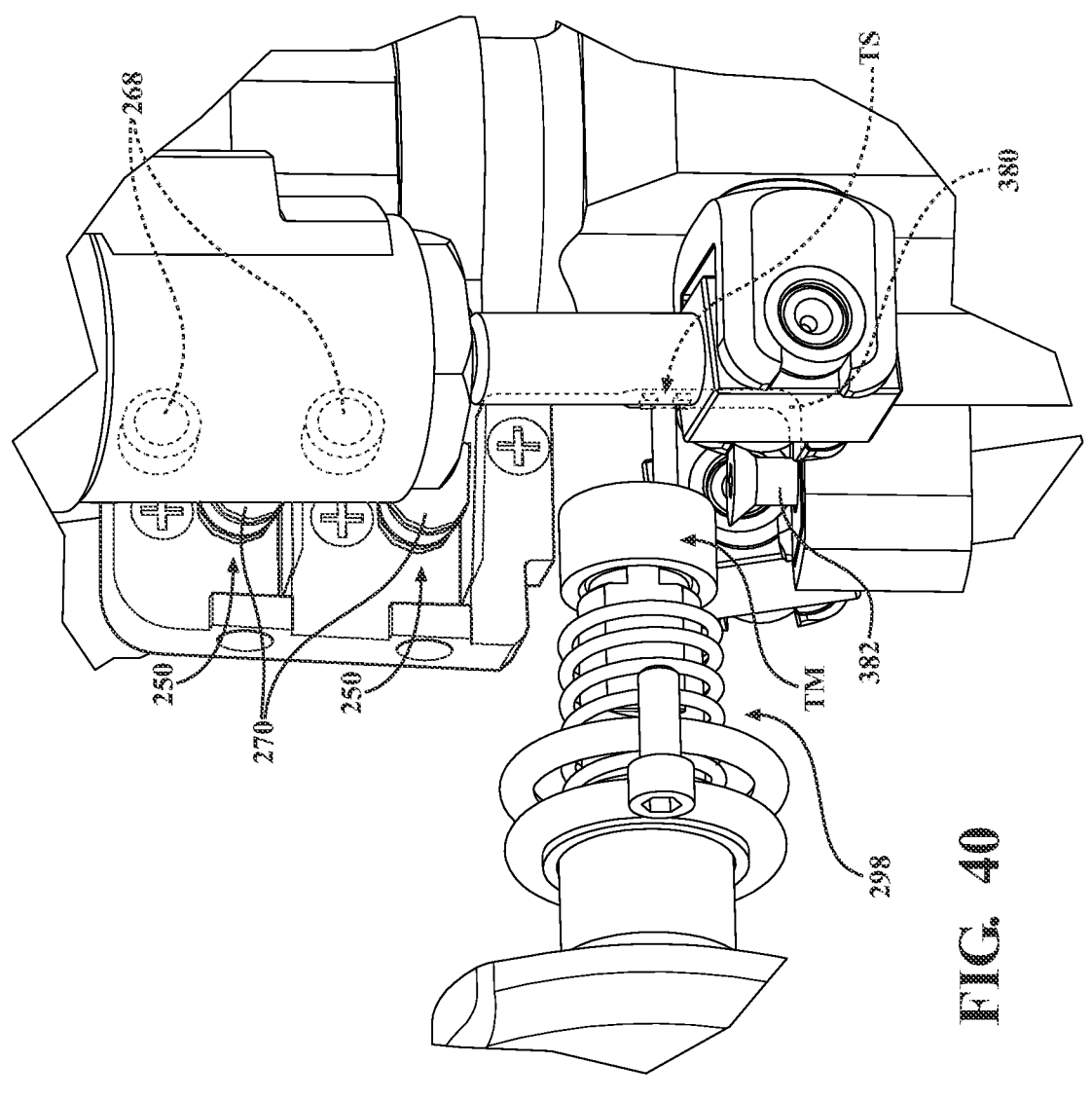
Figure 41:
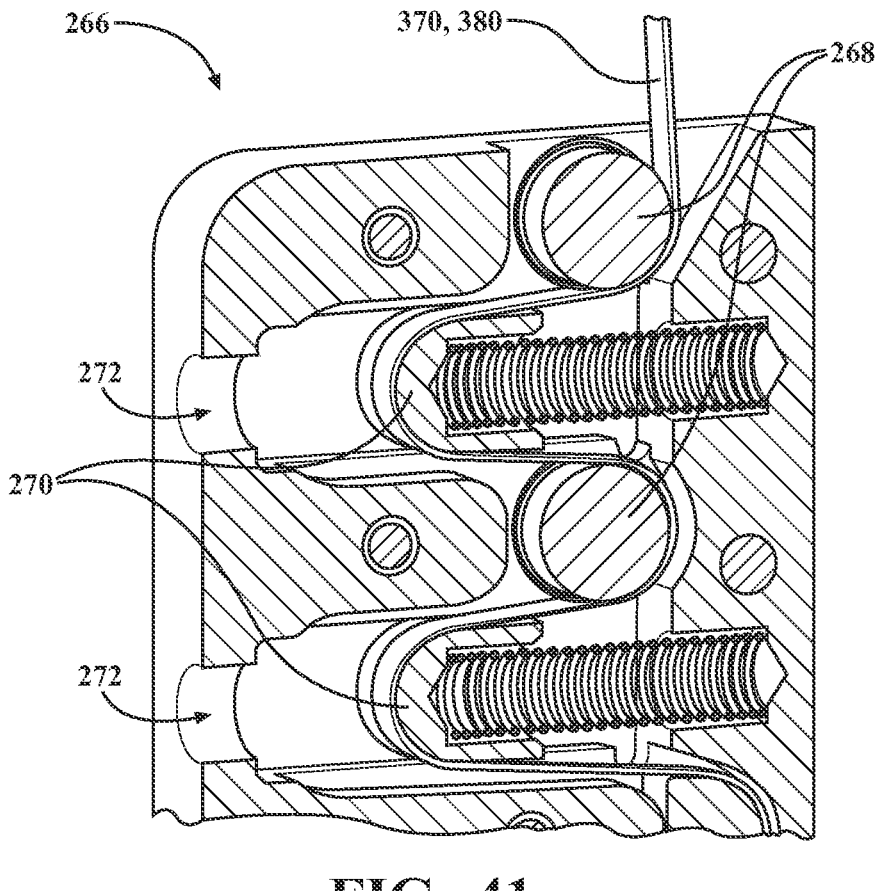
FIG. 41 illustrates the tensioning assembly.
Figure 42:
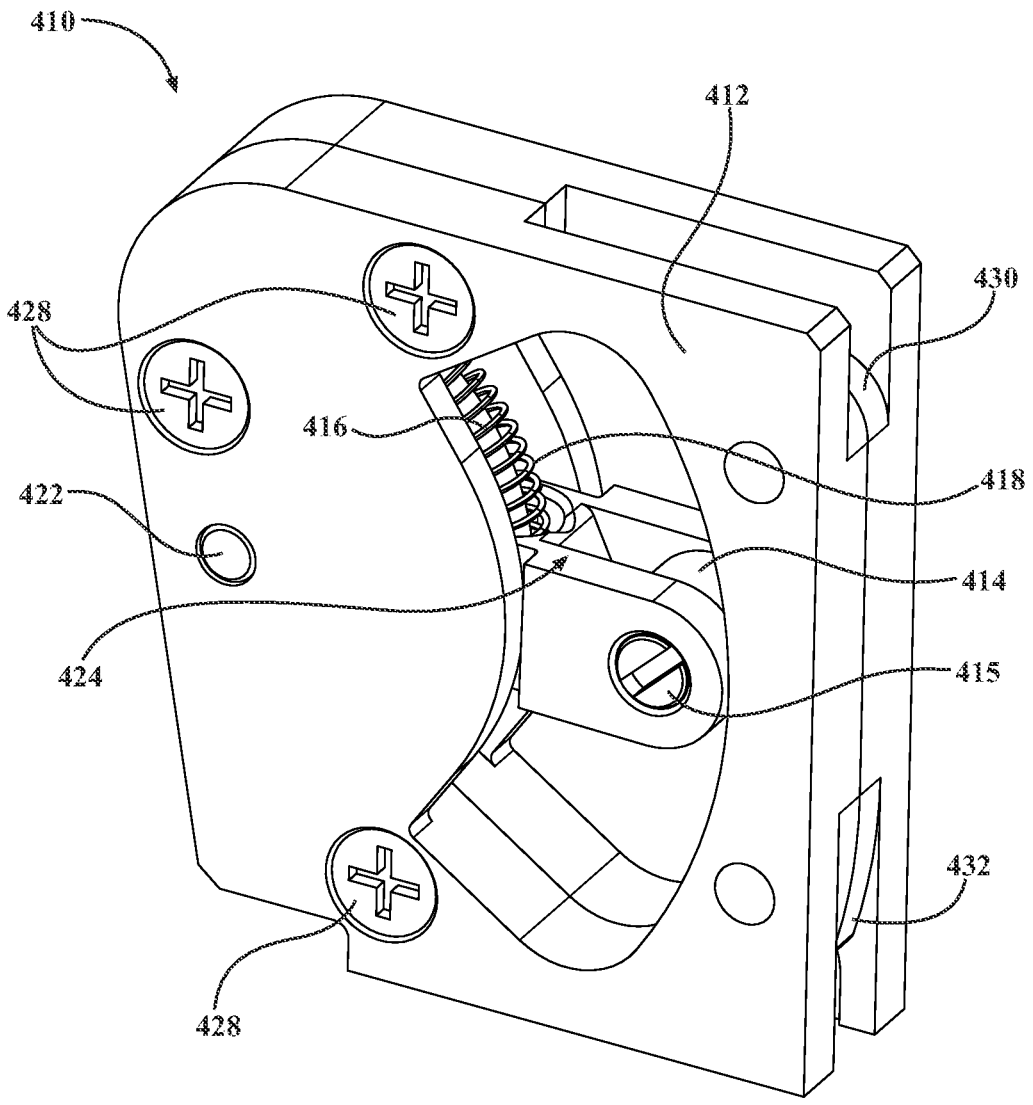
FIG. 42 illustrates an example of a tensioning assembly
Figure 43:
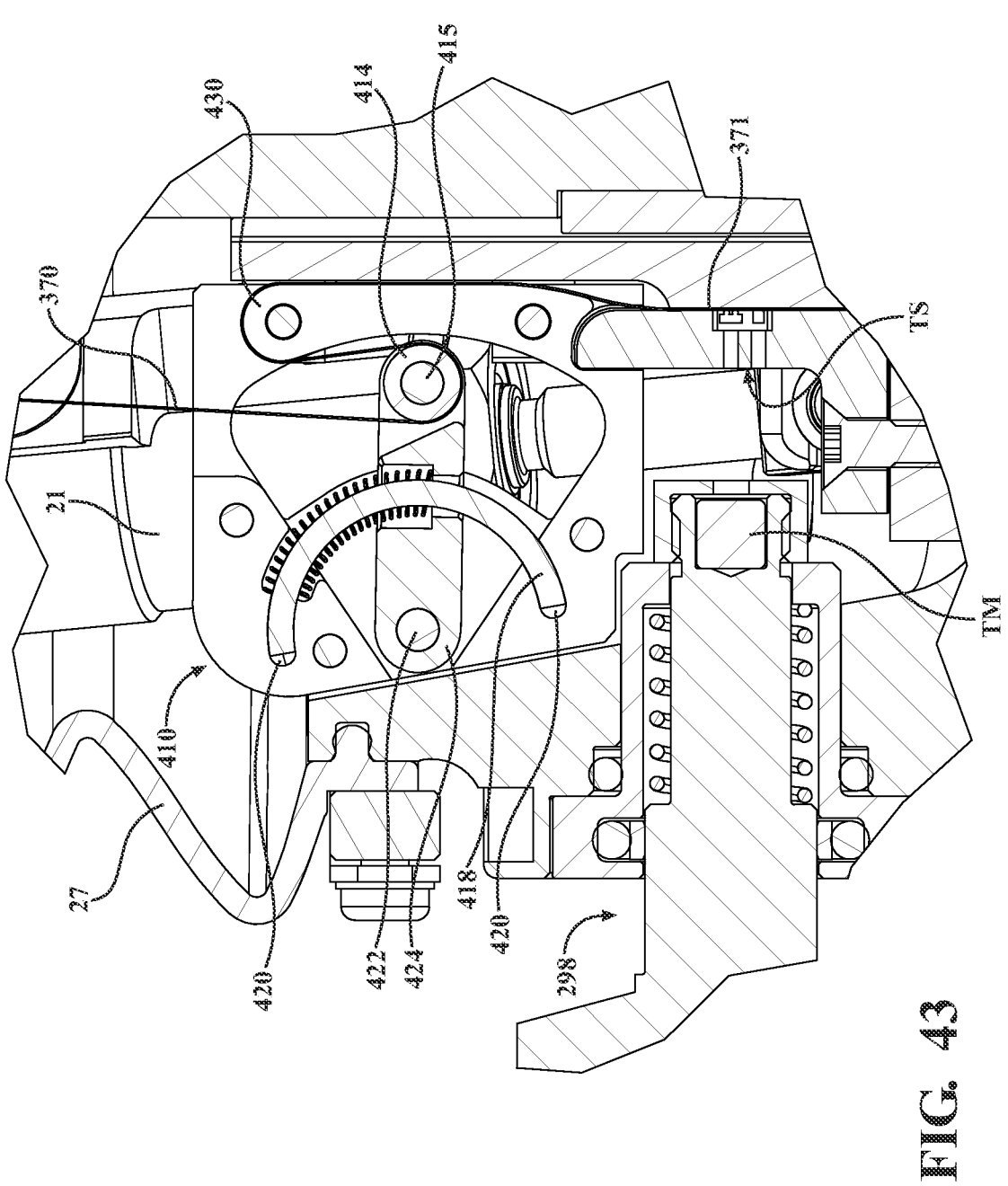
FIG. 43 illustrates a partial cross-section of the tensioning assembly of FIG. 42 within the instrument.

FIGS. 39-41 show the input device flexible circuit 370 connected with the input module assembly 260 including the input device 298, shown here as a trigger assembly. The input module is connected with the input device flexible circuit 370 of the flexible circuit assembly 310 which is routed through the input module assembly 260 and secured to the base 74 by one or more fasteners 382. The input module assembly 260 is located within the hand-held portion 16, however, for illustrative purposes, the majority of the hand-held portion 16 and grip 72 have been hidden from FIGS. 36-42.

FIGS. 36 and 37 and FIGS. 39 and 40 illustrate the input module assembly 260 (interchangeably trigger assembly). In some examples, the input module assembly 260 includes the input device 298 (shown as a trigger) and associated components, such as a biasing member 300, magnet TM, and sensor S. The trigger 298 is positioned so that the trigger sensor TS of the input module assembly 260 is able to ascertain the relative position of the trigger 298 relative to the sensor, so that a user's input may be sent to the control boards 31 and instrument controller 28 to selectively actuate the tool 20.

The input module assembly 260 includes the trigger 298 in communication with trigger sensor TS. The trigger sensor TS is connected with the input device flexible circuit 370 of the flexible circuit assembly 310 to send positional information of the magnet TM in the form of electrical signals to the control boards 31. The input module assembly 260 includes one or more trigger sensors TS operatively connected with the input device flexible circuit 370 for monitoring the portion of the trigger 298 (via the trigger magnet TM) relative to the one or more trigger sensors TS. In some examples, such as shown in FIGS. 39 and 40, the input module assembly 260 includes a trigger 298 with a trigger magnet TM which is configured to be sensed by the trigger sensor TS. The trigger sensor TS may be configured as a Hall-effect sensor, however, other types of sensors and methods of sensing are contemplated. Furthermore, while it is contemplated that the input device may include the trigger in some implementations, and hence referred to as including a trigger sensor and a trigger magnet, it some implementations, another movable component may replace the trigger, and may utilize a sensor and a magnet as described with respect to the trigger and trigger sensor.

The hand-held portion 16 may include a tensioning assembly 266, 410 for selectively adjusting the length of the input device flexible circuit 370 that is disposed between the hand-held portion 16 and the tool support 18 depending on the variable position of the tool support 18 relative to the hand-held portion 16. The tensioning assembly guides the input device flexible circuit 370 while the instrument is moved in a plurality of degrees of freedom, maintaining the connection of the input device flexible circuit 370 with the input module assembly 260. In other words, the tensioning assembly 266, 410 may function to control the length of the input device portion 380 of input device flexible circuit 370 available between the hand-held portion 16 and the tool support 18 when the tool support 18 and the hand-held portion 16 are moved relative to each other by the plurality of actuators. The tensioning assembly 266 applies a force against the input device portion 380 of input device flexible circuit 370 through contact so that any slack is taken up in the input device flexible circuit 370 to avoid kinking and pinching as the instrument moves through its range of motion. Additionally, when the tool support 18 is moved relative to the hand-held portion 16 and requires more of the available flexible circuit length 380, the tensioning assembly 266, 410 allows the input device portion 380 of the input device flexible circuit 370 pass through, providing the additional length for the full range of movement of the instrument 14. As described above, the input flex guide assembly 340 guides and routes the input device flexible circuit 370 to the tensioning assembly 266, 410. The input flex guide assembly 340 provides support to the input device flexible circuit 370 when the tool support 18 is moved to compensate for both elevation and pitch as the tensioning assembly 266, 410 adjusts the available length of input device flexible circuit 370. As can be seen in FIGS. 39-40 and 42-43, the tensioning assembly 266, 410 may be disposed within housing 264, 412. Alternative locations are also contemplated, such as on the tool support.

In one example seen in FIGS. 339-41, the tensioning assembly 266 includes routing members 268 and biasing members 270. The biasing member 270 may also be referred to as a tension member. In some examples, the routing members 268 are stationary or fixed on the biasing member, allowing the input device flexible circuit 370 of the flexible circuit assembly 310 to slide around the perimeter of the routing members 268. In other examples, the routing members 268 are configured as roller members so that the input device flexible circuit 370 glides about the routing members 268.

As best seen in FIG. 41, the biasing members 270 of the tensioning assembly 266 are used to apply a force against the input device flexible circuit 370 such that when the tool support 18 is moved in a direction toward the hand-held portion 16, the biasing members 270 exert a force onto the input device flexible circuit 370, pushing the excess material of the input device flexible circuit 370 about the routing members 268 into the boreholes 272, taking up the slack of the portion 380 of the input device flexible circuit 370. When the tool support 18 is moved away from the hand-held portion 16, the input device elongated portion 380 applies a force greater than that of the biasing members 270, depressing the biasing members 270 and rolling around the routing members 268 to allow the extra length of the input device flexible circuit 370 to compensate for the z-axis translation of the tool support 18 relative to the hand-held portion 16. In this configuration, the routing members are arranged to form a non-linear path which the flexible conductor or flexible circuit is routed about.

In certain instances, the tensioning assembly 266 may be used for flexible circuits FC for other components of the instrument 14. For example, the tensioning assembly 266 may be used for actuator flexible circuits 330, 332, 334 in certain implementations, for input devices other than triggers, and for sensors used for sensing a characteristic of the instrument other than the position of the actuators or the trigger, such as force sensors, gyroscopes, displacement sensors, temperature sensors, inertial sensors, and the like.

Another example of a tensioning assembly 410 is illustrated in FIGS. 42-50E. The input module assembly 260 includes the tensioning assembly 410. The tensioning assembly 410 includes a housing 412 with a swing arm 424 connected with a biasing member 416, the biasing member 416 located between the swing arm 424 and the housing 412. The tensioning assembly 410 may function to apply a tensioning force onto the input device portion 380 of flexible circuit 370 as the instrument 14 is moved in a plurality of degrees of freedom. The tensioning assembly 410 may function to take up the additional length of the input portion 380 of input device flexible circuit 370 that is disposed between the hand-held portion 16 and the tool support 18 when the tool support 18 and the hand-held portion 16 are in poses where the full length of the input portion 380 of input device flexible circuit 370 is not needed.

Figure 44:
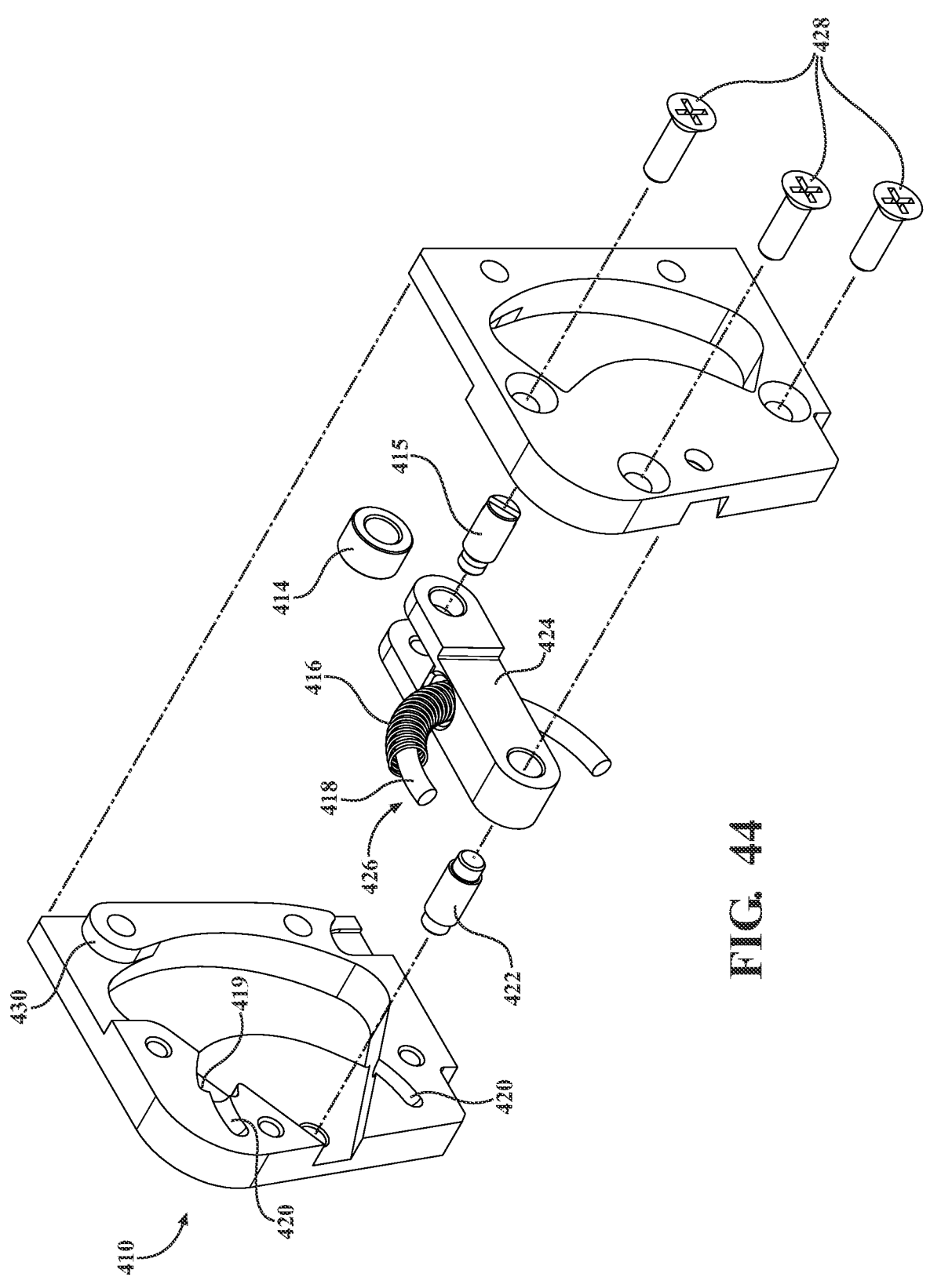
FIG. 44 illustrates an exploded view of the tensioning assembly of FIGS. 40 and 41.
Figure 45:
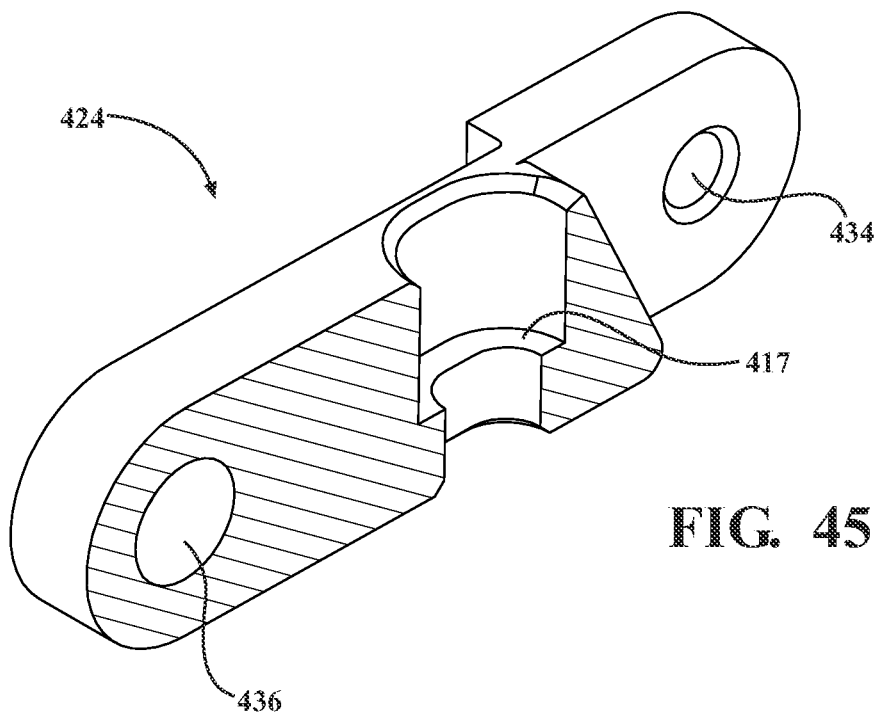
FIG. 45 illustrates a cross sectional view of a swing arm.
Figure 46:
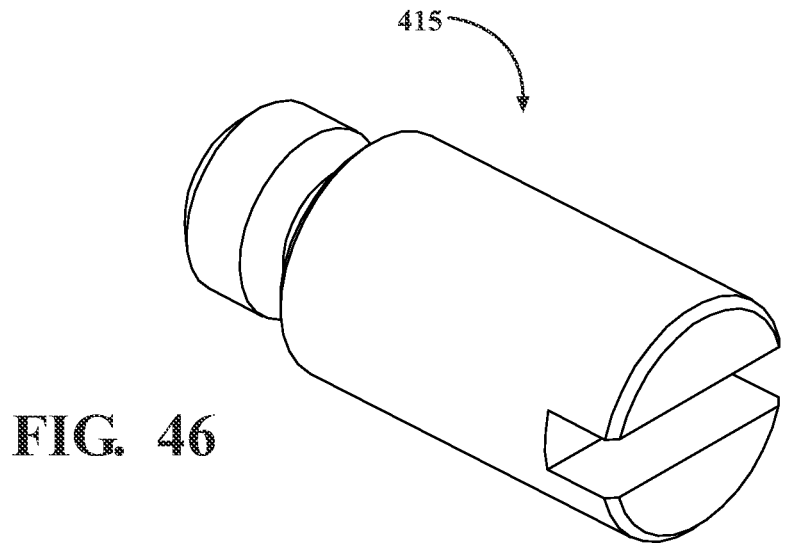
FIG. 46 illustrates a pivot pin.

The housing 412 of the tensioning assembly 410 functions to hold the moving elements of the tensioning assembly 410 and provide areas 430, 432 formed into the housing for routing the input device flexible circuit 370 to the input device sensor S. The housing 412 may be formed in two parts and secured together using fasteners 428. As best seen in FIG. 44, the tensioning assembly 410 is shown in an exploded view. The housing 412 is formed with mounting areas 419, 420 which are shaped to accept the biasing member 416 and guide member 418, respectively. To allow the swing arm 424 move to assist with the management of the input device flexible circuit 370 during tool movement, the housing 412 is forms an aperture 426 corresponding to the range of motion of the swing arm 424, opposite of the mounting location 436 of the swing arm 424.

The swing arm 424 is pivotally connected with the housing 412 of the tensioning assembly 410 by a pivot pin 422, a pivot connection. The swing arm 424 is in communication with the biasing member 416, the biasing member 416 providing a force onto the swing arm to tension the input device flexible circuit 370 during movement of the tool support 18. The swing arm 424 may also be referred to as a tension member. The swing arm 424 includes a routing member 414 coupled to the swing arm 424 by a roller pin 415, with the routing member being disposed on the end of the swing arm opposite the pivot connection. The roller pin 215 is connected to the swing arm 424 at the roller axis mount 434. The swing arm 424 moves about pivot pin 422 along the aperture 426 of the housing 412 as the routing member 414 interacts with the input device flexible circuit 370.

The routing member 414 is connected with one end of the swing arm 424. In some configurations, such as shown in FIGS. 42-45 and 47-50E, the routing member 414 is rotatable about roller pin 415 to reduce drag on the input device flexible circuit 370 as the tensioning assembly 410 increases and decreases the available length of input device portion 380 of input device flexible circuit 370 during instrument movement. In other examples, the routing member 414 may be stationary relative to the swing arm 424. The input device flexible circuit 370 is routed around the routing member 414 such that the swing arm 424 applies a force through the routing member 414 onto the input device flexible circuit 370.

The tensioning assembly 410 includes a guide member 418 within the housing 412. The guide member 418 has a curvature that is concentric to a movement of the swing arm 424 and to the shape of the aperture 426 in the housing 412. For example, the swing arm 424 attaches at the pivot pin 422 which creates the center point of at least a portion of a circle having a radius corresponding to the length of the swing arm 424. The guide member 418 is positioned such that a portion of the swing arm 424 rides along the guide member 418. The guide member 418 has a shape that is concentric to the radius that the swing arm 424 forms when pivoting about the pivot pin 422 so that the swing arm 424 rides along the guide member 418 within the housing 412. In some examples, the guide member 418 is retained in the housing 412 at the guide mounts 420. As seen in at least FIGS. 43 and 44, the swing arm 424 is disposed around the guide member 418, the guide member 418 providing a path for the biasing member 416 between the housing 412 and the swing arm 424. The biasing member 416 is located between the housing 412 and the swing arm 424 of the tensioning assembly 410. The biasing member 416 may function to apply a force onto the swing arm 424 to apply a force onto the input device portion 380 of input device flexible circuit 370 to allow for changes in length to the input device portion 380 and to reduce any slack present in the input device portion 380 of input device flexible circuit 370 during tool movement in the plurality of degrees of freedom. In some examples, the biasing member 416 may be at least partially compressed throughout the entire range of motion of the swing arm 424. The biasing member 416 is shown as a coil spring, however other suitable biasing members are contemplated, such as a torsion spring.

Figure 47:
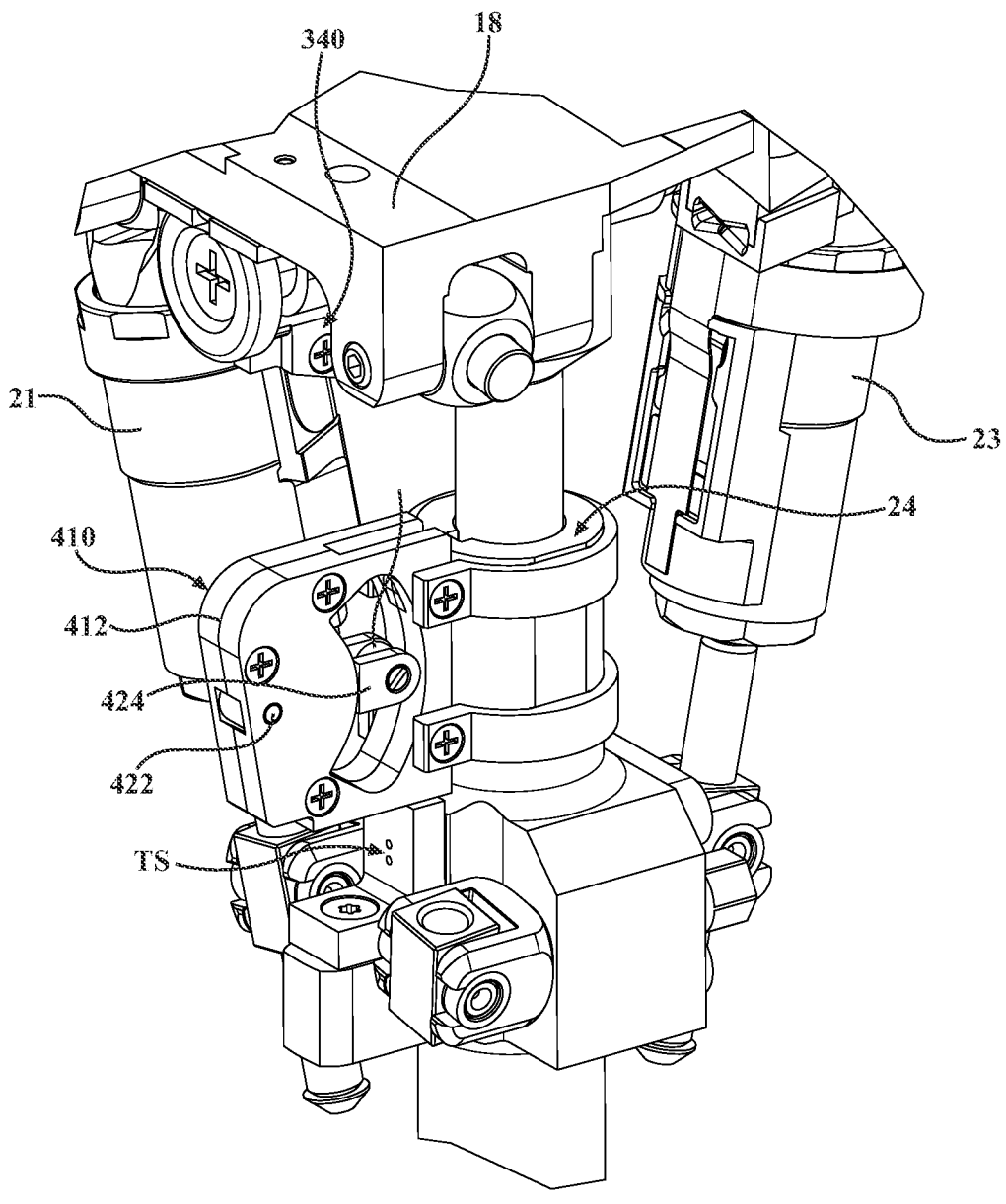
FIG. 47 illustrates a partial schematic view of the tensioning assembly of FIG. 40 in a portion of the instrument.
Figure 48:
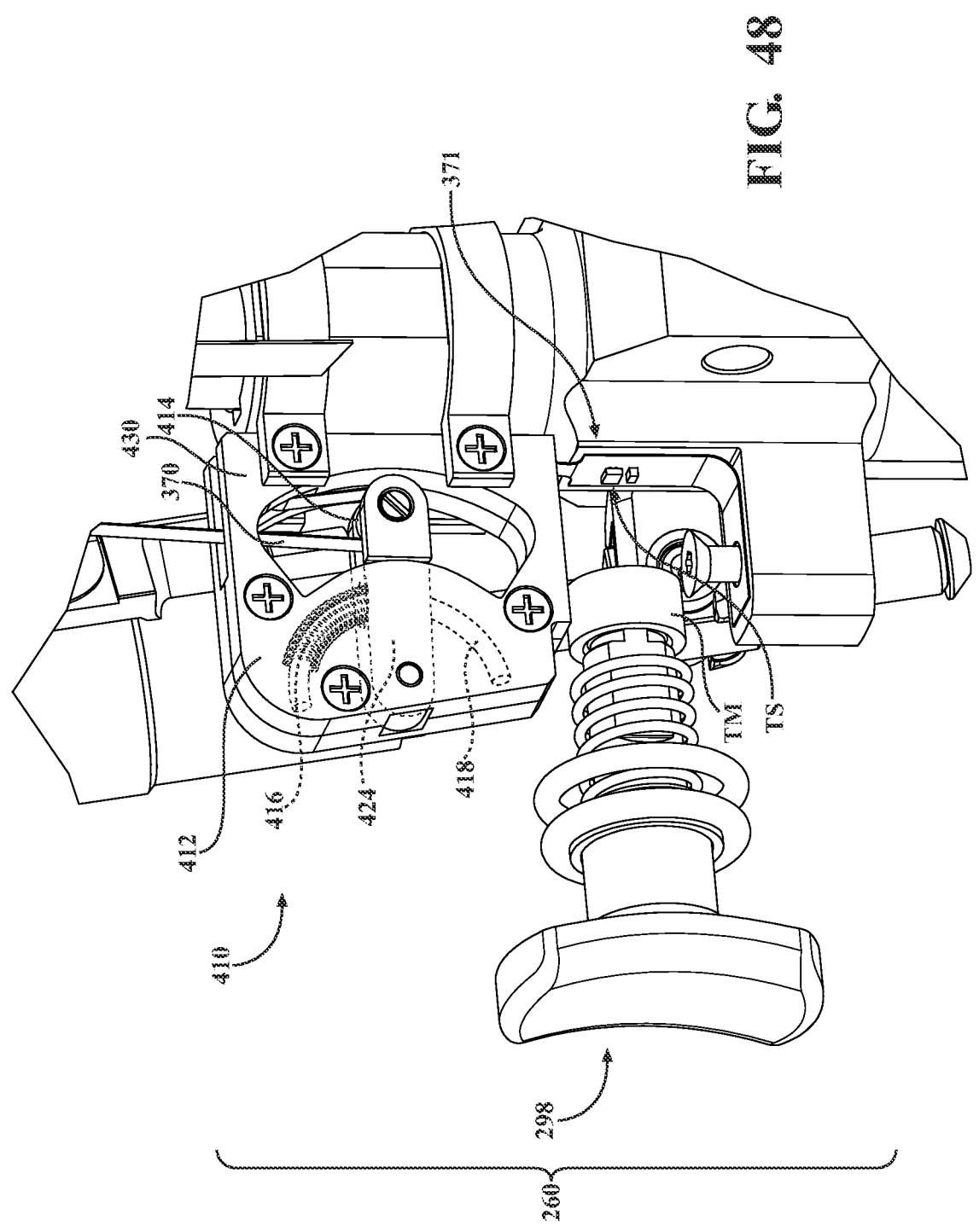
FIG. 48 illustrates the tensioning assembly of FIG. 40 with an input device on the instrument.
Figures 49A, 49B:
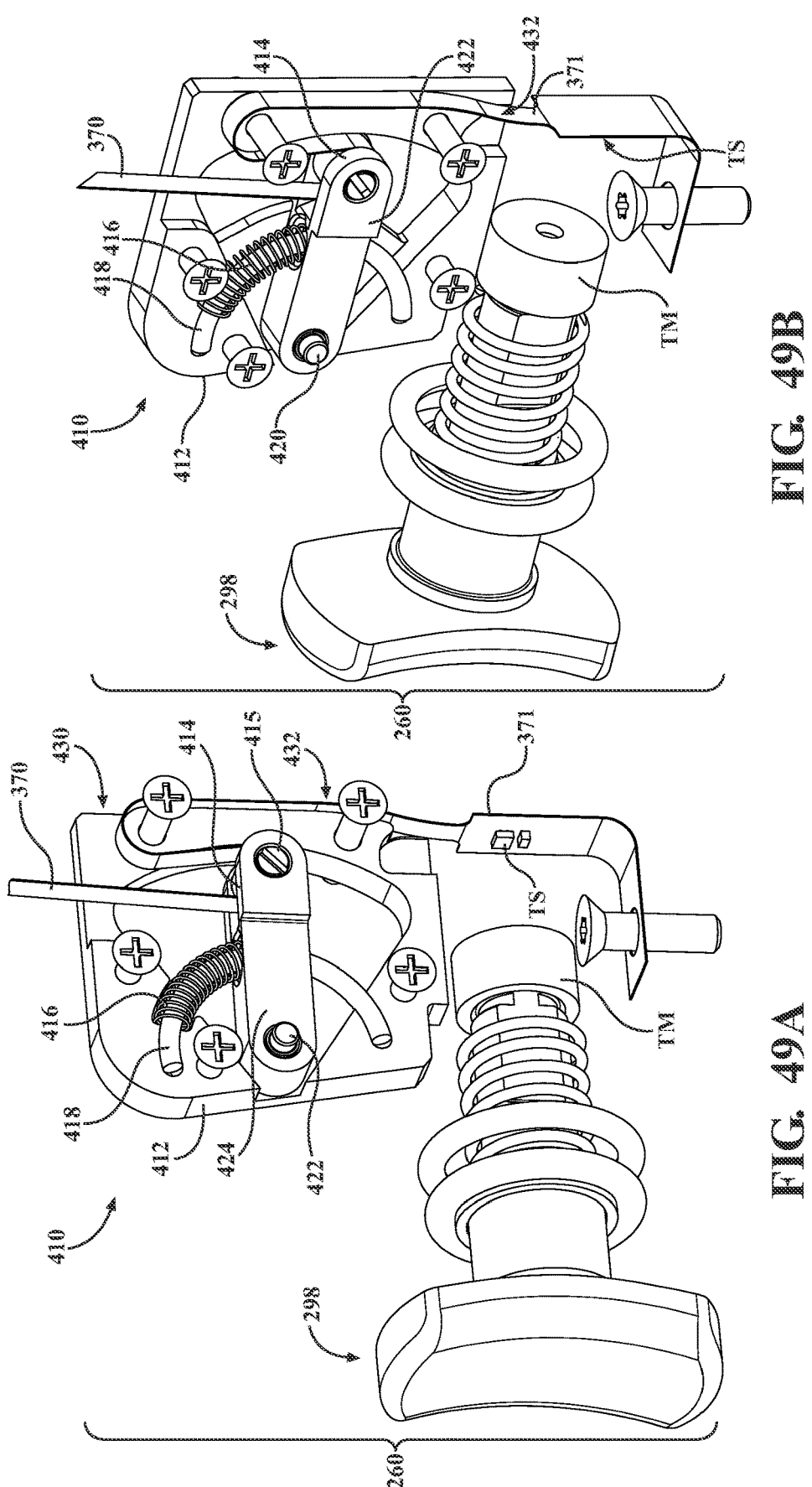
FIGS. 49A and 49B illustrate perspective views of the tensioning assembly of FIG. 42 with an input device on the instrument.

In some examples, the tensioning assembly 410 is connected to the instrument 14 in the hand-held portion 16, attaching to the constraint assembly 24 and adjacent to the input sensor TS (FIG. 47). FIGS. 48 and 49A-49B show the routing of the input device flexible circuit 370 through the tensioning assembly 410. The input device flexible circuit 370 is routed through the top of the housing 412, around the routing member 414, along the routing areas 430, 432 of the housing 412 connecting to the sensor S. In other examples, the tensioning assembly 410 may be connected to the tool support 18. Put another way, the tensioning assembly 410 is connected to either the tool support 18 or the hand-held portion 16, and the instrument controller 28 is located on the other of the tool support 18 or the hand-held portion 16.

Figures 50A, 50B:
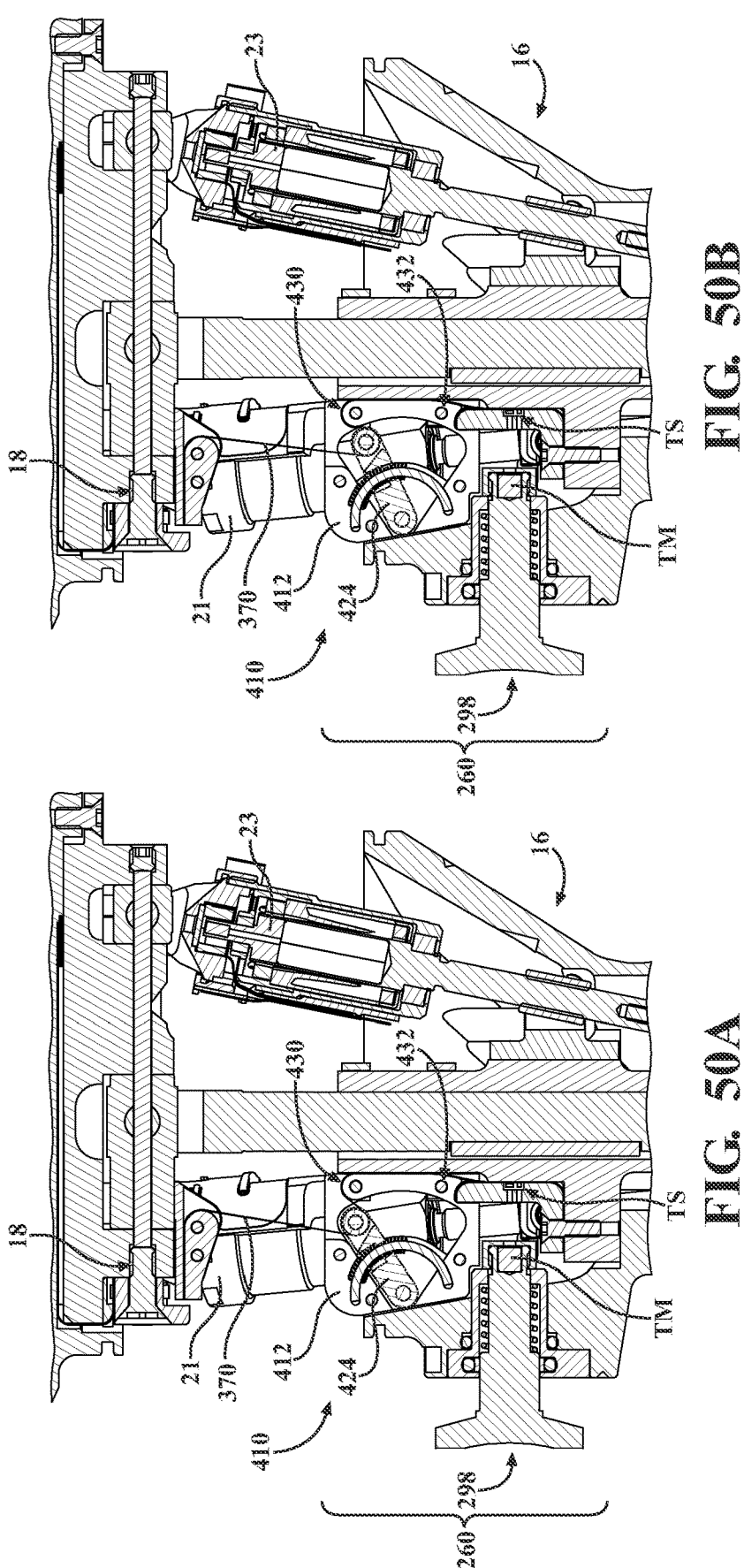
FIGS. 50A-50E illustrate different cross-sectional views of the tensioning assembly of FIG. 42 integrated into the instrument with flexible circuits.

Turning to FIGS. 50A-50E, the tensioning assembly 410 is shown adjusting the tension of the flexible circuit 370 as the tool support 18 is moved relative to the hand-held portion 16 through a plurality of degrees of freedom. FIG. 50A shows the tool support 18 elevated with actuators 21, 23 adjusted away from the hand-held portion 16, pulling the input device flexible circuit 370 upwards with enough force to overcome the biasing member 416. The swing arm 424 is pulled in the same direction as the actuators 21, 23. In the examples shown in FIGS. 50A-50E, although unshown, actuator 22 is assumed to be in the same position as actuator 21, with both actuators 21, 22 working in concert with each other. In other words, FIGS. 48A-48E do not depict a roll condition of the tool support 18.

FIG. 50B displays the tool support 18 in a pitched up condition relative to the hand-held portion 16. Since the front actuator 21 is substantially extended, the input device flexible circuit 370 is pulled in the same direction, overcoming the force of the biasing member 416, pulling the swing arm 424 in the same direction.

Figures 50C, 50D, 50E:
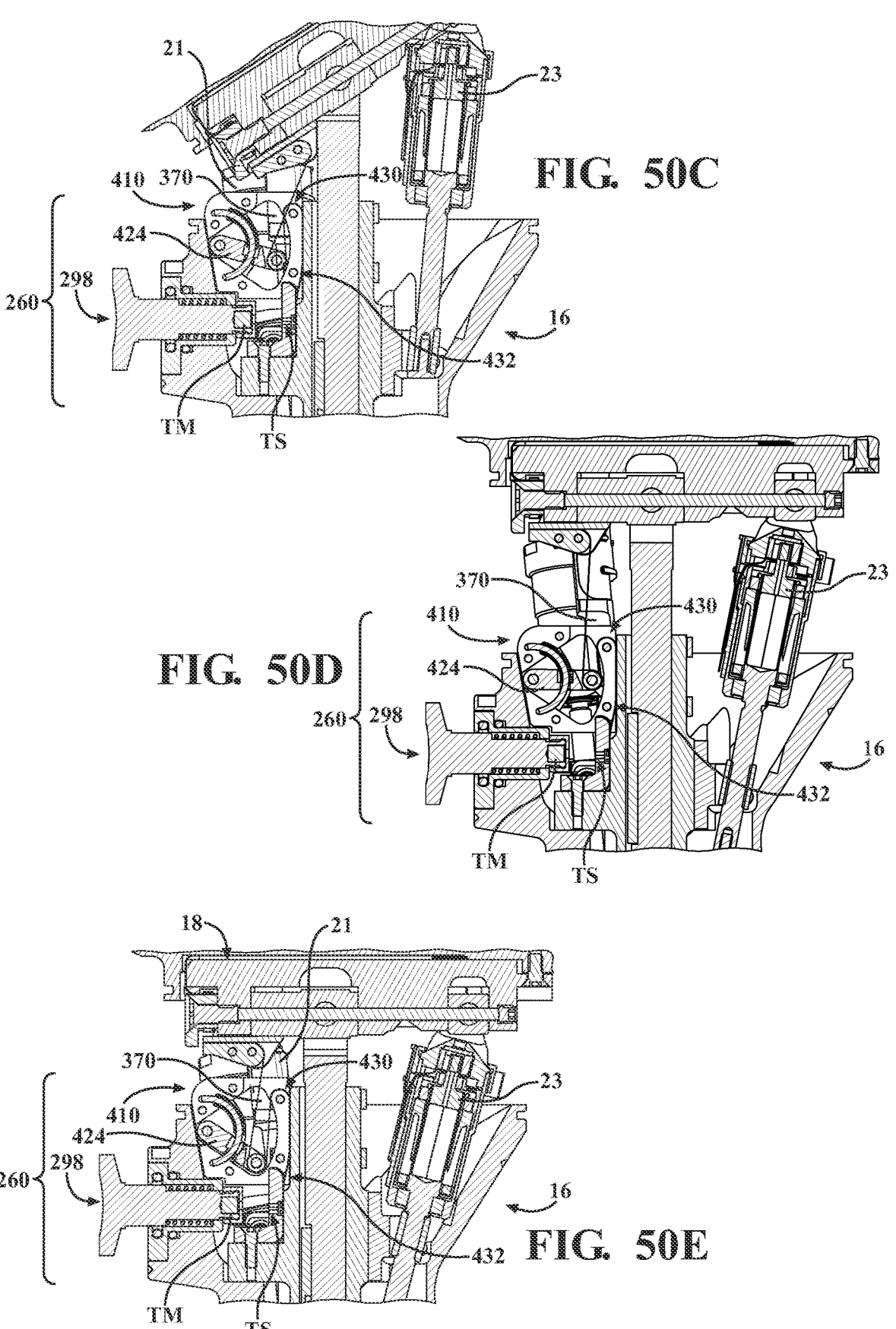
Figure 51:
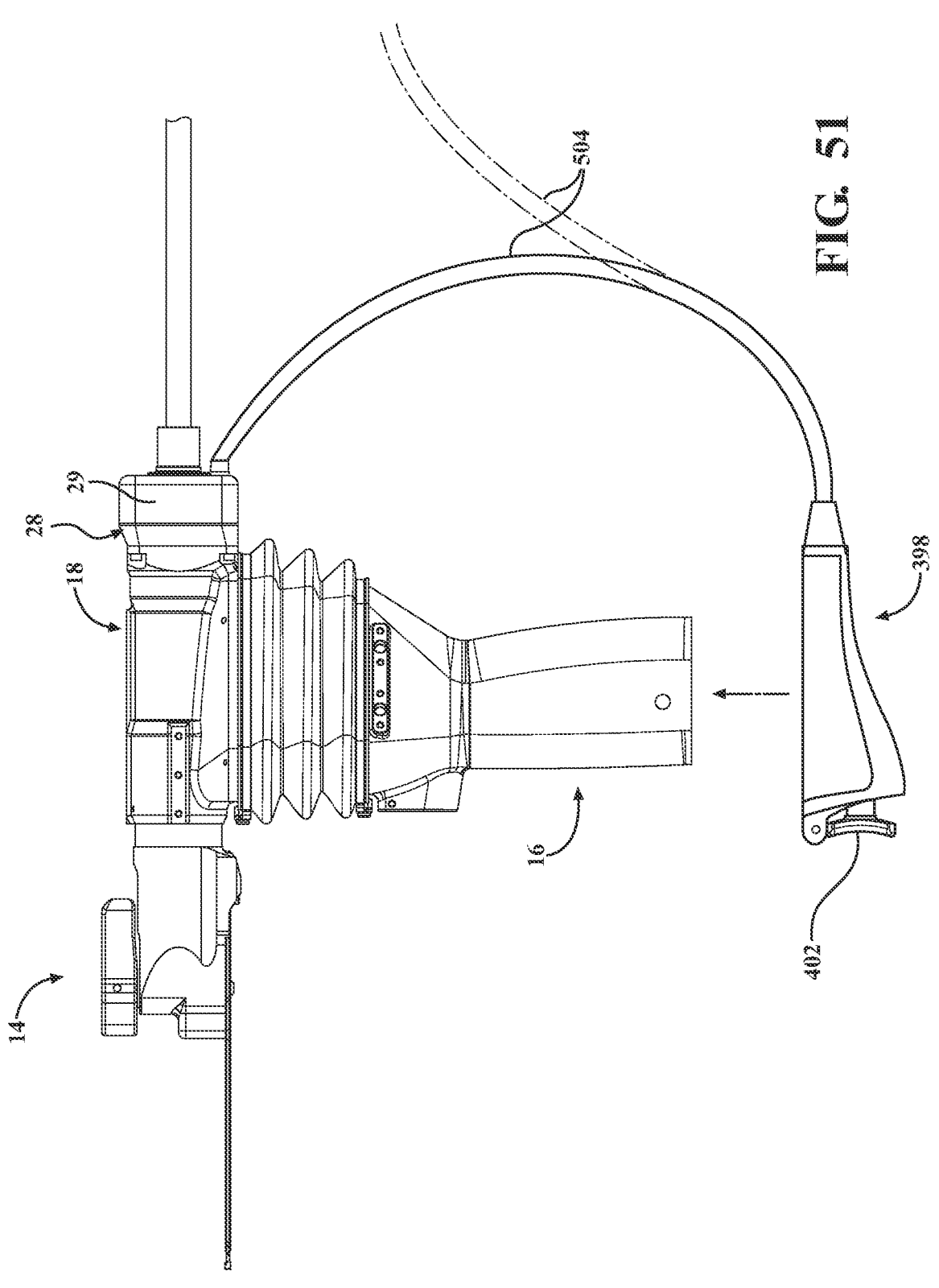
FIGS. 51 and 52 depict one configuration of the robotic instrument consistent with the teachings herewith.
Figure 52A:
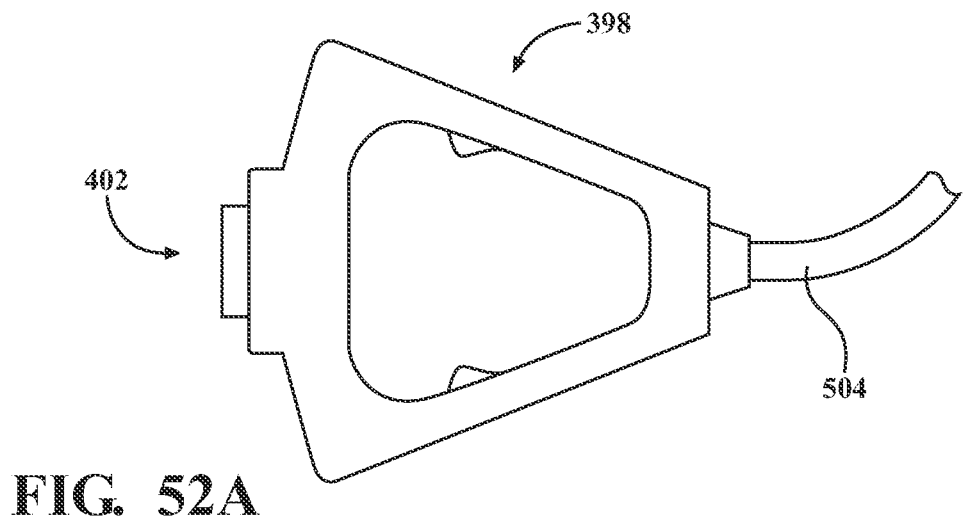
Figure 52B:
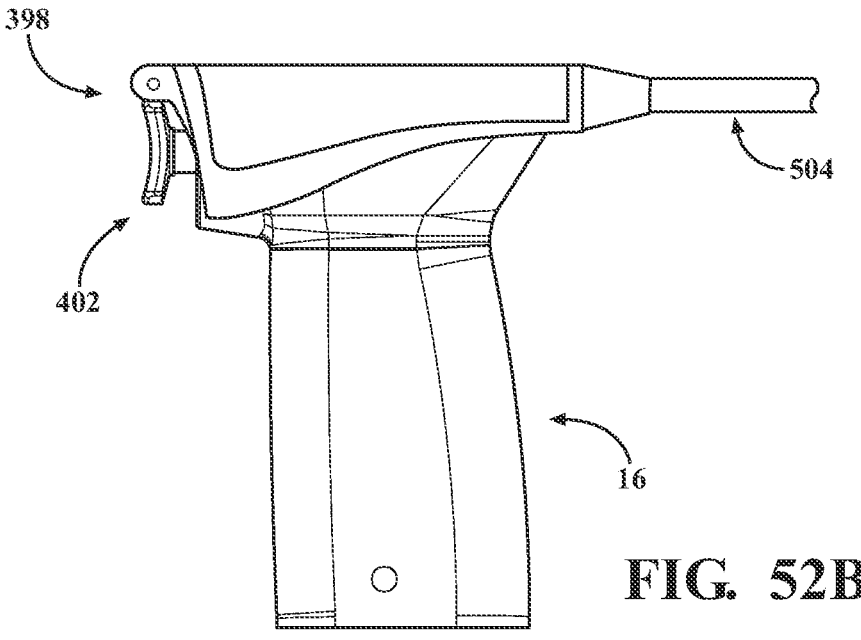
Figure 53:
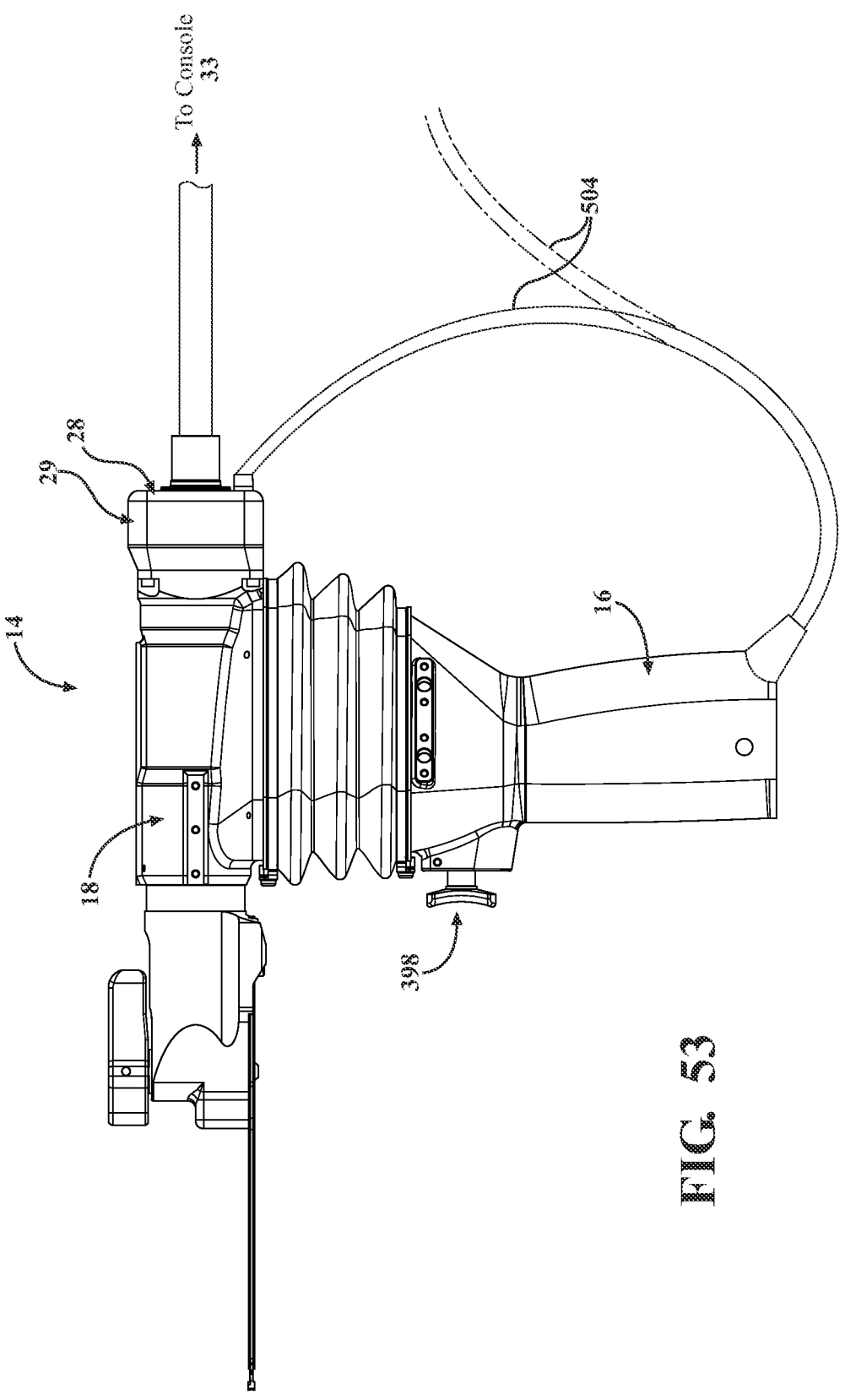
FIG. 53 depicts one configuration of the robotic instrument consistent with the teachings herewith.

FIG. 50C illustrates the tool support 18 in a pitched down configuration, bringing actuator 21 close to the hand-held portion 16 while actuator 23 is extended away from the hand-held portion 16, causing the input device portion 380 of input device flexible circuit 370 to increase the available length of the flexible circuit portion 380 to accommodate the tool support 18 movement. In this pose, the biasing member 416 is partially compressed and applies a force against the swing arm 424 to place a tensioning force onto the input device flexible circuit 370 so that any slack is taken up in the input device flexible circuit 370 to avoid kinking and pinching.

Similarly, FIG. 50D depicts the tool support 18 in a position with a maximum range of motion with the actuators 21, 23 at their respective home positions. In this pose, the biasing member 416 is in a partially compressed state, and the swing arm 424 is applying a tension onto the input device flexible circuit 370.

FIG. 50E illustrates the tool support 18 close to the hand-held portion 16 with the actuators 21, 23 collapsed. In this pose, the swing arm 424 is fully extended with the biasing member 416 in an expanded state. As can be seen in FIGS. 50A-50E, as the tensioning assembly 410 adjusts and routes the input device flexible circuit 370, the input device flexible circuit 370 travels along a non-linear path as the tool support 18 is moved relative to the hand-held portion 16.

Turning to FIGS. 51-54, alternative configurations of the input device arrangement 398, 498 are contemplated. In the example shown in FIGS. 51 and 52, the input device 398 is configured as a removably connected assembly with the hand-held portion 16. The input device 398 includes a trigger and corresponding sensors/encoders (not shown) within the hand switch assembly 402 for monitoring the position of the input device 398. In some examples, the hand switch assembly 402 is configured to be sterilizable. In other examples, the hand switch assembly 402 is configured to be disposable. The hand switch assembly 402 may include one or more locking members for securing the hand switch assembly to the hand-held portion 16. In some examples, the hand switch assembly 402 may require a release button to remove the hand switch assembly 402 from the instrument 14.

The hand switch assembly 402 slides over the hand-held portion 16 and includes connection cable 404 connecting with the control housing 29, the console 33, or both. By connecting directly with the control housing 29, the console 33, or both, a flexible circuit from the tool support into the hand-held portion 16 is not required to monitor the position of the input device 398.

Figure 55:
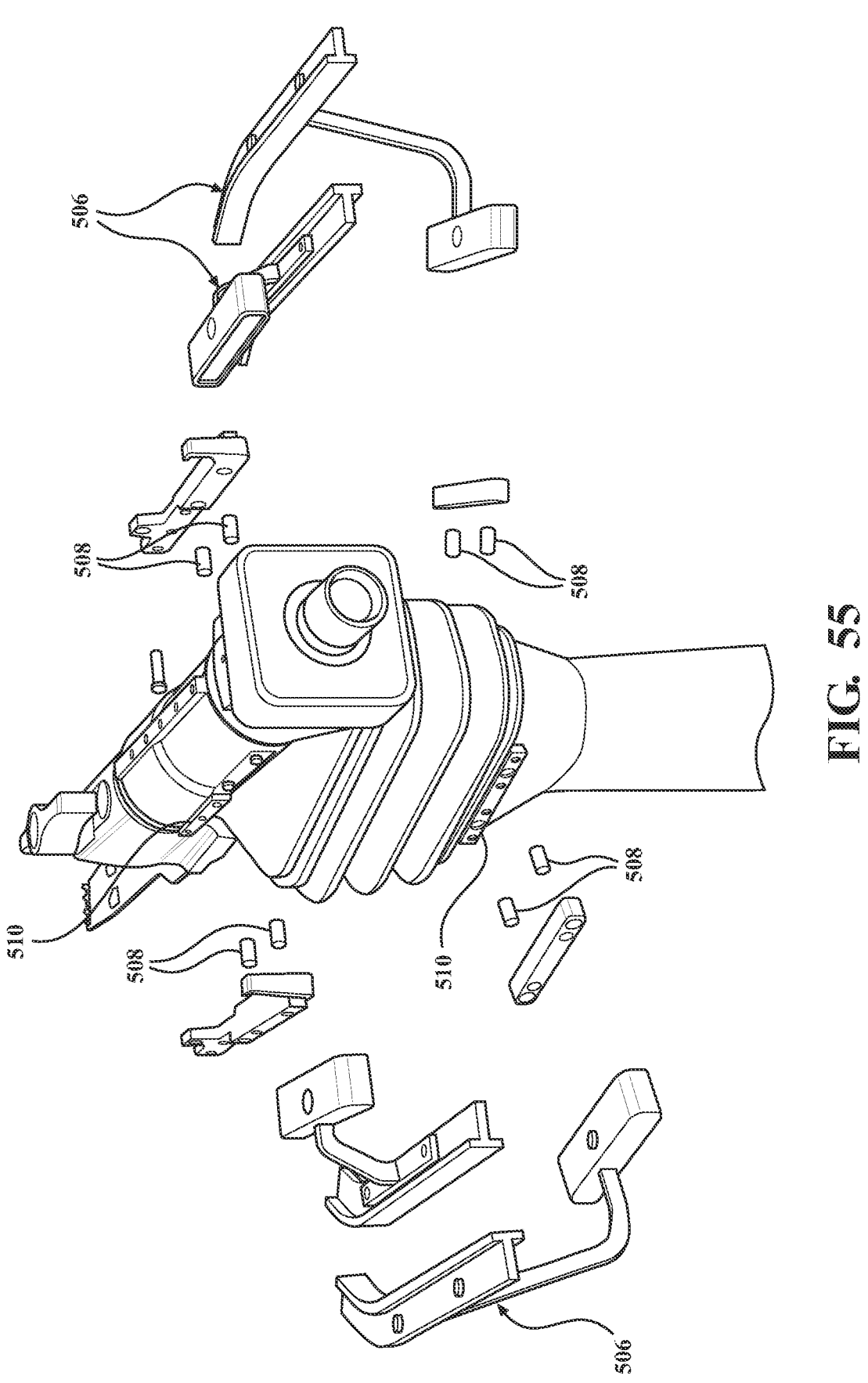
FIG. 55 depicts the robotic instrument and one or more removable accessories that are removably secured to the hand-held portion or the tool support using a magnetic field.

In one example, shown in FIG. 55, the instrument is configured such as previously described, however, a connection cable 504 may be routed outside the instrument 14 between the tool support 18 and the hand-held portion 16 to avoid clearance issues associated with routing wires and/or flexible circuits FC internally. The connection cable 504 may be connected with the control housing 29, the console 33, or both.

Figure 54A:
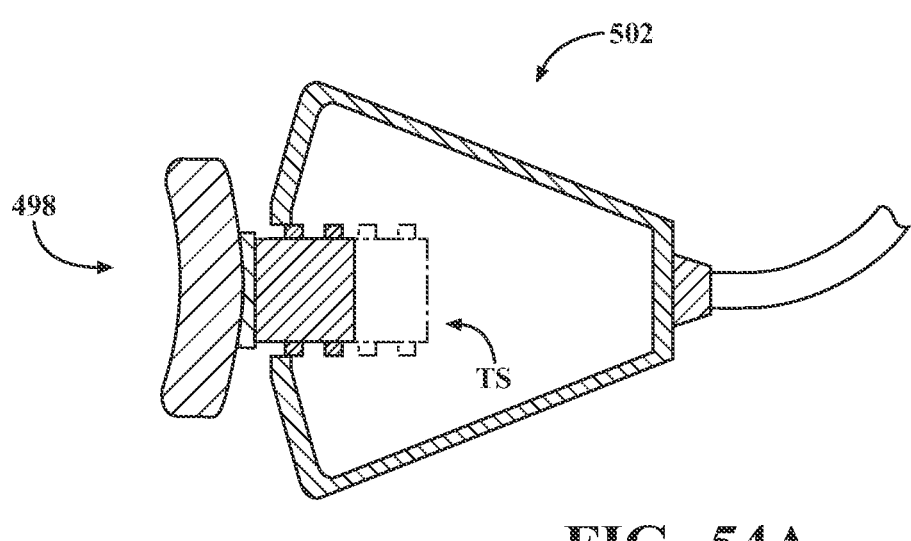
FIG. 54 depicts one configuration of an input device assembly consistent with the teachings herewith.
Figure 54B:
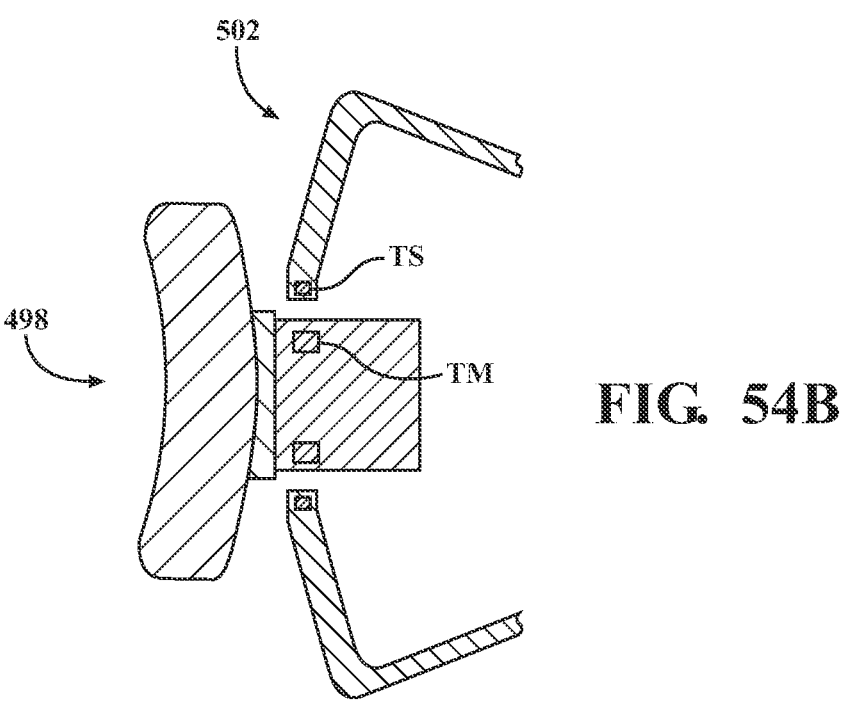

In another configuration, shown in FIG. 54, the hand switch assembly 502 is shown as an external sensor TS which monitors the movement of an input device 398 integrated within the hand-held portion 16. The external encoder (trigger sensor) TS reads the position of the trigger magnet TM located on the end of the trigger and sends the signal to the control boards 31, the console 33, or both. In some examples, the hand switch assembly may be configured to be a disposable component. It is contemplated that additional buttons and functionalities may be added to the external device. For example, a button or switch may be configured to cycle between operational modes.

Referring again to FIGS. 11 and 37, it is contemplated that use of a linkage formed from ferromagnetic material may provide advantageous magnetic isolation for the various sensors that are utilized in the robotic hand-held instrument, particularly the trigger sensor. Because the controller utilizes the input signal provided by the trigger sensor to control the drive motor to move the tool, such as the surgical saw, inadvertent activation of the trigger sensor can cause inadvertent activation of the drive motor, which results in unintended motion of the tool. This unintended motion of the tool can be problematic. Commonly, trigger sensors are hall-effect sensors which are triggered by the presence of the magnetic field. Because the instrument may include several magnets as part of several components, the magnetic field from a component other than the trigger may affect the hall-effect sensor which functions as the trigger sensor. Some of the components of the instrument that may generate magnetic fields include, but are not limited to, the plurality of actuators used in the actuator assembly, one or more removable accessories 506 that are removably attached to the hand-held portion and/or the tool support.

In addition to providing advantageous magnetic isolation to the trigger sensor, the construction of the instrument may further provide magnetic isolation for other sensors included in the instruments, such as the actuator sensors that are used to determine the position of the actuators. For example, it is contemplated that the presence of magnetic fields generated by magnets included in components other than a particular actuator may affect the actuator sensor. These components may be the magnet included as part of the trigger assembly, other actuators that include one or more magnets, or one or more removable accessories 506 that are removably attached to the hand-held portion and/or the tool support.

More particularly, the linkage may include multiple components, wherein at least one component of the linkage is formed from a ferromagnetic material. As described with respect to FIG. 11, the linkage 26 may comprise a shaft 174 and a sleeve 76, which is configured to receive the shaft 174 along an axis. The linkage is configured to allow the shaft 174 to slide axially along the axis relative to the sleeve 76. In certain configurations, the linkage is configured to constrain movement of the shaft radially relative to the constraint axis during actuation of one or more of the plurality of actuators. More generally, the linkage may be coupled to the tool support and the hand-held portion in a manner configured to constrain movement of the tool support relative to the hand-held portion in at least one degree of freedom, such as one, two, or three degrees of freedom.

The ferromagnetic material of the component of the linkage has a saturation magnetization of greater than 0.5 Tesla. Alternatively, the ferromagnetic material of the component of the passive linkage may have a saturation magnetization of greater than 0.6, 0.7, 0.8, or 0.9 Tesla. This level of saturation magnetization provides an ability to absorb the stray magnetic field without saturating. Alternatively, or in addition to the saturation magnetization property, the ferromagnetic material of the component of the linkage has maximum relative permeability of greater than 100. Alternatively, the ferromagnetic material of the component of the linkage may have a maximum relative permability of greater than 300, 500, 1000, 1500, or 2000. In one configuration, where the linkage includes a shaft and a sleeve 76 configured to receive the shaft, the shaft is formed from the magnetic material having a saturation magnetization of greater than 0.5 Tesla and a maximum relative permeability of greater than 100. Exemplary ferromagnetic materials is 17-4 stainless steel, pure iron, amorphous steel, nanocrystalline steel, Mu Metal, Permalloy, or Permendur. Thus, it is contemplated that the shaft is formed from 17-4 stainless steel. The sleeve 76 may not necessarily be formed from ferromagnetic material, but may be in certain embodiments. In one configuration, the sleeve 76 may be formed from an aluminum-silicon-bronze alloy 642. The ferromagnetic material in the linkage creates a magnetic flux path extending from the tool support to the hand-held portion, thereby providing advantageous magnetic isolation.

It is contemplated that construction of one or more of the plurality of actuators of the actuator assembly may provide further magnetic isolation to one or more sensors included in the instrument. In such an implementation, at least one component of the actuator housing is formed from a ferromagnetic material. Referring to FIG. 11 again, each of the actuators comprises a housing 134. The housing may include a canister 136 and a cap 138 threadably connected to the canister 136. The cap 138 may capture the annular shoulders of the pivot yokes to secure the pivot yokes to the canisters, but the cap may be configured in an alternative matter. The lead screw 150 is movably coupled to the housing 134. The canister 136 may be formed from a ferromagnetic material, whereas the lead screw 150 and the cap 138 need not necessarily be formed from a ferromagnetic material. For example, the canister 136 may be formed from a 17-4 precipitation hardened stainless steel (a ferromagnetic material), whereas the cap 138 may be formed from a 303 stainless steel (nonmagnetic) and the lead screw may be formed from Nitronic 60 (a non-magnetic stainless steel alloy). The canister 136 may be formed from a ferromagnetic material having a saturization magnetization of greater than 0.5 Tesla and/or a relative maximum permeability of greater than 100.

As shown in FIG. 55, the hand-held robotic instrument may include one or more removable accessories 506 that is removably secured to one of the hand-held portion 16 or the tool support 18 using a magnetic field. The removable accessory 506 may be a plane alignment device for facilitating the positioning of instrument relative to a planned virtual object. The removable accessory 506 may include a magnet 508 or a ferromagnetic member 510 and the hand-held portion 16 and/or the tool support 18 may include a ferromagnetic member 510 or a magnet 508, with the understanding that at least one of the removable accessory 506 and the instrument will including a magnet 508. The presence of an additional magnet field through use of a removable accessory 506 may have tendency to further affect the sensors described above in the absence of the described techniques to provide magnetic isolation.

It should be understood that the combination of position and orientation of an object is referred to as the pose of the object. Throughout this disclosure, it is contemplated that the term pose may be replaced by position and/or orientation in one or more degrees of freedom and vice-versa to achieve suitable alternatives of the concepts described herein. In other words, any use of the term pose can be replaced with position and any use of the term position may be replaced with pose.

The flexible circuit and/or flexible conductor may take different forms. In certain configurations, the flexible conductor may be a wire or ribbon of a plurality of conductors. In other configurations, the flexible conductor may take the form of a printed flexible circuit board. It should be understood that the flexible circuits described throughout may each independently include one or more rigid portions, such as rigid panels. Thus, throughout this disclosure, any instance of flexible circuit is contemplated to be replaced by flexible conductor.

The flexible circuits can include one or more electronic devices on a plastic substrate, such as polyimide, PEEK, polyethylene naphthalate, polyetherimide, transparent conductive polyester, fluoropolymers, or mixtures thereof. The flexible circuit can be made using photolithographic technology. The flexible circuit construction may be more lightweight and smaller, facilitating a more compact and lightweight hand-held robotic instrument. The flexible circuits can be single or double-sided. The flexible circuits may include a metal foil, where the circuits paths are etched.

Several embodiments have been described in the foregoing description. However, the embodiments discussed herein are not intended to be exhaustive or limit the invention to any particular form. The terminology, which has been used, is intended to be in the nature of words of description rather than of limitation. Many modifications and variations are possible in light of the above teachings and the invention may be practiced otherwise than as specifically described.

I. A hand-held surgical robotic system for supporting a surgical tool, the hand-held surgical robotic system comprising a hand-held portion; a tool support movably coupled to the hand-held portion, the tool support configured to support the surgical tool and further comprising a tool drive motor; a plurality of actuators operatively interconnecting the tool support and the hand-held portion, the plurality of actuators configured to move the tool support relative to the hand-held portion in one or more of degrees of freedom; a controller on the tool support, the controller in communication with the tool drive motor and each actuator of the plurality of actuators and a plurality of flexible circuits connecting the instrument controller with each of the plurality of actuators, wherein the plurality of flexible circuits maintain the connection between the instrument controller and the plurality of actuators while the tool support is moved in the plurality of degrees of freedom relative to the hand-held portion.

II. The system of clause I, wherein the each of the plurality of flexible circuits have a width and a thickness, wherein the width is at least eight times greater than the thickness.

III. The system of any preceding clauses, wherein at least one of the plurality of flexible circuits has a longitudinal axis, and the at least one of the plurality of flexible circuits extend from a coupling point on one of the plurality of actuators and engaging a flex guide on one of the tool support and the hand-held portion to minimize deformation of the at least one flexible circuit in one or more degrees of freedom, and optionally, at least one of the plurality of actuators are coupled to the tool support at a pivot axis, wherein the flex guide is positioned such that the longitudinal axis of the at least one flexible circuit is aligned with a center point of the pivot axis IV. The system of any preceding clauses, wherein the plurality of flexible circuits connect with the plurality of actuators at a portion of each of the actuators that is connected with the tool support.

V. The system of clause IV, wherein the plurality of flexible circuits includes a first flexible circuit, and wherein the plurality of actuators includes a first actuator, the first actuator including a lead screw, a motor, and a housing, the motor disposed within the housing, the lead screw being connected to the hand-held portion, and the housing being connected to the tool support, with the first flexible circuit extending from the housing to the instrument controller.

VI. The system of clause V, wherein the housing of the first actuator includes a connector, and the first flexible circuit is routed to and coupled to the housing with the connector.

VII. The system of clause VI, wherein the first flexible circuit includes a length that is wrapped about a circumference of the first actuator, the length of the first flexible circuit is wrapped at least three-quarters of a rotation, the length that is wrapped about the circumference of the first actuator provides the first flexible circuit enough length to maintain the connection with the first actuator while the tool support is moved relative to the hand-held portion in the plurality of degrees of freedom without binding and snapping.

VIII. The system of clause VII, wherein the first flexible circuit is wrapped about the circumference of the first actuator at least one and three-quarters rotations.

IX. The system of clause VII, wherein the first flexible circuit includes two or more planar elbows.

X. The system of clause VII, wherein a loop formed by the first flexible circuit is axially aligned with the first actuator.

XI. The system of any preceding clause, wherein the plurality of flexible circuits are arranged between the tool support and plurality of actuators such that roll movement of the flexible circuits is isolated to the movement of the tool support.

XII. A handheld robotic instrument comprising a handheld portion configured to be held by a user and a tool support coupled to the hand-held portion, the tool support comprising a tool drive motor configured to drive motion of the tool, an actuator assembly operatively interconnecting the tool support and the hand-held portion to move the tool support to move the tool in a plurality of degrees of freedom relative to the hand-held portion to align the tool, the actuator assembly including a plurality of actuators, each actuator including a motor and a position sensor, the plurality of actuators including a first actuator and a second actuator; a controller mounted to the tool support, the controller in communication with the tool drive motor and each actuator of the plurality of actuators; and a plurality of flexible circuits including a first flexible circuit extending from the first actuator to the controller, and a second flexible circuit extending from the second actuator to the controller, wherein the tool support includes a flex guide, wherein at least one of the flexible circuits is connected to the flex guide to guide and route the at least one flexible circuit while the tool support is moving in the plurality of degrees of freedom.

XIII The instrument of clause XXII, wherein at least one of the plurality of flexible circuits have a width and a thickness, wherein the width is at least ten times greater than the thickness.

XIV. The instrument of clause XXII or XXIII, wherein at least one of the plurality of flexible circuits has a longitudinal axis, and the at least one of the plurality of flexible circuits extend from a coupling point on one of the plurality of actuators and engaging a flex guide on the tool support, and, optionally, at least one of the plurality of actuators are coupled to the tool support at a pivot axis, wherein the flex guide is positioned such that the longitudinal axis of the at least one flexible circuit is aligned with a center point of the pivot axis to minimize deformation of the at least one flexible circuit in a roll degree of freedom, a pitch degree of freedom, or both.

XV. The instrument of clause XXIII or XIV, wherein the flex guide defines channel including a top surface and a bottom surface.

XVI. The instrument of clause XV, wherein the flex guide is formed with a profile which defines a span of rotation of the flexible circuit during pitch and roll movement.

XVII. The instrument of clause XVI, wherein the width of the plurality of flexible circuits is more narrow than a width of the flex guide, such that the flex guide provides support across the width of the flexible circuit during movement.

XVIII. The instrument of clause XVII, wherein the flex guide defines a channel including a top surface and a bottom surface, the top surface and bottom surface forming the profile of the flex guide that defines the span of rotation of the flexible circuit.

XIX. The instrument of clause XVIII, wherein the top surface and the bottom surface have the same profile.

XX. The instrument of clause XVIII or XIX, wherein the top surface and the bottom surface have different profiles.

XXI. The instrument of clause XX, wherein the profile includes a portion with a first height and a second height, the first height differing from the second height, wherein the first height engages the flexible circuit while the hand-held portion is at a maximum range of movement.

XXII. The instrument of any one of clauses XVIII-XXI, wherein the top surface and the bottom surface each have a protrusion extending a length of the channel forming an angled surface from the protrusion to each side of the channel, the protrusion extending from the bottom surface towards the top surface, and from the top surface toward the bottom surface.

XXIII The instrument of clauses XXII, wherein a thickness of the flexible circuit is less than a distance between the protrusion of the top surface and the protrusion of bottom surface of the channel to allow the flexible circuit to pass through the channel.

XXIV. The instrument of clause XXIII, wherein a center section of the flexible circuit pivots about the protrusion of the top surface and protrusion of the bottom surface while the tool support is moved in the plurality of degrees of freedom.

XXV. A hand-held robotic instrument for use with a tool to perform surgery, the robotic instrument comprising a hand-held portion to be held by a user; a tool support coupled to the hand-held portion, the tool support comprising a tool drive motor to drive motion of a tool, an actuator assembly operatively interconnecting the tool support and the hand-held portion configured to move the tool support in a plurality of degrees of freedom relative to the hand-held portion to align the tool, the actuator assembly including at least one actuator, each actuator including a motor and a position sensor; a controller mounted to the tool support, the controller in electrical communication with the tool drive motor and each actuator; a sensor configured to output a signal, the sensor mounted to the hand-held portion, the sensor connected to the controller using a flexible conductor; and a tensioning assembly including a biasing member, the tensioning assembly configured to apply tension to the flexible conductor while the actuator assembly moves the tool support in at least one of the plurality of degrees of freedom relative to the hand-held portion.

XXVI. A method of maintaining an electrical connection between two parts of a hand-held robotic instrument, the robotic instrument comprising a hand-held portion to be held by a user, a tool support coupled to the hand-held portion, an actuator assembly to move the tool support in a plurality of degrees of freedom relative to the hand-held portion, the actuator assembly including a plurality of actuators, and at least one of the plurality of actuators operatively interconnecting the tool support and the hand-held portion, a controller mounted to the tool support, a sensor that outputs a signal, the sensor mounted to the hand-held portion, the sensor connected to the controller using a flexible conductor, and a tensioning assembly including a biasing member, the method comprising: moving the tool support relative to hand-held portion with the plurality of actuators in at least one of the plurality of degrees of freedom; tensioning the flexible conductor with the tensioning assembly while the actuator assembly moves in the at least one of the plurality of degrees of freedom.

XXVII. A hand-held robotic instrument for use with a tool to perform surgery, the robotic instrument comprising a hand-held portion to be held by a user; a tool support coupled to the hand-held portion; an actuator assembly to move the tool support in a plurality of degrees of freedom relative to the hand-held portion, the actuator assembly including a plurality of actuators, each actuator including a motor and a position sensor; a controller mounted to the hand-held portion, the controller in communication with each actuator of the plurality of actuators using a flexible conductor; a tool drive motor to drive motion of a tool, the tool drive motor being mounted to the tool support, the tool drive motor connected to the controller using a flexible conductor; and a tensioning assembly including a biasing member, the tensioning assembly configured to apply tension to the flexible conductor of the drive motor or one or more of the actuators while the actuator assembly moves the tool support in at least one of the plurality of degrees of freedom relative to the hand-held portion.)

XVIII. A hand-held robotic instrument for use with a tool to perform surgery, the robotic instrument comprising a hand-held portion to be held by a user; a tool support coupled to the hand-held portion; an actuator assembly operatively interconnecting the tool support and the hand-held portion to move the tool support in a plurality of degrees of freedom relative to the hand-held portion, the actuator assembly including a plurality of actuators, each actuator including a motor; a controller in communication each actuator of the plurality of actuators, the controller mounted to either the hand-held portion or the tool support; a sensor that outputs a signal, the sensor being connected to the controller using a flexible conductor, the sensor mounted to the other of the hand-held portion or the tool support; and a tensioning assembly including a biasing member, the tensioning assembly configured to apply tension to the flexible conductor while the actuator assembly moves the tool support in at least one of the plurality of degrees of freedom relative to the hand-held portion.

XXIX. The instrument of clause)(XVIII, wherein the sensor is mounted to the tool support and the controller is mounted to the hand-held portion.

XXX. The instrument of clause XXIX, wherein the sensor is mounted to the hand-held portion and the controller is mounted to the tool support, and the sensor is configured to sense an input signal.)

XXXI. The instrument of clause)(XVIII, wherein the tensioning assembly is coupled to the hand-held portion.

XXXII. A hand-held surgical robotic system for supporting a surgical tool, the hand-held surgical robotic system comprising: a hand-held portion; a tool support movably coupled to the hand-held portion, the tool support configured to support the surgical tool and further comprising a tool drive motor; a plurality of actuators operatively interconnecting the tool support and the hand-held portion, the plurality of actuators configured to move the tool support relative to the hand-held portion in a plurality of degrees of freedom; a controller disposed on the hand-held portion, the controller in communication with the tool drive motor and each actuator of the plurality of actuators and a plurality of flexible circuits connecting the instrument controller with each of the plurality of actuators, wherein the plurality of flexible circuits maintain the connection between the controller and the plurality of actuators while the tool support is moved in the plurality of degrees of freedom relative to the hand-held portion, wherein at least one of the plurality of flexible circuits has a longitudinal axis, and the at least one of the plurality of flexible circuits extend from a coupling point on one of the plurality of actuators and engaging a flex guide on the tool support or hand-held portion to minimize deformation of the at least one flexible circuit in a one or more degrees of freedom.

XXXIII. A method of maintaining an electrical connection between two parts of a hand-held robotic instrument, the robotic instrument comprising a hand-held portion to be held by a user, a tool support coupled to the hand-held portion, an actuator assembly to move the tool support in a plurality of degrees of freedom relative to the hand-held portion, the actuator assembly including a plurality of actuators, a controller mounted to the tool support or the hand-held portion, a sensor that outputs a signal, the sensor coupled to the other of the hand-held portion and the tool support (opposite the controller), the sensor connected to the controller using a flexible conductor, and a tensioning assembly including a biasing member, the method comprising: moving the tool support relative to hand-held portion with the plurality of actuators in at least one of the plurality of degrees of freedom; tensioning the flexible conductor with the tensioning assembly while the actuator assembly moves in the at least one of the plurality of degrees of freedom.

The invention claimed is:

1. A robotic hand-held surgical instrument comprising:
a hand-held portion to be held by a user;
a tool support coupled to the hand-held portion;
an actuator assembly operatively interconnecting the tool support and the hand-held portion to move the tool support to move the tool in a plurality of degrees of freedom relative to the hand-held portion to align the tool, the actuator assembly including a plurality of actuators, each actuator including a motor;
a controller mounted to the tool support, the controller in communication with the motor;
the hand-held portion including an input module, the input module including:
    a trigger; and
    a sensor that outputs a signal representative of a trigger position, the sensor in communication with the controller; and
a flexible circuit connecting the controller to the input module;
a tensioning assembly comprising:
    a housing;
    a tension member pivotably coupled to the housing;
    a guide member within the housing, the guide member having a curvature that is concentric to a movement of the tension member;
    a biasing member in communication with the tension member to apply tension to the flexible circuit, wherein the flexible circuit is connected with the input module such that the flexible circuit is guided by the tensioning assembly with the biasing member configured to apply tension to the flexible circuit while the tool support moves in the plurality of degrees of freedom relative to the hand-held portion.

2. The robotic hand-held surgical instrument of claim 1, wherein the tensioning member includes a routing member in contact with the flexible circuit, the routing member comprising a roller member that rotates about an axis to reduce drag on the flexible circuit.

3. The robotic hand-held surgical instrument of claim 2, wherein flexible circuit is a printed circuit.

4. The robotic hand-held surgical instrument of claim 1, wherein the biasing member applies a force against the flexible circuit such that when tool support is moved in a direction toward the hand-held portion, the tensioning assembly takes up slack in the flexible circuit, and when the tool support is moved away from the hand-held portion, the flexible circuit applies a force greater than that of the biasing member so that the flexible circuit has more available length to travel.

5. The robotic hand-held surgical instrument of claim 1, wherein the flexible circuit connected with the input module includes an adjustment loop, the adjustment loop arranging the flexible circuit about a longitudinal pivot axis of the tool support at a home position, the adjustment loop is configured to expand and contract as the tool support is moved in a pitch degree of freedom relative to the hand-held portion.

6. A hand-held robotic surgical instrument for use with a tool to perform surgery, the robotic instrument comprising;
a hand-held portion to be held by a user;
a tool support coupled to the hand-held portion, the tool support comprising a tool drive motor to drive motion of the tool;
an actuator assembly to move the tool support to move the tool in a plurality of degrees of freedom relative to the hand-held portion, the actuator assembly including a plurality of actuator with at least one actuator interconnecting the tool support and the hand-held portion, each actuator including a motor;
a controller mounted to the tool support, the controller in communication with the tool drive motor and each motor of the plurality of actuators;
an input module mounted to the hand-held portion, the input module including:
    a trigger movable relative to the hand-held portion;
    a trigger sensor that outputs a signal representative of a trigger position; and
a flexible conductor extending from the controller to the trigger sensor;
a tensioning assembly comprising:
    a housing;
    a tension member pivotably coupled to the housing; and
    a guide member within the housing, the guide member having a curvature that is concentric to a movement of the tension member;
    wherein the tension member is configured to apply load to a portion of the flexible conductor located between the tool support and the trigger sensor to control tension on to the flexible conductor while the tool support moves in the plurality of degrees of freedom relative to the hand-held portion.

7. The hand-held robotic surgical instrument of claim 6, wherein the flexible conductor is a flexible circuit including a plurality of circuit leads.

8. The hand-held robotic surgical instrument of claim 7, wherein the tensioning assembly applies a force against the flexible circuit such that when a portion of tool support is moved in a direction toward the hand-held portion, the tensioning assembly tensions the flexible circuit, and when the tool support is moved away from the hand-held portion, the actuator assembly applies a force greater than that of a biasing member so that the flexible circuit has more available length to travel.

9. The hand-held robotic surgical instrument of claim 7, wherein the tensioning assembly includes a housing and a tension member moveably coupled to the housing, the tension member configured to apply load to a portion of the flexible circuit by contacting the flexible circuit between the tool support and the trigger sensor.

10. The hand-held robotic surgical instrument of claim 9, wherein the tension member is a swing arm, the swing arm including a first end and a second end, the first end pivotally connected with the housing.

11. The hand-held robotic surgical instrument of claim 10, further comprising a biasing member positioned between the housing and the swing arm.

12. The hand-held robotic surgical instrument of claim 11, wherein the swing arm at the second end includes a routing member, the routing member located opposite the pivot connection of the swing arm.

13. The hand-held robotic surgical instrument of claim 12, wherein the routing member is rotatable relative the swing arm to reduce drag on flexible circuit.

14. The hand-held robotic surgical instrument of claim 12, wherein the flexible circuit is routed around the routing member such that the biasing member applies a force through the swing arm onto the flexible circuit.

15. The hand-held robotic surgical instrument of claim 11, wherein the biasing member is disposed about the guide member to guide the biasing member during movement of the swing arm.

16. The hand-held robotic surgical instrument of claim 12, wherein the tension member is coupled to the biasing member, and the tensioning assembly includes a plurality of routing members, the plurality of routing members including at least one fixed routing member and at least one routing member coupled to the tension member.

17. The hand-held robotic surgical instrument of claim 16, wherein the at least one fixed routing member is roller member that rotates about an axis to reduce drag on the flexible conductor.

18. The hand-held robotic surgical instrument of claim 6, wherein the flexible conductor includes an adjustment loop, the adjustment loop arranging the flexible conductor about a longitudinal pivot axis of the tool support at a home position, the adjustment loop is configured to expand and contract as the tool support is moved in a pitch degree of freedom relative to the hand-held portion.

19. A hand-held robotic surgical instrument for use with a tool to perform surgery, the robotic instrument comprising;

a hand-held portion to be held by a user;

a tool support coupled to the hand-held portion, the tool support comprising a tool drive motor to drive motion of the tool;

an actuator assembly to move the tool support to move the tool in a plurality of degrees of freedom relative to the hand-held portion, the actuator assembly including a plurality of actuator with at least one actuator interconnecting the tool support and the hand-held portion, each actuator including a motor;

a controller mounted to the tool support, the controller in communication with the tool drive motor and each motor of the plurality of actuators;

an input module mounted to the hand-held portion, the input module including:

a trigger movable relative to the hand-held portion;

a trigger sensor that outputs a signal representative of a trigger position; and a flexible conductor extending from the controller to the trigger sensor;

a tensioning assembly to control tension on to the flexible conductor while the tool support moves in the plurality of degrees of freedom relative to the hand-held portion, the tensioning assembly comprising:

a pivotable swing arm in contact with and configured to apply load to a portion of the flexible conductor;

a guide member having a curvature that is concentric to a movement of the swing arm.

20. The hand-held robotic surgical instrument of claim 19, wherein the tensioning assembly further comprises a biasing member to provide a force onto the swing arm.

* * * * *